United States Patent
Schwendeman et al.

(10) Patent No.: US 10,220,046 B2
(45) Date of Patent: Mar. 5, 2019

(54) COMPOSITIONS AND METHODS FOR DISEASE TREATMENT USING NANOPARTICLE DELIVERED COMPOUNDS

(71) Applicant: THE REGENTS OF THE UNIVERSITY OF MICHIGAN, Ann Arbor, MI (US)

(72) Inventors: Anna Schwendeman, Ann Arbor, MI (US); Mark Cohen, Ann Arbor, MI (US); Chitra Subramanian, Ann Arbor, MI (US); Rui Kuai, Ann Arbor, MI (US); Dan Li, Ann Arbor, MI (US); Peter White, Ann Arbor, MI (US); James Moon, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/325,972

(22) PCT Filed: Jul. 14, 2015

(86) PCT No.: PCT/US2015/040404
§ 371 (c)(1),
(2) Date: Jan. 12, 2017

(87) PCT Pub. No.: WO2016/011049
PCT Pub. Date: Jan. 21, 2016

(65) Prior Publication Data
US 2017/0157149 A1  Jun. 8, 2017

Related U.S. Application Data

(60) Provisional application No. 62/024,223, filed on Jul. 14, 2014.

(51) Int. Cl.
| | |
|---|---|
| *A61K 31/00* | (2006.01) |
| *A61K 9/16* | (2006.01) |
| *A61K 38/17* | (2006.01) |
| *A61K 31/585* | (2006.01) |
| *A61K 9/51* | (2006.01) |
| *A61K 31/58* | (2006.01) |

(52) U.S. Cl.
CPC .............. *A61K 31/585* (2013.01); *A61K 9/16* (2013.01); *A61K 9/5123* (2013.01); *A61K 31/58* (2013.01); *A61K 38/1709* (2013.01)

(58) Field of Classification Search
CPC .... A61K 31/585; A61K 38/1709; A61K 9/16; A61K 38/17
USPC .......................................... 424/499; 530/300
See application file for complete search history.

(56) References Cited

U.S. PATENT DOCUMENTS

| | | | |
|---|---|---|---|
| 6,753,313 B1 | 6/2004 | Dasseux | |
| 7,282,593 B2 | 10/2007 | Nair et al. | |
| 8,598,339 B2 | 12/2013 | Timmermann et al. | |
| 2003/0008827 A1 | 1/2003 | Dasseux et al. | |
| 2005/0226950 A1* | 10/2005 | Sangwan ............... | A61K 36/81 424/769 |
| 2006/0252694 A1 | 11/2006 | Dasseux et al. | |
| 2009/0088412 A1 | 4/2009 | Wu et al. | |
| 2011/0305719 A1* | 12/2011 | Naziruddin ............ | A61K 31/58 424/184.1 |
| 2012/0196815 A1* | 8/2012 | Timmermann .......... | C07J 17/00 514/26 |

FOREIGN PATENT DOCUMENTS

| | | |
|---|---|---|
| WO | WO 2010030395 A2 | 3/2010 |
| WO | WO 2010053655 A2 | 5/2010 |
| WO | WO 2013126776 A1 | 8/2013 |
| WO | WO 2016011049 A2 | 1/2016 |

OTHER PUBLICATIONS

Search Report of related PCT/US2015/040404, dated Feb. 2, 2016, 17 pages.
Almquist et al., "Synthesis and biological activity of a ketomethylene analogue of a tripeptide inhibitor of angiotensin converting enzyme." J Med Chem. Dec. 1980;23(12):1392-8.
Anantharamaiah et al., "Studies of synthetic peptide analogs of the amphipathic helix. Structure of complexes with dimyristoyl phosphatidylcholine." J Biol Chem. Aug. 25, 1985;260(18):10248-55.
Anbalagan et al., "Influence of an Indian medicine (Ashwagandha) on acute-phase reactants in inflammation." Indian J Exp Biol. Mar. 1981;19(3):245-9.
Bargagna-Mohan et al., "The tumor inhibitor and antiangiogenic agent withaferin A targets the intermediate filament protein vimentin." Chem Biol. Jun. 2007;14(6):623-34.
Basak et al., "Biotinylation of an enkephalin-containing heptapeptide via various spacer arms. Synthesis, comparative binding studies toward avidin, and application as substrates in enzymatic reactions." Bioconjug Chem. Jul.-Aug. 1994;5(4):301-5.
Berruti et al., "Adrenal cancer: ESMO Clinical Practice Guidelines for diagnosis, treatment and follow-up." Ann Oncol. Oct. 2012;23 Suppl 7:vii131-8.
Bourdeau et al., "Recent advances in adrenocortical carcinoma in adults." Curr Opin Endocrinol Diabetes Obes. Jun. 2013;20(3):192-7.
Chou et al., "Empirical predictions of protein conformation." Annu Rev Biochem. 1978;47:251-76.
Chou et al., "Quantitative analysis of dose-effect relationships: the combined effects of multiple drugs or enzyme inhibitors." Adv Enzyme Regul. 1984;22:27-55.

(Continued)

*Primary Examiner* — Julie Ha
(74) *Attorney, Agent, or Firm* — Casimir Jones, S.C.; Tanya Arenson

(57) ABSTRACT

Provided herein are compositions and methods for the treatment of diseases, such as hyperproliferative diseases, employing compounds formulated for pharmaceutical and research use via nanoparticles.

7 Claims, 11 Drawing Sheets

Specification includes a Sequence Listing.

(56) References Cited

OTHER PUBLICATIONS

Dasgupta et al., "Design of helix ends. Amino acid preferences, hydrogen bonding and electrostatic interactions." Int J Pept Protein Res. May 1993;41(5):499-511.
Demoor et al., "Branched synthetic constructs that mimic the physico-chemical properties of apolipoprotein AI in reconstituted high-density lipoproteins." Eur J Biochem. Jul. 1, 1996;239(1):74-84.
Dhuley "Effect of some Indian herbs on macrophage functions in ochratoxin A treated mice." J Ethnopharmacol. Sep. 1997;58(1):15-20.
Dhuley et al., "Effect of ashwagandha on lipid peroxidation in stress-induced animals." J Ethnopharmacol. Mar. 1998;60(2):173-8.
Doig et al., "N- and C-capping preferences for all 20 amino acids in alpha-helical peptides." Protein Sci. Jul. 1995;4(7):1325-36.
Doig et al., "Determination of free energies of N-capping in alpha-helices by modification of the Lifson-Roig helix-coil therapy to include N- and C-capping." Biochemistry. Mar. 22, 1994;33(11):3396-403.
Doig et al., "Structures of N-termini of helices in proteins." Protein Sci. Jan. 1997;6(1):147-55.
Edelstein et al., "In vitro conversion of proapoprotein A-I to apoprotein A-I. Partial characterization of an extracellular enzyme activity." J Biol Chem. Oct. 10, 1983;258(19):11430-3.
Eisenberg et al., "Analysis of membrane and surface protein sequences with the hydrophobic moment plot." J Mol Biol. Oct. 15, 1984;179(1):125-42.
Falsey et al., "Actin microfilament aggregation induced by withaferin A is mediated by annexin II." Nat Chem Biol. Jan. 2006;2(1):33-8.
Glover et al., "Current management options for recurrent adrenocortical carcinoma." Onco Targets Ther. Jun. 6, 2013;6:635-43.
Hann et al., "On the double bond isostere of the peptide bond: preparation of an enkephalin analogue" J. Chem. Soc., Perkin Trans. 1, 1982, 307-314.
Harper et al., "Helix stop signals in proteins and peptides: the capping box." Biochemistry. Aug. 3, 1993;32(30):7605-9.
Holladay et al., "Synthesis of hydroxyethylene and ketomethylene dipeptide isosteres" Tetrahedron Letters, vol. 24, Issue 41, 1983, pp. 4401-4404.
Hruby et al., "Conformational restrictions of biologically active peptides via amino acid side chain groups." Life Sci. Jul. 19, 1982;31(3):189-99.
Hudson et al., "Methionine enkephalin and isosteric analogues. I. Synthesis on a phenolic resin support." Int J Peptide Protein Res. 1979;14(3):177-85.
Jain et al., "TOP2A is overexpressed and is a therapeutic target for adrenocortical carcinoma." Endocr Relat Cancer. May 21, 2013;20(3):361-70.
Jayaprakasam et al., "Growth inhibition of human tumor cell lines by withanolides from Withania somnifera leaves." Life Sci. Nov. 21, 2003;74(1):125-32.
Jennings-White et al., "Synthesis of ketomethylene analogs of dipeptides" vol. 23, Issue 25, 1982, pp. 2533-2534.
Jonas "Reconstitution of high-density lipoproteins." Methods Enzymol. 1986;128:553-82.
Kaileh et al., "Withaferin a strongly elicits IkappaB kinase beta hyperphosphorylation concomitant with potent inhibition of its kinase activity." J Biol Chem. Feb. 16, 2007;282(7):4253-64.
Khan et al., "Mitogen-activated protein kinase inhibition and cardioplegia-cardiopulmonary bypass reduce coronary myogenic tone." Circulation. Sep. 9, 2003;108 Suppl 1:II348-53.
Kneib-Cordonier et al., "Orthogonal solid-phase synthesis of human gastrin-I under mild conditions." Int J Peptide Protein Res. Jun. 1990;35(6):527-38.
Lavie, et al. "Constituents of Withania sornnifera Dun. III. The Side Chain of Withaferin*" (1965) J. Org. Chem. 30:1774-1776.
Mendez et al., "Synthetic amphipathic helical peptides that mimic apolipoprotein A-I in clearing cellular cholesterol." J Clin Invest. Oct. 1994;94(4):1698-705.
Morley "Modulation of the action of regulatory peptides by structural modification" 1980, Trends Pharm. Sci. 1:463-468.
Nakagawa et al., "The use of polymer-bound oximes for the synthesis of large peptides usable in segment condensation: synthesis of a 44 amino acid amphiphilic peptide model of apolipoprotein A-1" 1985, J. Am. Chem. Soc. 107:7087-7092.
Odaert et al., "Nonnative capping structure initiates helix folding in an annexin I fragment. A 1H NMR conformational study." Biochemistry. Oct. 3, 1995;34(39):12820-9.
Olson et al., "Concepts and progress in the development of peptide mimetics." J Med Chem. Oct. 15, 1993;36(21):3039-49.
Palgunachari et al., "Only the two end helices of eight tandem amphipathic helical domains of human apo A-I have significant lipid affinity. Implications for HDL assembly." Arterioscler Thromb Vasc Biol. Feb. 1996;16(2):328-38.
Petukhov et al., "Factors that affect the stabilization of alpha-helices in short peptides by a capping box." Biochemistry. Jan. 16, 1996;35(2):387-97.
Ray et al., "Withasteroids, a growing group of naturally occurring steroidal lactones." Fortschr Chem Org Naturst. 1994;63:1-106.
Richardson et al., "Amino acid preferences for specific locations at the ends of alpha helices." Science. Jun. 17, 1988;240(4859):1648-52.
Rosseneu et al., "Analysis of the Primary and of the Secondary Structure of the Apolipoproteins," In: Structure and Function of Lipoproteins, Ch. 6, 159-183, CRC Press, Inc., 1992.
Seale et al., "Sequence determinants of the capping box, a stabilizing motif at the N-termini of alpha-helices." Protein Sci. Oct. 1994;3(10):1741-5.
Sen et al., "Apoptosis is induced in leishmanial cells by a novel protein kinase inhibitor withaferin A and is facilitated by apoptotic topoisomerase I-DNA complex." Cell Death Differ. Feb. 2007;14(2):358-67.
Spatola et al., "Structure-activity relationships of enkephalins containing serially replaced thiomethylene amide bond surrogates." Life Sci. Apr. 7, 1986;38(14):1243-9.
Srinivasan et al., "Par-4-dependent apoptosis by the dietary compound withaferin A in prostate cancer cells." Cancer Res. Jan. 1, 2007;67(1):246-53.
Subramanian et al., "Withanolides are potent novel targeted therapeutic agents against adrenocortical carcinomas." World J Surg. Jun. 2014;38(6):1343-52.
Vanloo et al., "Characterization of the discoidal complexes formed between apoA-I-CNBr fragments and phosphatidylcholine. Subramanian et al., Withanolides are potent novel targeted therapeutic agents against adrenocortical carcinomas." World J Surg. Jun. 2014;38(6):1343-52. J Lipid Res. Aug. 1991;32(8):1253-64.
Venkatachalapathi et al., "Use of Synthetic Peptides in the Structural and Functional Studies of Apolipoprotein A-1" 1991, Mol. Conformation and Biol. Interactions, Indian Acad. Sci. B:585-596.
Venkatachalapathi et al., "Effect of end group blockage on the properties of a class A amphipathic helical peptide." Proteins. Apr. 1993;15(4):349-59.
Yang et al., "The tumor proteasome is a primary target for the natural anticancer compound Withaferin A isolated from Indian winter cherry". Mol Pharmacol. Feb. 2007;71(2):426-37.
Zanis et al., "Intracellular and extracellular processing of human apolipoprotein A-I: secreted apolipoprotein A-I isoprotein 2 is a propeptide." Proc Natl Acad Sci U S A. May 1983;80(9):2574-8.
Zhou et al., "Alpha helix capping in synthetic model peptides by reciprocal side chain-main chain interactions: evidence for an N terminal "capping box"." Proteins. Jan. 1994;18(1):1-7.
Ziauddin et al., "Studies on the immunomodulatory effects of Ashwagandha." J Ethnopharmacol. Feb. 1996;50(2):69-76.

* cited by examiner

Before passing through column | After passing through column | Frozen and thawn at 37°C

COMPOSITIONS AND METHODS FOR DISEASE TREATMENT USING NANOPARTICLE DELIVERED COMPOUNDS The present application is a 371 U.S. National Phase Entry of pending International Application No. PCT/US2015/040404, filed Jul. 14, 2015, which claims priority to U.S. Provisional Patent Application Ser. No. 62/024,223, filed Jul. 14, 2014, the disclosures of which are herein incorporated by reference in their entireties.

FIELD

Provided herein are compositions and methods for the treatment of diseases, such as hyperproliferative diseases, employing compounds formulated for pharmaceutical and research use via nanoparticles.

BACKGROUND

Currently, patients with similar type of cancer receive similar treatment, even though the development of a tumor and further progression of the disease is often different in each individual. This traditional approach to cancer treatment has always entailed accepting the risks of individualized adverse reactions, including death, in some cases and inefficiencies that inflate health care costs and undermine patient care.

Additionally, some cancers have few if any options for treatment, and often such treatment options themselves present high levels of toxicity. For example, chemotherapeutic strategies for adrenocortical carcinoma (ACC) carry significant toxicities. Adrenocortical carcinoma is a rare endocrine malignancy (approximately 500 new cases per year in the US) that carries a poor prognosis with advanced disease. Unfortunately a majority of patients will present with advanced disease at the time of diagnosis and once metastatic, the disease has a low (10-20%) five-year survival. For patients with metastatic disease, the only current FDA approved therapeutic is the adrenolytic agent mitotane, with initial response rates of 20-30% in advanced ACC patients and an improvement in survival rate from 14-50 months. Recent years have evaluated mitotane in combination with cytotoxic chemotherapeutics as in the Italian protocol, (etoposide, doxorubicin, cisplatin; EDP) or with streptozocin. EDP-M has been shown to carry a higher response rate (23.2% vs. 9.2%) and progression free survival (5.0 months vs. 2.1 months) compared to mitotane with streptozotocin (Berruti et al., Annals of oncology: official journal of the European Society for Medical Oncology/ESMO. 2012 October; 23 Suppl 7:vii 131-8; Bourdeau et al., Current opinion in endocrinology, diabetes, and obesity. 2013 June; 20(3):192-7; Glover et al., OncoTargets and therapy. 2013; 6:635-43; each of which is herein incorporated by reference in its entirety). Dose-limiting toxicities such as adrenal insufficiency, dizziness, vertigo, central nervous disturbances, hyperlipidemia, and gastrointestinal disorders remain a significant issue with both mitotane and cytotoxic agents given in combination.

What are needed are new and better approaches for cancer management.

SUMMARY

Provided herein are compositions and methods for the treatment of diseases such as hyperproliferative and related diseases and conditions, including research, diagnostic, and therapeutic indications. In particular, provided herein are nanoparticle-associated compounds, nanoparticle formulations, and their uses.

In some embodiments, the nanoparticles include an anticancer compound. In some embodiments, the anticancer compound is a hydrophobic compound (e.g., log P>2, >3, >4). In some embodiments, exemplary anticancer agents suitable for use in compositions and methods include, but are not limited to: 1) alkaloids, including microtubule inhibitors (e.g., vincristine, vinblastine, and vindesine, etc.), microtubule stabilizers (e.g., paclitaxel (TAXOL), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosphamide, and busulfan (MYLERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies conjugated with anticancer drugs, toxins, and/or radionuclides, etc.; 9) biological response modifiers (e.g., interferons (e.g., IFN-α, etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy agents; 14) antisense therapy agents; 15) tumor vaccines; 16) therapies directed against tumor metastases (e.g., batimastat, etc.); 17) angiogenesis inhibitors; 18) proteosome inhibitors (e.g., VELCADE); 19) inhibitors of acetylation and/or methylation (e.g., HDAC inhibitors); 20) modulators of NF kappa B; 21) inhibitors of cell cycle regulation (e.g., CDK inhibitors); and 22) modulators of p53 protein function. In some embodiments, the two or more anticancer compounds (a "combination" therapy) are included in the nanoparticle. In some embodiments the combination therapy includes one or more or all of doxorubicin, cisplatin, etoposide, and mitotane.

In some embodiments, the nanoparticles include a withanolide compound. Thus, in some embodiments, provided herein are compositions comprising a nanoparticle, wherein the nanoparticle comprises a withanolide compound. A wide variety of withanolide compounds are contemplated. The composition may be formulated for desired use in vitro (e.g., for drug screening, basic research, safety or efficacy testing, quality control/quality assurance testing, etc.) or in vivo (e.g., pharmaceutical administration to a subject, e.g., a human subject).

In some embodiments, the withanolide compound comprises withaferin A. In some embodiments, the withanolide compound comprises a structure defined by any of Formulas (I) through (XVII) (described in detail below).

In some embodiments, the nanoparticles comprise any structure that increases the efficacy and/or safety profile of the anticancer (e.g., withanolide) compound, including, but not limited to, increased bioavailability, increased selectivity for cancer cells, increased ability to treat cancer (e.g., reduce tumor size, prevent cancer, prevent metastasis, reduce rate of cancer growth, kill cancer cells, etc.). For example, in some embodiments, the nanoparticle is recognized by scavenger receptor class BI (SR-BI). In such embodiments, the nanoparticles preferentially deliver drug payload to cells with increased SR-BI (e.g., cancer cells).

In some embodiments, the nanoparticle comprises high-density lipoprotein (HDL). In some embodiments, the HDL is synthetic HDL (sHDL). In some embodiments, the synthetic HDL comprises a synthetic ApoA-I mimic peptide. In some embodiments, the ApoA-I mimic peptide comprises 15-22 amino acids from the sequence $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$-$X_{20}$-$X_{21}$-$X_{22}$ (SEQ ID NO:4) wherein: $X_1$ is Pro (P), Ala (A), Gly (G), Gln (Q), Asn (N), Asp (D) or D-Pro (p); $X_2$ is an aliphatic amino acid; $X_3$ is Leu (L) or Phe (F); $X_4$ is Glu (E); $X_5$ is an aliphatic amino acid; $X_6$ is Leu (L) or Phe (F); $X_7$ is Glu (E) or Leu (L); $X_8$ is Asn (N) or Gln (Q); $X_9$ is Leu (L); $X_{10}$ is Leu (L), Trp (W) or Gly (G); $X_{11}$ is an acidic amino acid; $X_{12}$ is Arg (R); $X_{13}$ is Leu (L) or Gly (G); $X_{14}$ is Leu (L), Phe (F) or Gly (G); $X_{15}$ is Asp (D); $X_{16}$ is Ala (A); $X_{17}$ is Leu (L); $X_{18}$ is Asn (N) or Gln (Q); $X_{19}$ is a basic amino acid; $X_{20}$ is a basic amino acid; $X_{21}$ is Leu (L); and $X_{22}$ is a basic amino acid.

In some embodiments, sHDL comprises components of natural HDL. In some embodiments, the sHDL nanoparticle comprises apolipoprotein at a concentration of about 20-50 g/L. In some embodiments, the sHDL nanoparticle comprises lipid from 20-70% (mass per unit volume). In some embodiments, the molar ratio of apoliprotein:lipid is in the range of 1:20 to 1:100. The lipid may be any lipid which is a functional, biologically active component of naturally-occurring HDL or equivalent. Such lipids include phospholipids, cholesterol, cholesterol-esters, fatty acids and/or triglycerides. Preferably, the lipid is a phospholipid. Non-limiting examples of phospholipids include phosphatidylcholine (PC) (lecithin), phosphatidic acid, phosphatidylethanolamine (PE) (cephalin), phosphatidylglycerol (PG), phosphatidylserine (PS), phosphatidylinositol (PI) and sphingomyelin (SM) or natural or synthetic derivatives thereof. Natural derivatives include egg PC, egg PG, soy bean PC, hydrogenated soy bean PC, soy bean PG, brain PS, sphingolipids, brain SM, galactocerebroside, gangliosides, cerebrosides, cephalin, cardiolipin, and dicetylphosphate. Synthetic derivatives include dipahnitoylphosphatidylcholine (DPPC), didecanoylphosphatidylcholine (DDPC), dierucoylphosphatidylcholine (DEPC), dimyristoylphosphatidylcholine (DMPC), distearoylphosphatidylcholine (DSPC), dilaurylphosphatidylcholine (DLPC), palmitoyloleoylphosphatidylcholine (POPC), palmitoylmyristoylphosphatidylcholine (PMPC), palmitoylstearoylphosphatidylcholine (PSPC), dioleoylphosphatidylcholine (DOPC), dioleoylphosphatidylethanolamine (DOPE), dilauroylphosphatidylglycerol (DLPG), distearoylphosphatidylglycerol (DSPG), dimyristoylphosphatidylglycerol (DMPG), dipalmitoylphosphatidylglycerol (DPPG), distearoylphosphatidylglycerol (DSPG), dioleoylphosphatidylglycerol (DOPG), palmitoyloleoylphosphatidylglycerol (POPG), dimyristoylphosphatidic acid (DMPA), dipalmitoylphosphatidic acid (DPPA), distearoylphosphatidic acid (DSPA), dimyristoylphosphatidylethanolamine (DMPE), dipalmitoylphosphatidylethanolamine (DPPE), dimyristoylphosphatidylserine (DMPS), dipalmitoylphosphatidylserine (DPPS), distearoylphosphatidylethanolamine (DSPE), dioleoylphosphatidylethanolamine (DOPE) dioleoylphosphatidylserine (DOPS), dipalmitoylsphingomyelin (DPSM) and distearoylsphingomyelin (DSSM). The phospholipid can also be a derivative or analogue of any of the above phospholipids.

In some embodiments, the nanoparticle contains greater than 0.1% drug by mass or volume (e.g., >1%, >2%, >5%, >10%).

In some embodiments, the nanoparticle is a homogenous particle having an average size (diameter) from 5-15 nm.

The withanolide-containing composition may be provided alone, or may be further provided with a second therapeutic agent (e.g., anti-cancer agent) (e.g., co-administration of the withanolide and the second anti-cancer agent). In some embodiments, the second therapeutic agent is also provided in the nanoparticle. In other embodiments, the second therapeutic agent is provided in a separate composition that is to be administered to a subject separately (e.g., sequentially or in parallel) with the withanolide-containing nanoparticle.

Also provided herein are methods of using the anticancer (e.g., withanolide) containing compositions for research, diagnostic, or therapeutics uses. For example, in some embodiments, methods are provided comprising administering any of the compositions to a subject (e.g., a human subject). In some embodiments, the subject has a hyperproliferative disorder (e.g., cancer). In some embodiments, the subject is suspected of having cancer or is at risk of having cancer. In some embodiment, the subject previously had cancer. In some embodiments, the method comprises co-administering an additional anti-cancer therapy (e.g., radiation, chemotherapy, etc.) to the subject along with the nanoparticle composition. In some embodiments, the compositions are administered prior to, during, or following surgical removal of a tumor.

Further provided herein are uses of any of the above compositions (e.g., use for the treatment of cancer or other diseases or for the manufacture of a medicament for the treatment of cancer or other diseases).

Definitions

Unless defined otherwise, all terms of art, notations and other scientific terms or terminology used herein have the same meaning as is commonly understood by one of ordinary skill in the art to which this disclosure belongs. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

As used herein, "a" or "an" means "at least one" or "one or more."

As used herein, the terms "detect", "detecting" or "detection" may describe either the general act of discovering or discerning or the specific observation of a detectably labeled composition.

As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues (e.g., tissue biopsy), and gases. Biological samples include blood products, such as plasma, serum and the like. Such examples are not however to be construed as limiting the sample types.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject is suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass) but for whom a confirmatory test (e.g., biopsy and/or histology) has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, and blood test. A "preliminary diagnosis" is one based only on visual (e.g., CT scan or the presence of a lump) and antigen tests.

As used herein, the term "subject at risk for cancer" refers to a subject with one or more risk factors for developing a specific cancer. Risk factors include, but are not limited to, gender, age, genetic predisposition, environmental expose, and previous incidents of cancer, preexisting non-cancer diseases, and lifestyle.

As used herein, the term "non-human animals" refers to all non-human animals including, but not limited to, vertebrates such as rodents, non-human primates, ovines, bovines, ruminants, lagomorphs, porcines, caprines, equines, canines, felines, ayes, etc.

As used herein, the term "effective amount" refers to the amount of a composition (e.g., a nanoparticle comprising a drug) sufficient to effect beneficial or desired results. An effective amount can be administered in one or more administrations, applications or dosages and is not intended to be limited to a particular formulation or administration route.

As used herein, the term "administration" refers to the act of giving a drug, prodrug, or other agent, or therapeutic treatment (e.g., nanoparticles) to a subject (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like.

As used herein, the term "co-administration" refers to the administration of at least two agent(s) (e.g., a nanoparticle comprising a compound and another anti-cancer agent) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

As used herein, the term "toxic" refers to any detrimental or harmful effects on a subject, a cell, or a tissue as compared to the same cell or tissue prior to the administration of the toxicant.

As used herein, the term "pharmaceutical composition" refers to the combination of an active agent with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, or that are sufficiently physiological tolerated when administered to a subject.

As used herein, the term "pharmaceutically acceptable salt" refers to any salt (e.g., obtained by reaction with an acid or a base) of a compound that is physiologically tolerated in the target subject (e.g., a mammalian subject, and/or in vivo or ex vivo, cells, tissues, or organs). "Salts" of the compounds may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds and their pharmaceutically acceptable acid addition salts. Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like. Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of compounds compounded with a suitable cation such as $Na^+$, $NH_4^+$, and $NW_4^+$ (wherein W is a $C_{1-4}$ alkyl group), and the like. For therapeutic use, salts are contemplated as being pharmaceutically acceptable. However, salts of acids and bases that are non-pharmaceutically acceptable may also find use, for example, in the preparation or purification of a pharmaceutically acceptable compound.

As used herein, the terms "drug" and "chemotherapeutic agent" refer to pharmacologically active molecules that are used to diagnose, treat, or prevent diseases or pathological conditions in a physiological system (e.g., a subject, or in vivo, in vitro, or ex vivo cells, tissues, and organs). Drugs act by altering the physiology of a living organism, tissue, cell, or in vitro system to which the drug has been administered. It is intended that the terms "drug" and "chemotherapeutic agent" encompass anti-hyperproliferative and antineoplastic compounds as well as other biologically therapeutic compounds.

The term "analogue" as used herein means a compound in which one or more individual atoms or functional groups have been replaced, either with a different atom or a different functional, generally giving rise to a compound with similar properties.

The term "derivative" as used herein means a compound that is formed from a similar, beginning compound by attaching another molecule or atom to the beginning compound.

Further, derivatives, according to the invention, encompass one or more compounds formed from a precursor compound through addition of one or more atoms or molecules or through combining two or more precursor compounds.

A "hyperproliferative disease," as used herein refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A "metastatic" cell or tissue means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell. Metaplasia can occur in epithelial or connective tissue cells. A typical metaplasia involves a somewhat disorderly metaplastic epithelium.

As used herein, the term "neoplastic disease" refers to any abnormal growth of cells or tissues being either benign (non-cancerous) or malignant (cancerous).

As used herein the term, "in vitro" refers to an artificial environment and to processes or reactions that occur within an artificial environment. In vitro environments can consist of, but are not limited to, test tubes. The term "in vivo" refers to the natural environment (e.g. cell culture) and to processes or reactions that occur within a natural environment.

As used herein, the term "cell culture" refers to any culture of cells. Included within this term are continuous cell lines (e.g., with an immortal phenotype), primary cell cultures, finite cell lines (e.g., non-transformed cells), and any other cell population maintained in culture, including oocytes and embryos.

DETAILED DESCRIPTION

Figure 1:
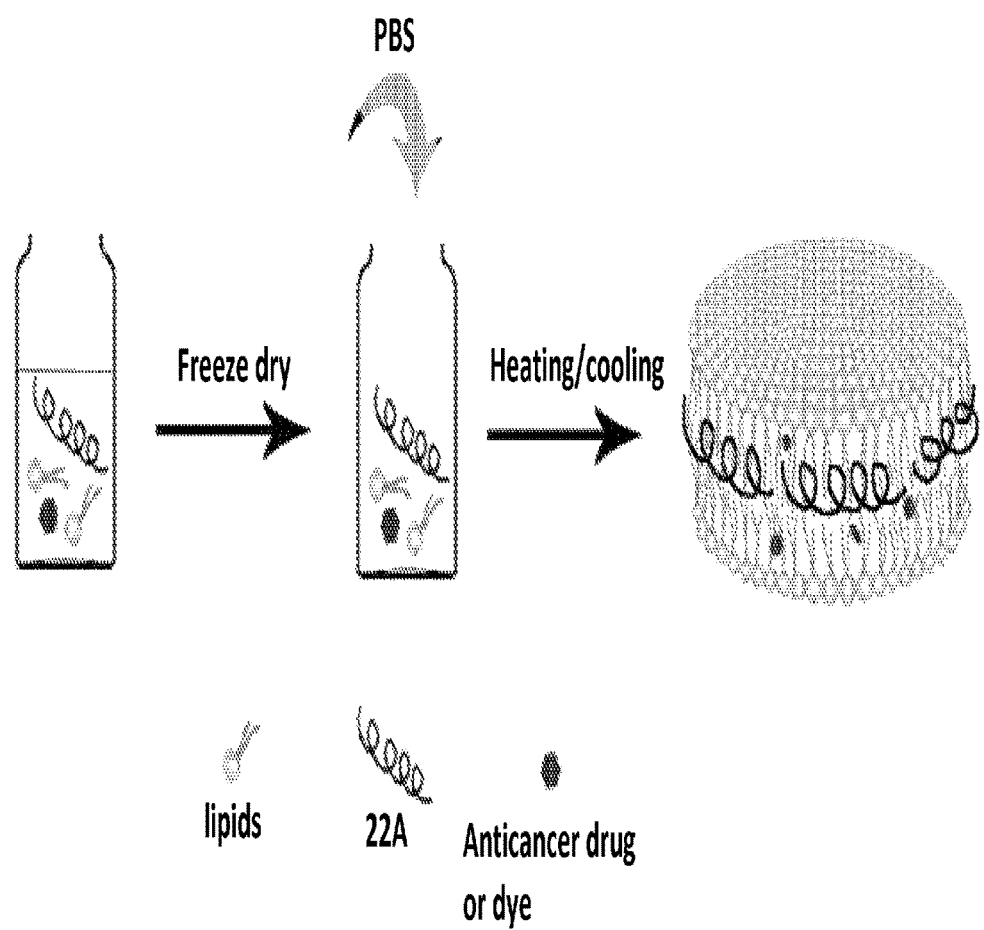
FIG. 1 shows an exemplary schematic of a process for the preparation of nanoparticles.

Provided herein are compositions and methods for the treatment of diseases, such as hyperproliferative diseases, employing compounds formulated for pharmaceutical and research use via nanoparticles. In particular, provided herein are nanoparticle-associated compounds, nanoparticle formulations, and their uses. In some embodiments, the nanoparticles include an anticancer compound. Illustrative examples of the technology are provided below with withanolide compounds as the agent, which in some embodiments provides an anticancer agent. It should be understood that other agents for other diseases and other anticancer agents may be employed (see e.g., Examples 14 and 15 providing data for a diverse set of anticancer agents other than withanolide compounds).

Withanolide compounds have been demonstrated to have therapeutic properties in the treatment of proliferative disease, cardiovascular disease, neurodegenerative disease, and inflammatory disease (see e.g., U.S. Pat. No. 8,598,339, herein incorporated by reference in its entirety). Provided herein are compositions and methods employing nanoparticle formulations of withanolide compounds. As demonstrated by experiments conducted during the development of embodiments of the technology, nanoparticle formulations of withanolide compounds have unexpected and surprising efficacy (e.g., cytotoxicity) in the treatment of hyperproliferative diseases, such as cancer, in comparison to free drug. While the specification below illustrates embodiments of the technology with a focus on the treatment of hyperproliferative diseases, it should be understood that the technology may be applied to any disease or indication where a withanolide compound is efficacious.

In some embodiments, the withanolide compounds are formulated with nanoparticles comprising HDL or synthetic HDL (sHDL). These compositions, and associated methods, provide cell selectivity (e.g., cancer cell selectivity) and, as demonstrated in the Example section below, provide surprisingly efficacy treatment of cancer both in vitro and in vivo.

Cancer cells express different levels of scavenger receptor class BI (SR-BI), a receptor recognizing high density lipoprotein (HDL) nanoparticle. Adenocortical carcinoma (ACC), pancreatic, breast and many other cancers show presence of SR-BI. Yet even within the same cancer type there are high and low SR-BI expressing cell-lines, such as MDA-MB-231 (−) and MDA-MB-468in (+)—breast, RL251 (−) and H295R (+) ACC, Jurkat (−) and Ramos (+) lymphoma.

In some embodiments, provided herein are nanoparticles that target SR-BI expressing cells (e.g., cancer cells) for the treatment, prevention, and management of diseases (e.g., hyperproliferative diseases).

In some preferred embodiments, the nanoparticles comprise sHLDs based on a full-length protein (ApoA-I, ApoA-II, ApoAI-Milano and others), or synthetic ApoA-I mimetic peptides, to deliver anticancer drugs (e.g., withanolide compounds) to SR-BI expressing cells. sHDL provide safe, long-circulating and biocompatible nanoparticles that selectively target drugs to SR-BI expressing cells, alter their pharmacokinetics, improve delivery into the cell and therapeutics index.

The compositions and methods provided herein provide improved quality of care that reduces the time and failure rate of therapies, eliminates trial-and-error inefficiencies that inflate health care costs and undermine patient care, provide a higher probability of desired outcomes resulting from more effective and better-targeted therapies, and reduced probability of negative side effects.

HDLs are based on natural, endogenous nanoparticles and are biodegradable and biocompatible resulting in minimal side effects. HDLs have a small size profile (5-12 nm), long circulation half-life (15 h) and the capability of offloading its cholesterol ester content directly into the cytoplasm of cells via SR-B1. HDL-based nanoparticles do not require PEG or cationic lipid modifications for drug delivery and avoids endosomal entrapment.

This approach to drug delivery finds use in the management of cancer and other diseased states (such as diabetes, heart failure, certain cases of obesity etc.) associated with differential (over) expression of SR-B1. For example, SR-B1 is the receptor for Hepatitis C Virus entry, which makes it a viable target for inhibition using this approach. Other indications include, but are not limited to, treating a cardiovascular disease such as hypertension or ischemia; treating a neurodegenerative disease such as Parkinson's disease, Huntington's disease, or Alzheimer's disease; and treating an inflammatory disease such as arthritis or asthma. Withanolide compounds are further contemplated to find use against neoangiogenesis, autoimmune diseases, inflammatory diseases, cardiovascular diseases, neurodegenerative diseases, and protein aggregation disorders.

Withanolide Compounds

In some embodiments, the pharmaceutical compound delivered by the nanoparticle is a withaferin compound or derivative or analogue thereof. The roots of the medicinal plant *Withania somnifera* (L.) Dunal have been used in the Ayurvedic tradition of India as it possesses a variety of activities including anti-inflammatory (Anbalagan, et al. (1981) Indian J. Exp. Biol. 19:245-249), immunomodulatory (Ziauddin, et al. (1996) J. Ethnopharmacol. 50:69-76; Dhuley, et al. (1997) J. Ethnopharmacol. 58:15-20), cardioprotective (Dhuley, et al. (2000) J. Ethnopharmacol. 70:57-63), antioxidant (Dhuley, et al. (1998) J. Ethnopharmacol. 60:173-178), and antiproliferative (Jayaprakasam, et al. (2003) Life Sci. 74:125-132) activities. The primary bioactive constituents of *W. somnifera* are known as with anolides. These compounds are structurally diverse steroidal compounds with an ergosterol skeleton in which C-22 and C-26 are oxidized to form a δ-lactone (Ray, et al. (1994) Prog. Chem. Org. Nat. Prod. 63:1-106). Withaferin A, the first member of this group, was isolated from *W. somnifera* in 1965 (Lavie, et al. (1965) J. Org. Chem. 30:1774-1776).

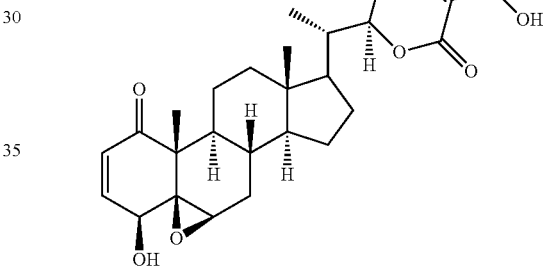

Withaferin A and related with anolides has been proposed to inhibit the actions of many targets including the actin bundling protein annexin II (Falsey, et al. (2006) Nat. Chem. Biol. 2:33-38), the 20S proteasome (Yang, et al. (2007) Mol. Pharmacol. 71:426-437), the intermediate filament protein vimentin (Bargagna-Mohan, et al. (2007) Chem. Biol. 14:623-634), the transcription factor NFkappaB (Srinivasan, et al. (2007) Cancer Res. 67:246-253), protein kinase C (Sen, et al. (2007) Cell Death Differ. 14:358-367), and the Par-4-dependent apoptosis pathway (Kaileh, et al. (2007) J. Biol. Chem. 282:4253-4264). Given its various activities, various withaferin analogs have been described. See US 2009/0088412; U.S. Pat. No. 7,282,593; WO 2010/030395; and WO 2010/053655. Each of these publications, patents, and patent applications is herein incorporated by reference in its entirety.

*Physalis longifolia* is a plant native to Kansas. *Physalis longifolia*, or longleaf groundcherry, occurs throughout the continental United States and into southern Canada. It has a characteristic husked fruit, like tomatillos and the cultivated garden plant known as Chinese lantern, which is in the same genus. These plants are part of the nightshade family, Solanaceae, which includes tomatoes, potatoes, and tobacco. *Physalis longifolia* fruit was used as a food source by southwestern Native American tribes, including the Zuni and other Puebloan people. It has been found that this plant contains a withanolide similar in structure to withaferin A (see e.g., U.S. Pat. No. 8,598,339, herein incorporated by reference in its entirety).

Withanolide compounds provided in the compositions and methods herein include, but are not limited to withaferin A, derivatives thereof, and compounds of similar structure. Such compounds include those of Formula I, II, III, IV, V, VI, VII, VIII, IX, X, XI, XII, XIII, XIV, XV, XVI or XVII, or a pharmaceutically acceptable salt or prodrug thereof.

Compounds include withanolides having the structure of Formula (I):

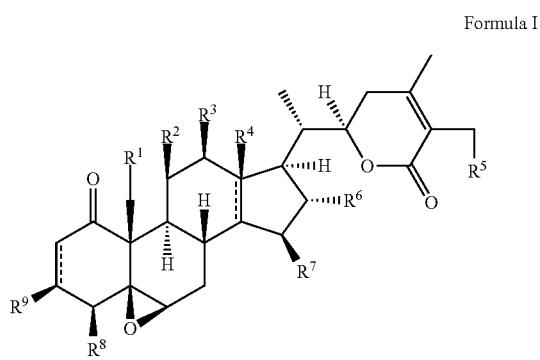

Formula I or a pharmaceutically acceptable salt or prodrug thereof, wherein $R^1$ and $R^8$ are each $—OR^B$, wherein each occurrence of $R^B$ is independently hydrogen, $—SO_3H$, $—PO_3H_2$, $—C(=O)R^C$, $—C(=O)—CH(R^C)—N(R^C)_2$, $—C(=O)N(R^C)_2$, $—CO_2R^C$, $—SOR^C$, $—SO_2R^C$, or $—C(R^C)_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group; $R^2$, $R^3$, $R^5$, $R^7$ and $R^9$ are each independently hydrogen or $—OR^D$, where each occurrence of $R^D$ is independently hydrogen, $—SO_3H$, $—PO_3H_2$, $—C(=O)R^C$, $—C(=O)N(R^C)_2$, $—CO_2R^C$, $—SOR^C$, $—SO_2R^C$ or $—C(R^C)_3$; $R^4$ is hydrogen or an alkyl group; $R^6$ is hydrogen or $—OH$; and a bond represented by parallel solid and dashed lines denotes a single or double bond.

In some embodiments, $R^1$ of Formula I is hydroxyl. In other embodiments, $R^1$ of Formula I is alkoxy. In particular embodiments, $R^1$ of Formula I is acetate.

In certain embodiments, $R^2$ of Formula I is hydrogen. In other embodiments, $R^2$ of Formula I is hydroxyl.

In some embodiments, $R^3$ of Formula I is hydrogen. In certain other embodiments, $R^3$ of Formula I is hydroxyl. In certain embodiments, $R^3$ of Formula I is alkoxy. In certain embodiments, $R^3$ of Formula I is phosphate. In certain embodiments, $R^3$ of Formula I is sulfate. In certain other embodiments, $R^3$ of Formula I is acetate.

In certain embodiments, $R^4$ of Formula I is hydrogen. In other embodiments, $R^4$ of Formula I is $—CH_3$.

In certain embodiments, $R^5$ of Formula I is hydrogen. In certain other embodiments, $R^5$ of Formula I is hydroxyl. In certain embodiments, $R^5$ of Formula I is alkoxy. In certain embodiments, $R^5$ of Formula I is phosphate. In certain embodiments, $R^5$ of Formula I is sulfate. In certain other embodiments, $R^5$ of Formula I is acetate. In other embodiments, $R^5$ of Formula I is a monosaccharide (e.g., glucopyranose). In still other embodiments, $R^5$ of Formula I is a disaccharide (e.g., lactose).

In some embodiments, $R^6$ of Formula I is hydrogen. In other embodiments, $R^6$ of Formula I is hydroxyl.

In one embodiment $R^7$ of Formula I is hydrogen. In other embodiments, $R^7$ of Formula I is hydroxyl. In certain embodiments, $R^7$ of Formula I is alkoxy. In certain embodiments, $R^7$ of Formula I is phosphate. In certain embodiments, $R^7$ of Formula I is sulfate. In certain other embodiments, $R^7$ of Formula I is acetate.

In some embodiments, $R^8$ of Formula I is hydrogen. In other embodiments, $R^8$ of Formula I is hydroxyl. In certain embodiments, $R^8$ of Formula I is alkoxy. In certain embodiments, $R^8$ of Formula I is phosphate. In certain embodiments, $R^8$ of Formula I is sulfate. In certain other embodiments, $R^8$ of Formula I is acetate.

In one embodiment $R^9$ of Formula I is hydrogen. In another embodiment, $R^9$ of Formula I is hydroxyl. In certain embodiments, $R^9$ of Formula I is sulfate. In other embodiments, $R^9$ of Formula I is a monosaccharide (e.g., glucopyranose). In certain embodiments, $R^9$ of Formula I is $—OCH_3$.

In certain embodiments, at least one of $R^1$, $R^5$ or $R^8$ of Formula I is acetate. In other embodiments, at least two of $R^1$, $R^5$ or $R^8$ of Formula I are acetate. In particular embodiments, each of $R^1$, $R^5$ and $R^8$ of Formula I is acetate.

In one embodiment, the compound of Formula I is:

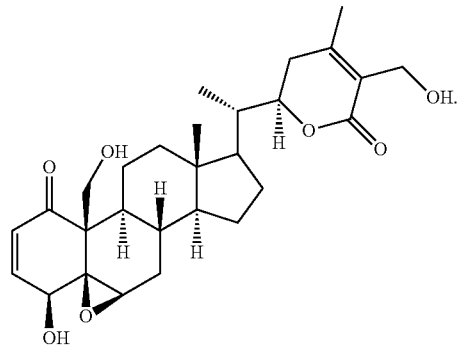

In another embodiment, the compound of Formula I is:

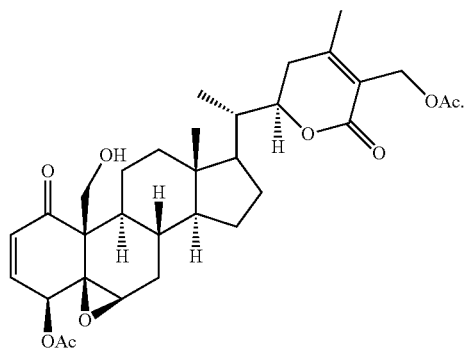

In a further embodiment, the compound of Formula I is (4, 19, 27-triacetyl withalongolide A):

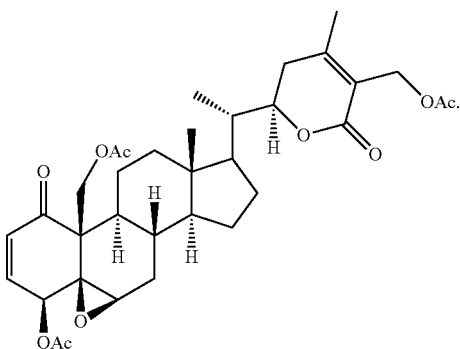

In certain embodiments, provided herein is a compound of Formula II:

Formula II

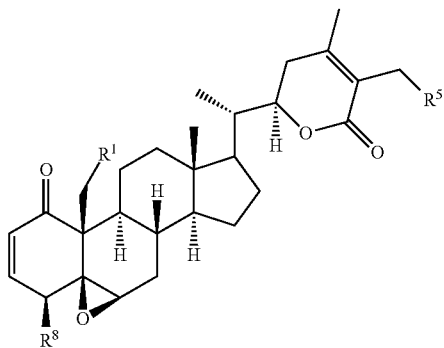

or a pharmaceutically acceptable salt or prodrug thereof, wherein $R^1$ and $R^8$ are each —$OR^B$, wherein each occurrence of $R^B$ is independently hydrogen, —$SO_3H$, —$PO_3H_2$, —$C(=O)R^C$, —$C(=O)N(R^C)_2$, —$CO_2R^C$, —$SOR^C$, —$SO_2R^C$, or —$C(R^C)$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group; $R^5$ is hydrogen or —$OR^D$, where $R^D$ is hydrogen, —$SO_3H$, —$PO_3H_2$, —$C(=O)R^C$, —$C(=O)N(R^C)_2$, —$CO_2R^C$, —$SOR^C$, —$SO_2R^C$ or —$C(R^C)_3$.

In some embodiments, $R^1$ of Formula II is hydroxyl. In other embodiment, $R^1$ of Formula II is alkoxy. In particular embodiments, $R^1$ of Formula II is acetate.

In certain embodiments, $R^5$ of Formula II is hydrogen. In certain other embodiments, $R^5$ of Formula II is hydroxyl. In certain embodiments, $R^5$ of Formula II is alkoxy. In certain embodiments, $R^5$ of Formula II is phosphate. In certain embodiments, $R^5$ of Formula II is sulfate.

In certain other embodiments, $R^5$ of Formula II is acetate. In other embodiments, $R^5$ of Formula II is a monosaccharide (e.g., glucopyranose). In still other embodiments, $R^5$ of Formula II is a disaccharide (e.g., lactose).

In some embodiments, $R^8$ of Formula II is hydrogen. In other embodiments, $R^8$ of Formula II is hydroxyl. In certain embodiments, $R^8$ of Formula II is alkoxy. In certain embodiments, $R^8$ of Formula II is phosphate. In certain embodiments, $R^8$ of Formula II is sulfate. In certain other embodiments, $R^8$ of Formula II is acetate.

In certain embodiments, at least one of $R^1$, $R^5$ or $R^8$ of Formula II is acetate. In other embodiments, at least two of $R^1$, $R^5$ or $R^8$ of Formula II are acetate. In particular embodiments, each of $R^1$, $R^5$ and $R^8$ of Formula II is acetate.

In other embodiments, provided herein is a compound of Formula III:

Formula III

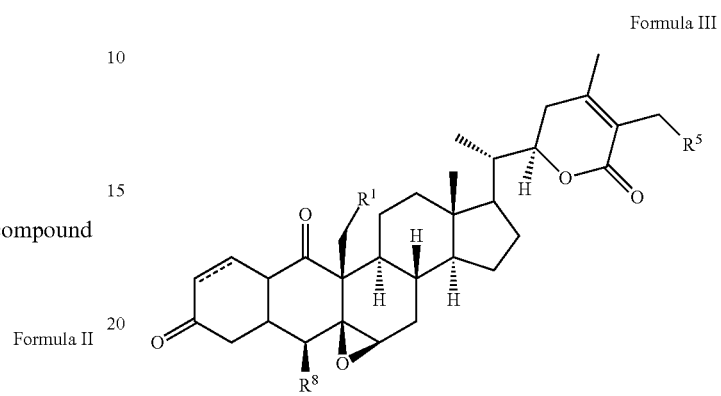

or a pharmaceutically acceptable salt or prodrug thereof, wherein
$R^1$ and $R^8$ are each —$OR^B$, wherein each occurrence of $R^B$ is independently hydrogen, —$SO_3H$, —$PO_3H_2$, —$C(=O)R^C$, —$C(=O)$—$CH(R^C)$—$N(R^C)_2$, —$C(=O)N(R^C)_2$, —$CO_2R^C$, —$SOR^C$, —$SO_2R^C$, or —$C(R^C)_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group; $R^5$ is hydrogen or —$OR^D$, where $R^D$ is hydrogen, —$SO_3H$, —$PO_3H_2$, —$C(=O)R^C$, $C(=O)N(R^C)_2$, —$CO_2R^C$, —$SOR^C$, —$SO_2R^C$ or —$C(R^C)_3$; and
$\equiv\equiv\equiv$ denotes a single or double bond.

In another embodiment, provided herein is a compound of Formula IV:

Formula IV

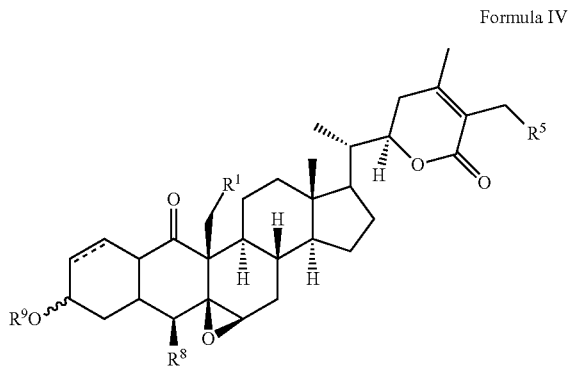

or a pharmaceutically acceptable salt or prodrug thereof, wherein
$R^1$ and $R^8$ are each —$OR^B$, wherein each occurrence of $R^B$ is independently hydrogen, —$SO_3H$, —$PO_3H_2$, —$C(=O)R^C$, —$CH(R^C)$—$N(R^C)_2$, —$C(=O)N(R^C)_2$, —$CO_2R^C$, —$SOR^C$, —$SO_2R^C$, or —$C(R^C)_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group; $R^5$ and $R^9$ are each independently hydrogen or —$OR^D$, where each occurrence of $R^D$ is independently hydrogen, —$SO_3H$, —$PO_3H_2$, —$C(=O)R^C$, —$C(=O)N(R^C)_2$, —$CO_2R^C$, —$SOR^C$, —$SO_2R^C$ or —$C(R^C)_3$;

═ denotes a single or double bond; and

∿ denotes either a ▎ (β-stereochemistry) or ⁞ (α-stereochemistry).

In still other embodiments, provided herein is a compound of Formula V:

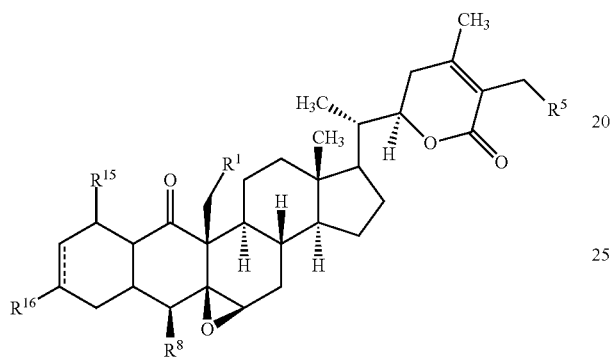

Formula V or a pharmaceutically acceptable salt or prodrug thereof, wherein $R^1$ and $R^8$ are each —$OR^B$, wherein each occurrence of $R^B$ is independently hydrogen, —$SO_3H$, —$PO_3H_2$, —$C(=O)R^C$, —$C(=O)—CH(R^C)—N(R^C)_2$, —$C(=O)N(R^C)_2$, —$CO_2R^C$, —$SOR^C$, —$SO_2R^C$, or —$C(R^C)_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group; $R^5$ is hydrogen or —$OR^D$, where $R^D$ is hydrogen, —$SO_3H$, —$PO_3H_2$, —$C(=O)R^C$, —$C(=O)N(R^C)_2$, —$CO_2R^C$, —$SOR^C$, —$SO_2R^C$ or —$C(R^C)_3$; $R^{15}$ and $R^{16}$ are each independently —$OR^E$, where each occurrence of $R^E$ is independently a hydrogen, aliphatic group, aryl group, or —$SiR^C$, wherein $R^C$ is as defined above; and ═ denotes a single or double bond.

In yet other embodiments, provided herein is a compound of Formula VI:

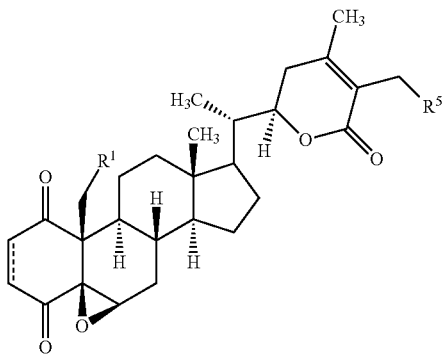

Formula VI or a pharmaceutically acceptable salt or prodrug thereof, wherein $R^1$ is —$OR^B$, wherein $R^B$ is hydrogen, —$SO_3H$, —$PO_3H_2$, —$C(=O)R^C$, —$C(=O)—CH(R^C)—N(R^C)_2$, —$C(=O)N(R^C)_2$, —$CO_2R^C$, —$SOR^C$, —$SO_2R^C$, or —$C(R^C)_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group; $R^5$ is hydrogen or —$OR^D$, where $R^D$ is hydrogen, —$SO_3H$, —$PO_3H_2$, —$C(=O)R^C$, —$C(=O)N(R^C)_2$, —$CO_2R^C$, —$SOR^C$, —$SO_2R^C$ or —$C(R^C)_3$; and ═ denotes a single or double bond.

In further embodiments, provided herein is a compound of Formula VII:

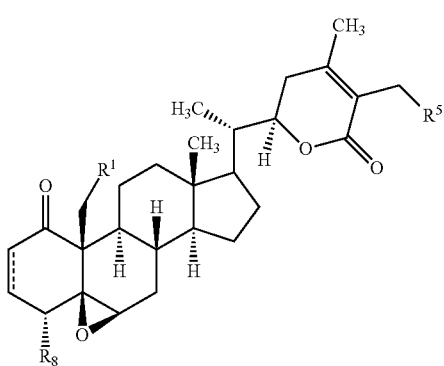

Formula VII or a pharmaceutically acceptable salt or prodrug thereof, wherein $R^1$ and $R^8$ are each —$OR^B$, wherein each occurrence of $R^B$ is independently hydrogen, —$SO_3H$, —$PO_3H_2$, —$C(=O)R^C$, —$C(=O)—CH(R^C)—N(R^C)_2$, —$C(=O)N(R^C)_2$, —$CO_2R^C$, —$SOR^C$, —$SO_2R^C$, or —$C(R^C)_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group;

$R^5$ is hydrogen or —$OR^D$, where $R^D$ is hydrogen, —$SO_3H$, —$PO_3H_2$, —$C(=O)R^C$, —$C(=O)N(R^C)_2$, —$CO_2R^C$, —$SOR^C$, —$SO_2R^C$ or —$C(R^C)_3$; and ═ denotes a single or double bond.

Provided herein is a compound of Formula VIII:

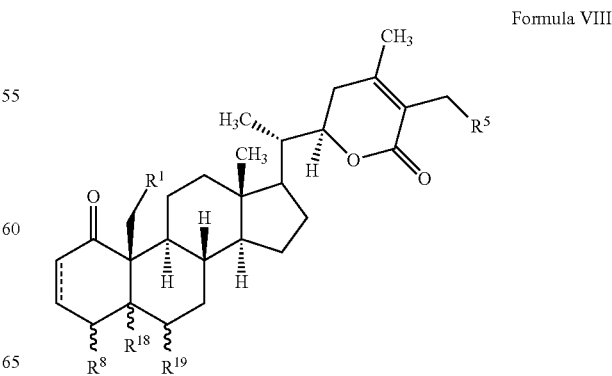

Formula VIII or a pharmaceutically acceptable salt or prodrug thereof, wherein
$R^1$ and $R^8$ are each —$OR^B$, wherein each occurrence of $R^B$ is independently hydrogen, —$SO_3H$, —$PO_3H_2$, —$C(=O)R^C$, —$C(=O)$—$CH(R^C)$—$N(R^C)_2$, —$C(=O)N(R^C)_2$, —$CO_2R^C$, —$SOR^C$, —$SO_2R^C$, or —$C(R^C)_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group;
$R^5$ is hydrogen or —$OR^D$, where $R^D$ is hydrogen, —$SO_3H$, —$PO_3H_2$, —$C(=O)R^C$, —$C(=O)N(R^C)_2$, —$CO_2R^C$, —$SOR^C$, —$SO_2R$ or —$C(R^C)_3$;
$R^{18}$ and $R^{19}$ are each independently $R^H$ or —$OR^B$ as defined above, where $R^{20}$ is a halogen, alkyl group, alkenyl group (vinyl, propenyl, or allyl), aryl group, carboxylic acid group, amino group, alkylamino group, dialkylamino group, cyano group, azido group, hydroxylamino group, O-alkylhydroxylamino group;
═══ denotes a single or double bond; and
∿∿ denotes either a ⫯ (β-stereochemistry) or ⫰ (α-stereochemistry).

Provided herein is a compound of Formula IX:

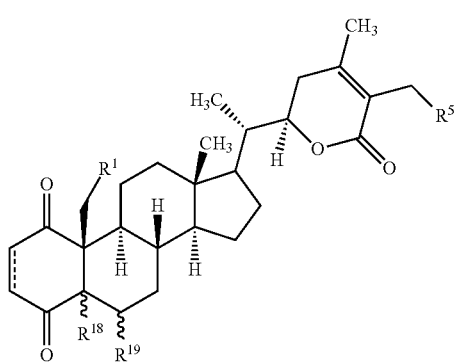

Formula IX or a pharmaceutically acceptable salt or prodrug thereof, wherein
$R^1$ is —$OR^B$, wherein $R^B$ is hydrogen, —$SO_3H$, —$PO_3H_2$, —$C(=O)R^C$, —$C(=O)$—$CH(R^C)$—$N(R^C)_2$, —$C(=O)N(R^C)_2$, —$CO_2R^C$, —$SOR^C$, —$SO_2R^C$, or —$C(R^C)_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group; $R^5$ is hydrogen or —$OR^D$, where $R^D$ is hydrogen, —$SO_3H$, —$PO_3H_2$, —$C(=O)R^C$, —$C(=O)N(R^C)_2$, —$CO_2R^C$, —$SOR^C$, $SO_2R^C$ or —$C(R^C)_3$;
$R^{18}$ and $R^{19}$ are each independently $R^{20}$ or —$OR^B$ as defined above, where $R^{20}$ is independently a halogen, alkyl group, alkenyl group (vinyl, propenyl, or allyl), aryl group, carboxylic acid group, amino group, alkylamino group, dialkylamino group, cyano group, azido group, hydroxylamino group, O-alkylhydroxylamino group; and
═══ denotes a single or double bond; and
∿∿ denotes either a ⫯ (β-stereochemistry) or ⫰ (α-stereochemistry).

A compound of Formula X is also included herein:

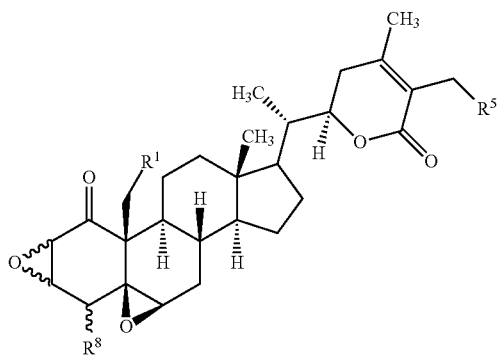

Formula X or a pharmaceutically acceptable salt or prodrug thereof, wherein
$R^1$ and $R^8$ are each —$OR^B$, wherein each occurrence of $R^B$ is independently hydrogen, —$SO_3H$, —$PO_3H_2$, —$C(=O)R^C$, —$C(=O)$—$CH(R^C)$—$N(R^C)_2$, —$C(=O)N(R^C)_2$, —$CO_2R^C$, —$SOR^C$, —$SO_2R^C$, or —$C(R^C)_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group;
$R^5$ is hydrogen or —$OR^D$, where $R^D$ is hydrogen, —$SO_3H$, —$PO_3H_2$, —$C(=O)R^C$, —$C(=O)N(R^C)_2$, —$CO_2R^C$, —$SOR^C$, —$SO_2R^C$ or —$C(R^C)_3$; and
∿∿ denotes either a ⫯ (β-stereochemistry) or ⫰ (α-stereochemistry).

A compound Formula XI is also provided:

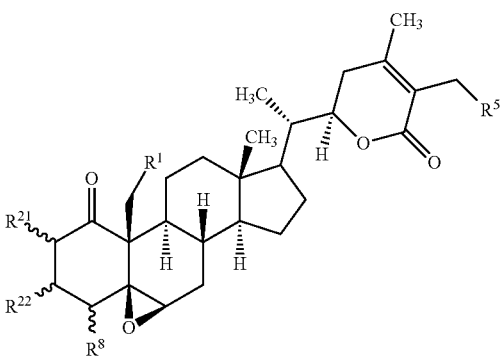

Formula XI or a pharmaceutically acceptable salt or prodrug thereof, wherein
$R^1$, $R^8$, $R^{21}$ and $R^{22}$ are each —$OR^B$, wherein each occurrence of $R^B$ is independently hydrogen, —$SO_3H$, —$PO_3H_2$, —$C(=O)R^C$, —$C(=O)$—$CH(R)$—$N(R^C)_2$, —$C(=O)N(R^C)_2$, —$CO_2R^C$, —$SOR^C$, —$SO_2R^C$, or —$C(R^C)$ wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group;

$R^5$ is hydrogen or —$OR^D$, where $R^D$ is hydrogen, —$SO_3H$, —$PO_3H_2$, —C(=O)$R^C$, C(=O)N($R^C$)$_2$, —$CO_2R^C$, —$SOR^C$, —$SO_2R^C$ or —C($R^C$)$_3$; and ∽ denotes either a ∤ (β-stereochemistry) or ⁞ (α-stereochemistry).

A compound of Formula XII is also included herein:

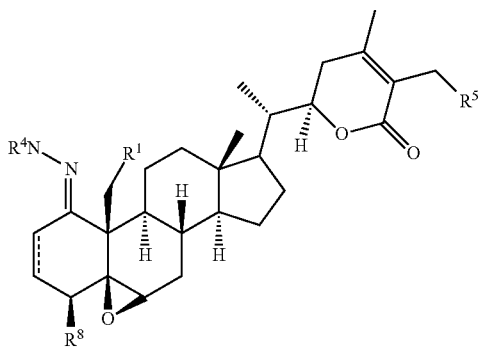

Formula XII or a pharmaceutically acceptable salt or prodrug thereof, wherein $R^1$ and $R^8$ are each —$OR^B$, wherein each occurrence of $R^B$ is independently hydrogen, —$SO_3H$, —$PO_3H_2$, —C(=O)$R^C$, —C(=O)—CH($R^C$)—N($R^C$)$_2$, —C(=O)N($R^C$)$_2$, —$CO_2R^C$, —$SOR^C$, —$SO_2R^C$, or —C($R^C$)$_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group;

$R^4$ is hydrogen or an alkyl group;

$R^5$ is hydrogen or —$OR^D$, where $R^D$ is hydrogen, —$SO_3H$, —$PO_3H_2$, —C(=O)R, —C(=O)N($R^C$)$_2$, —$CO_2R^C$, —$SOR^C$, —$SO_2R^C$ or —C($R^C$)$_3$; and ⁓ denotes a single or double bond.

A compound of Formula XIII is also included herein:

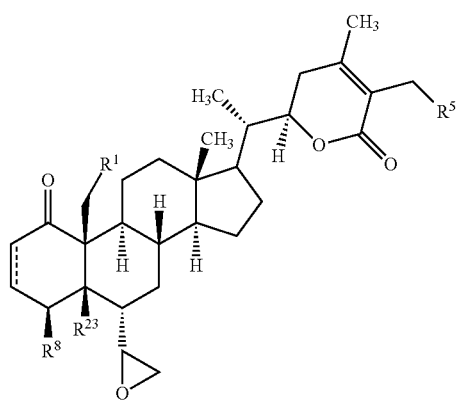

Formula XIII or a pharmaceutically acceptable salt or prodrug thereof, wherein $R^1$, $R^8$ and $R^{23}$ are each —$OR^B$, wherein each occurrence of $R^B$ is independently hydrogen, —$SO_3H$, —$PO_3H_2$, —C(=O)$R^C$, —C(=O)—CH($R^C$)—N($R^C$)$_2$, —C(=O)N($R^C$)$_2$, —$CO_2R^C$, —$SOR^C$, —$SO_2R^C$, or —C($R^C$)$_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group;

$R^5$ is hydrogen or —$OR^D$, where $R^D$ is hydrogen, —$SO_3H$, —$PO_3H_2$, —C(=O)$R^C$, —C(=O)N($R^C$)$_2$, —$CO_2R^C$, —$SOR^C$, —$SO_2R^C$ or —C($R^C$)$_3$; and ⁓ denotes a single or double bond.

In particular embodiments, provided herein is a compound of Formula XIV:

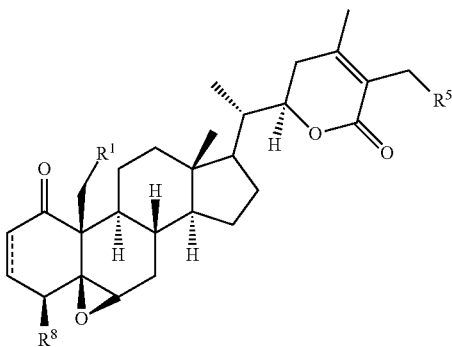

Formula XIV or a pharmaceutically acceptable salt or prodrug thereof, wherein $R^1$ and $R^8$ are each independently —CHO, —COOH, or COO$R^4$, wherein $R^4$ is hydrogen or an alkyl group;

$R^5$ is hydrogen or —$OR^D$, where $R^D$ is hydrogen, —$SO_3H$, —$PO_3H_2$, —C(=O)$R^C$, —C(=O)N($R^C$)$_2$, —$CO_2R^C$, —$SOR^C$, —$SO_2R^C$ or —C($R^C$)$_3$; and ⁓ denotes a single or double bond.

In a further embodiment, provided herein is a compound of Formula XV:

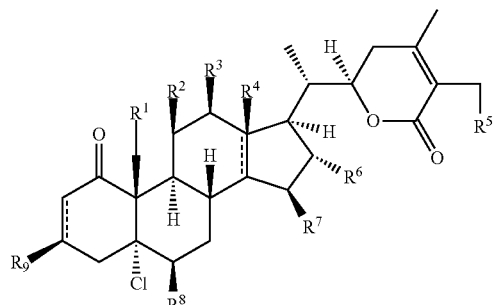

Formula XV or a pharmaceutically acceptable salt or prodrug thereof, wherein $R^1$ and $R^8$ are each —$OR^B$, wherein each occurrence of $R^B$ is independently hydrogen, —$SO_3H$, —$PO_3H_2$, —C(=O)$R^C$, —C(=O)—CH($R^C$)—N($R^C$)$_2$, —C(=O)N($R^C$)$_2$, —$CO_2R^C$, —$SOR^C$, —$SO_2R^C$, or —C($R^C$)$_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group;

$R^2$, $R^3$, $R^5$, $R^7$ and $R^9$ are each independently hydrogen or —$OR^D$, where each occurrence of $R^D$ is independently hydrogen, —$SO_3H$, —$PO_3H_2$, —$C(=O)R^C$, —$C(=O)N(R^C)_2$, —$CO_2R^C$, —$SOR^C$, —$SO_2R^C$ or —$C(R^C)_3$;
$R^4$ is hydrogen or an alkyl group;
$R^6$ is hydrogen or —OH; and
═══ denotes a single or double bond.

In a particular embodiment, provided herein is a compound of Formula XVI:

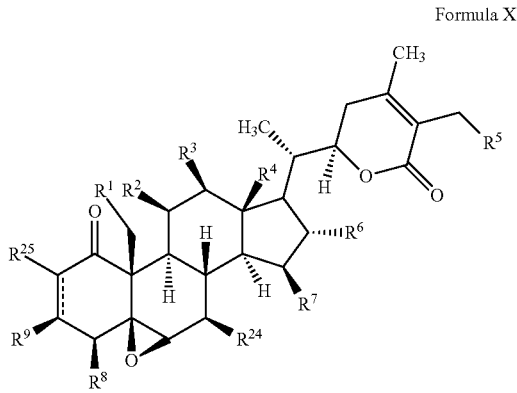

Formula XVI or a pharmaceutically acceptable salt or prodrug thereof, wherein
$R^1$ and $R^8$ are each —$OR^B$, wherein each occurrence of $R^B$ is independently hydrogen, —$SO_3H$, —$PO_3H_2$, —$C(=O)R^C$, —$C(=O)$—$CH(R^C)$—$N(R^C)_2$, —$C(=O)N(R^C)_2$, —$CO_2R^C$, —$SOR^C$, —$SO_2R^C$, or —$C(R^C)_3$, wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group;
$R^2$, $R^3$, $R^5$, $R^7$ and $R^9$ are each independently hydrogen or —$OR^D$, where each occurrence of $R^D$ is independently hydrogen, —$SO_3H$, —$PO_3H_2$, —$C(=O)R^C$, —$C(=O)N(R^C)_2$, —$CO_2R^C$, —$SOR^C$, —$SO_2R^C$ or —$C(R^C)_3$;
$R^4$ is hydrogen or an alkyl group;
$R^6$ is hydrogen or —OH;
$R^{24}$ is —OH or —OAc;
$R^{25}$ is I, aryl, or heteroaryl; and
═══ denotes a single or double bond.

In yet a further embodiment, provided herein is a compound of Formula XVII:

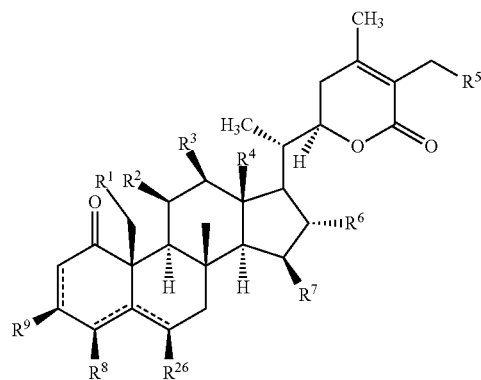

Formula XVII or a pharmaceutically acceptable salt or prodrug thereof, wherein
$R^1$ is —$OR^B$, wherein $R^B$ is hydrogen, —$SO_3H$, —$PO_3H_2$, —$C(=O)R^C$, —$C(=O)$—$CH(R^C)$—$N(R^C)_2$, —$C(=O)N(R^C)_2$, —$CO_2R^C$, —$SOR^C$, —$SO_2R^C$, or —$C(R^C)$ wherein each occurrence of $R^C$ is independently a hydrogen, a halogen, an aliphatic group, a heteroaliphatic group, an acyl group, an aryl group, a heteroaryl group, alkoxy group, aryloxy group, alkylthio group, arylthio group, amino group, alkylamino group, dialkylamino group, heteroaryloxy, peptide, or heteroarylthio group; $R^2$, $R^3$, $R^5$ and $R^7$ are each independently hydrogen or —$OR^D$, where each occurrence of $R^D$ is independently hydrogen, —$SO_3H$, $PO_3H_2$, —$C(=O)R^C$, —$C(=O)N(R)_2$, —$CO_2R^C$, —$SOR^C$, —$SO_2R^C$ or —$C(R^C)_3$;
$R^4$ is hydrogen or an alkyl group;
$R^6$ is hydrogen or —OH;
$R^8$ and $R^9$ are hydrogen;
$R^{26}$ is —OH or —OAc; and
═══ denotes a single or double bond.

It will be appreciated that the compounds as described herein may be substituted with any number of substituents or functional moieties. In general, the term "substituted," whether preceded by the term "optionally" or not, and substituents contained in formulas, refer to the replacement of hydrogen in a given structure with a specified substituent. When more than one position in any given structure may be substituted with more than one substituent selected from a specified group, the substituent may be either the same or different at every position. As used herein, the term "substituted" is contemplated to include substitution with all permissible substituents of organic compounds, any of the substituents described herein (for example, aliphatic, alkyl, alkenyl, alkynyl, heteroaliphatic, heterocyclic, aryl, heteroaryl, acyl, oxo, imino, thioxo, cyano, isocyano, amino, azido, nitro, hydroxyl, thiol, halo, etc.), and any combination thereof (for example, aliphaticamino, heteroaliphaticamino, alkylamino, heteroalkylamino, acylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like) that results in the formation of a stable moiety. Any and all such combinations are contemplated in order to arrive at a stable substituent/moiety. For purposes of this description, heteroatoms such as nitrogen may have hydrogen substituents and/or any suitable substituent as described herein which satisfy the valencies of the heteroatoms and results in the formation of a stable moiety. The term "stable moiety," as used herein, preferably refers to a moiety which possess stability sufficient to allow manufacture, and which maintains its integrity for a sufficient period of time to be useful for the purposes detailed herein.

As used herein, substituent names which end in the suffix "-ene" refer to a biradical derived from the removal of two hydrogen atoms from the substituent. Thus, for example, acyl is acylene; alkyl is alkylene; alkeneyl is alkenylene; alkynyl is alkynylene; heteroalkyl is heteroalkylene, heteroalkenyl is heteroalkenylene, heteroalkynyl is heteroalkynylene, aryl is arylene, and heteroaryl is heteroarylene.

With particular reference to the compounds herein, the term "acyl," as used herein, refers to a group having the general formula —$C(=O)R^F$, —$C(=O)OR^F$, —$C(=O)$—$O$—$C(=O)R^F$, —$C(=O)SR^F$, —$C(=O)N(R^F)_2$, wherein $R^F$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^F$ groups taken together form a 5- to 6-membered heterocyclic ring. Exemplary acyl groups include aldehydes (—CHO), carboxylic acids (—$CO_2H$), ketones, acyl esters, amides, imines, carbonates, carbamates, and ureas. Acyl substituents include, but are not limited to, any of the substituents described herein, that result in the formation of a stable moiety.

The term "acyloxy" refers to a "substituted hydroxyl" of the formula (—$OR^G$), wherein $R^G$ is an optionally substituted acyl group, as defined herein, and the oxygen moiety is directly attached to the parent molecule.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein.

The term "alkyl," refers to saturated, straight- or branched-chain hydrocarbon radicals derived from a hydrocarbon moiety containing between one and twenty carbon atoms by removal of a single hydrogen atom. In some embodiments, the alkyl group employed contains 1-20 carbon atoms. In another embodiment, the alkyl group employed contains 1-15 carbon atoms. In another embodiment, the alkyl group employed contains 1-10 carbon atoms. In another embodiment, the alkyl group employed contains 1-8 carbon atoms. In another embodiment, the alkyl group employed contains 1-5 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents. Alkyl group substituents include, but are not limited to, any of the substituents described herein.

The term "alkenyl," denotes a monovalent group derived from a straight- or branched-chain hydrocarbon moiety having at least one carbon-carbon double bond by the removal of a single hydrogen atom. In certain embodiments, the alkenyl group employed contains 2-20 carbon atoms. In some embodiments, the alkenyl group employed contains 2-15 carbon atoms. In another embodiment, the alkenyl group employed contains 2-carbon atoms. In still other embodiments, the alkenyl group contains 2-8 carbon atoms. In yet other embodiments, the alkenyl group contains 2-5 carbons. Alkenyl groups include, for example, ethenyl, propenyl, butenyl, 1-methyl-2-buten-1-yl, and the like, which may bear one or more substituents. Alkenyl group substituents include, but are not limited to, any of the substituents described herein.

The term "alkynyl," refers to a monovalent group derived from a straight- or branched-chain hydrocarbon having at least one carbon-carbon triple bond by the removal of a single hydrogen atom. In certain embodiments, the alkynyl group employed contains 2-20 carbon atoms. In some embodiments, the alkynyl group employed contains 2-15 carbon atoms. In another embodiment, the alkynyl group employed contains 2-carbon atoms. In still other embodiments, the alkynyl group contains 2-8 carbon atoms. In still other embodiments, the alkynyl group contains 2-5 carbon atoms.

Representative alkynyl groups include, but are not limited to, ethynyl, 2-propynyl(propargyl), 1-propynyl, and the like, which may bear one or more substituents. Alkynyl group substituents include, but are not limited to, any of the substituents described herein.

The term "amino," refers to a group of the formula (—$NH_2$). A "substituted amino" refers either to a mono-substituted amine (—$NHR^H$) or a disubstituted amine (—$NR^H_2$), wherein the $R^H$ substituent is, independently, a hydrogen or an optionally substituted alkyl group, as defined herein. In certain embodiments, the $R^H$ substituents of the di-substituted amino group (—$NR^H_2$) are converted to form a 5- to 6-membered heterocyclic ring.

The term "alkoxy" refers to a "substituted hydroxyl" of the formula (—$OR^1$), wherein $R^1$ is an optionally substituted alkyl group, as defined herein, and the oxygen moiety is directly attached to the parent molecule.

The term "alkylthioxy" refers to a "substituted thiol" of the formula (—$SR^J$), wherein $R^J$ is an optionally substituted alkyl group, as defined herein, and the sulfur moiety is directly attached to the parent molecule.

The term "alkylamino" refers to a "substituted amino" of the formula (—$NR^K_2$), wherein $R^K$ is, independently, a hydrogen or an optionally substituted alkyl group, as defined herein, and the nitrogen moiety is directly attached to the parent molecule.

The term "aryl" refers to stable aromatic mono- or polycyclic ring systems having 3-20 ring atoms, of which all the ring atoms are carbon, and which may be substituted or unsubstituted. In certain embodiments, "aryl" refers to a mono, bi, or tricyclic $C_4$-$C_{20}$ aromatic ring system having one, two, or three aromatic rings which include, but not limited to, phenyl, biphenyl, naphthyl, and the like, which may bear one or more substituents.

The term "arylalkyl," as used herein, refers to an aryl substituted alkyl group, wherein the terms "aryl" and "alkyl" are defined herein, and wherein the aryl group is attached to the alkyl group, which in turn is attached to the parent molecule. An exemplary arylalkyl group includes benzyl.

The term "aryloxy" refers to a "substituted hydroxyl" of the formula (—$OR^L$), wherein $R^L$ is an optionally substituted aryl group, as defined herein, and the oxygen moiety is directly attached to the parent molecule.

The term "arylamino" refers to a "substituted amino" of the formula (—$NR^M_2$), wherein $R^M$ is, independently, a hydrogen or an optionally substituted aryl group, as defined herein, and the nitrogen moiety is directly attached to the parent molecule.

The term "arylthioxy" refers to a "substituted thiol" of the formula (—$SR^N$), wherein $R^N$ is an optionally substituted aryl group, as defined herein, and the sulfur moiety is directly attached to the parent molecule.

The term "azido," as used herein, refers to a group of the formula (—$N_3$).

The term "cyano," as used herein, refers to a group of the formula (—CN).

The terms "halo" and "halogen" refer to an atom selected from fluorine (fluoro, —F), chlorine (chloro, —Cl), bromine (bromo, —Br), and iodine (iodo, —I).

The term "heteroaliphatic" refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl groups. Thus, the term "heteroaliphatic" includes the terms "heteroalkyl," "heteroalkenyl," "heteroalkynyl" and the like. Furthermore, as used herein, the terms "heteroalkyl," "heteroalkenyl," "heteroalkynyl" and the like encompass both substituted and unsubstituted groups. In certain embodiments, "heteroaliphatic" is used to indicate those heteroaliphatic groups (cyclic, acyclic, substituted, unsubstituted, branched or unbranched) having 1-20 carbon atoms. The terms "heteroalkyl," "heteroalkenyl" and "heteroalkynyl" respectively refer to an alkyl, alkenyl and alkynyl groups, as defined herein, which contain one or more oxygen, sulfur, nitrogen, phosphorus, or silicon atoms, e.g., in place of carbon atoms.

The term "heteroalkylamino" refers to a "substituted amino" of the formula (—$NR^O_2$), wherein $R^O$ is, independently, a hydrogen or an optionally substituted heteroalkyl group, as defined herein, and the nitrogen moiety is directly attached to the parent molecule.

The term "heteroalkyloxy" refers to a "substituted hydroxyl" of the formula (—$OR^P$), wherein $R^P$ is an optionally substituted heteroalkyl group, as defined herein, and the oxygen moiety is directly attached to the parent molecule.

The term "heteroalkylthioxy" refers to a "substituted thiol" of the formula (—$SR^Q$), wherein $R^Q$ is an optionally substituted heteroalkyl group, as defined herein, and the sulfur moiety is directly attached to the parent molecule.

The term "heterocyclic," "heterocycles," or "heterocyclyl" refers to a cyclic heteroaliphatic group. A heterocyclic group refers to a non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents as described herein.

The term "heteroaryl" refers to stable aromatic mono- or polycyclic ring systems having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyrrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents as described herein.

The term "heteroarylene" refers to a biradical derived from an heteroaryl group, as defined herein, by removal of two hydrogen atoms. Heteroarylene groups may be substituted or unsubstituted. Additionally, heteroarylene groups may be incorporated as a linker group into an alkylene, alkenylene, alkynylene, heteroalkylene, heteroalkenylene, or heteroalkynylene group, as defined herein. Heteroarylene group substituents include, but are not limited to, any of the substituents described herein.

The term "heteroarylamino" refers to a "substituted amino" of the (—$NR^R_2$), wherein RR is, independently, a hydrogen or an optionally substituted heteroaryl group, as defined herein, and the nitrogen moiety is directly attached to the parent molecule.

The term "heteroaryloxy" refers to a "substituted hydroxyl" of the formula (—$OR^S$), wherein $R^S$ is an optionally substituted heteroaryl group, as defined herein, and the oxygen moiety is directly attached to the parent molecule.

The term "heteroarylthioxy" refers to a "substituted thiol" of the formula (—$SR^T$), wherein $R^T$ is an optionally substituted heteroaryl group, as defined herein, and the sulfur moiety is directly attached to the parent molecule.

The term "hydroxy" or "hydroxyl" refers to a group of the formula (—OH). A "substituted hydroxyl" refers to a group of the formula (—$OR^U$), wherein $R^U$ can include, but is not limited to, aliphatic, alkyl, alkenyl, alkynyl, heteroaliphatic, heterocyclic, aryl, heteroaryl, acyl, nitro, alkylaryl, and arylalkyl groups, each of which may or may not be further substituted.

The term "imino" refers to a group of the formula (=NR$^V$), wherein R$^V$ corresponds to hydrogen or any substitutent, including, e.g., aliphatic, alkyl, alkenyl, alkynyl, heteroaliphatic, heterocyclic, aryl, heteroaryl, acyl, amino, hydroxyl, alkylaryl, arylalkyl, and the like, each of which may or may not be further substituted. In certain embodiments, imino refers to =NH.

The term "isocyano" refers to a group of the formula (—NC). The term "nitro" refers to a group of the formula (—NO$_2$). The term "oxo" refers to a group of the formula (=O).

A withanolide compound can be isolated from *P. longifolia*, produced semi-synthetically from natural products of *P. longifolia*, or wholly synthetically produced. When isolated from *P. longifolia*, desirably the compound is isolated from the aerial tissue and/or roots of *P. longifolia*. Aerial tissues of *P. longifolia* can be extracted with a solvent to give the crude natural product extract. In certain embodiments, the solvent includes an alcohol such as methanol. In another embodiment, the solvent includes dichloromethane. In particular embodiments, the solvent is a mixture of methanol and dichloromethane.

In certain embodiments, the crude natural product extract obtained from *P. longifolia* is purified. In certain embodiments, the extract is purified by chromatography. In certain embodiments, the extract is purified by silica gel chromatography. In certain embodiments, the crude extract is purified by successive rounds of chromatography. HPLC may be used to purify the desired compounds. The desired natural product can optionally be further purified by crystallization. The purified compounds may be characterized by various analytical methods including elemental analysis, mass spectrometry, IR, UV/vis, NMR, and x-ray crystallography. Desirably, the compound is purified to homogeneity (100%) or near homogeneity (90 to 95%).

Nanoparticles

In some embodiments, the compositions and methods herein comprise a nanoparticle-associated compound (e.g., anticancer compound such as a withanolide compound). In some embodiments, the nanoparticle is a synthetic high-density lipoprotein (HDL) nanoparticle (sHDL nanoparticle).

HDL is a small, dense lipoprotein particle, containing a high proportion of protein to lipids. Its most abundant apolipoproteins are apo A-I and apo A-II. The liver synthesizes these lipoproteins as complexes of apolipoproteins and phospholipid, which resemble cholesterol-free flattened spherical lipoprotein particles. The complexes are capable of picking up cholesterol, carried internally, from cells by interaction with the ATP-binding cassette transporter A1 (ABCA1). A plasma enzyme called lecithin-cholesterol acyltransferase (LCAT) converts the free cholesterol into cholesteryl ester (a more hydrophobic form of cholesterol), which is then sequestered into the core of the lipoprotein particle, eventually causing the newly synthesized HDL to assume a spherical shape. HDL particles increase in size as they circulate through the bloodstream and incorporate more cholesterol and phospholipid molecules from cells and other lipoproteins, for example by the interaction with the ABCG1 transporter and the phospholipid transport protein (PLTP).

Synthetic HDLs are synthetic lipoprotein particles made to mimic natural HDL. They differ from natural HDLs, for example, by the use of synthetic peptides that mimic various functions of Apolipoprotein A-I, the main protein component of HDL. The synthetic peptide Apo A-I mimics are referred to herein as "ApoA-I agonists."

The ApoA-I agonists mimic ApoA-I function and activity. For example, have one or more of the ApoA-I function or activities of: forming amphipathic helices (in the presence of lipids), binding lipids, forming pre-β-like or HDL-like complexes, activating LCAT, increasing serum HDL concentration, and promoting cholesterol efflux. The biological function of the peptides correlates with their helical structure, or conversion to helical structures in the presence of lipids.

The ApoA-I agonists can be prepared in stable bulk or unit dosage forms, e.g., lyophilized products, that can be reconstituted before use.

In some embodiments, the nanoparticle into which a withanolide compound is introduced is one or more of the nanoparticles described in U.S. 20060252694, U.S. Pat. No. 6,753,313, and/or U.S. 20030008827, each of which is herein incorporated by reference in its entirety. In preferred embodiments, the nanoparticle comprises a synthetic ApoA-I agonist.

The ApoA-I agonists are generally peptides, or analogues thereof, which are capable of forming amphipathic α-helices in the presence of lipids and which mimic the activity of ApoA-I. The agonists have as their main feature a "core" peptide composed of 15 to 29 amino acid residues, preferably 22 amino acid residues, or an analogue thereof wherein at least one amide linkage in the peptide is replaced with a substituted amide, an isostere of an amide or an amide mimetic.

In some embodiments, the ApoA-I agonists are based, in part, on altering certain amino acid residues in the primary sequence of the 22-mer consensus sequence of Venkatachalapathi et al., 1991, Mol. Conformation and Biol. Interactions, Indian Acad. Sci. B:585-596 (PVLDEFREKLNEELEALKQKLK; SEQ ID NO: 1; hereinafter "consensus 22-mer") (see e.g., US 2006252694, herein incorporated by reference in its entirety). This approach yields synthetic peptides that exhibit activities that approach, or in some cases exceed, the activity of native ApoA-I. In particular, replacing three charged amino acid residues in the consensus 22-mer peptide (Glu-5, Lys-9 and Glu-13) with a hydrophobic Leu residue provides peptides that mimic the structural and functional properties of ApoA-I to a high degree.

In some embodiments, the Apo-A-I agonist has the structure $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$-$X_{20}$-$X_{21}$-$X_{22}$ (SEQ ID NO:4) wherein: $X_1$ is Pro (P), Ala (A), Gly (G), Gln (Q), Asn (N), Asp (D) or D-Pro (p); $X_2$ is an aliphatic amino acid; $X_3$ is Leu (L) or Phe (F); $X_4$ is Glu (E); $X_5$ is an aliphatic amino acid; $X_6$ is Leu (L) or Phe (F); $X_7$ is Glu (E) or Leu (L); $X_8$ is Asn (N) or Gln (Q); $X_9$ is Leu (L); $X_{10}$ is Leu (L), Trp (W) or Gly (G); $X_{11}$ is an acidic amino acid; $X_{12}$ is Arg (R); $X_{13}$ is Leu (L) or Gly (G); $X_{14}$ is Leu (L), Phe (F) or Gly (G); $X_{15}$ is Asp (D); $X_{16}$ is Ala (A); $X_{17}$ is Leu (L); $X_{18}$ is Asn (N) or Gln (Q); $X_{19}$ is a basic amino acid; $X_{20}$ is a basic amino acid; $X_{21}$ is Leu (L); and $X_{22}$ is a basic amino acid. In some embodiments, the peptide backbone comprises peptide bond or amide linkages (—C(O)NH—). However, in some embodiments, the peptide analogues are contemplated wherein one or more amide linkage is replaced with a linkage other than amide, such as a substituted amide or an isostere of amide. One having skill in the art will recognize that in embodiments having non-amide linkages, the term "amino acid" or "residue" as used herein refers to other bifunctional moieties bearing groups similar in structure to the side chains of the amino acids.

Substituted amides generally include, but are not limited to, groups of the formula —C(O)NR—, where R is $(C_1-C_6)$ alkyl, substituted $(C_1-C_6)$ alkyl, $(C_1-C_6)$ alkenyl, substituted $(C_1-C_6)$ alkenyl, $(C_1-C_6)$ alkynyl, substituted $(C_1-C_6)$ alkynyl, $(C_5-C_{20})$ aryl, substituted $(C_5-C_{20})$ aryl, $(C_6-C_{26})$ alkaryl, substituted $(C_6-C_{26})$ alkaryl, 5-20 membered heteroaryl, substituted 5-20 membered heteroaryl, or 6-26 membered alkheteroaryl and substituted 6-26 membered alkheteroaryl.

Isosteres of amide generally include, but are not limited to, —CH$_2$NH—, —CH$_2$S—, —CH$_2$CH$_2$—, —CH=CH— (cis and trans), —C(O)CH$_2$—, —CH(OH)CH$_2$—, and —CH$_2$SO—. Compounds having such non-amide linkages and methods for preparing such compounds are known (see, e.g., Spatola, March 1983, Vega Data Vol. 1, Issue 3; Spatola, 1983, "Peptide Backbone Modifications" In: Chemistry and Biochemistry of Amino Acids Peptides and Proteins, Weinstein, ed., Marcel Dekker, New York, p. 267 (general review); Morley, 1980, Trends Pharm. Sci. 1:463-468; Hudson et al., 1979, Int. J. Prot. Res. 14:177-185 (—CH$_2$NH—, —CH$_2$CH$_2$—); Spatola et al., 1986, Life Sci. 38:1243-1249 (—CH$_2$—S); Hann, 1982, J. Chem. Soc. Perkin Trans. I. 1:307-314 (—CH=CH—, cis and trans); Almquist et al., 1980, J. Med. Chem. 23:1392-1398 (—COCH$_2$—); Jennings-White et al., Tetrahedron. Lett. 23:2533 (—COCH$_2$—); European Patent Application EP 45665 (1982) CA 97:39405 (—CH(OH)CH$_2$—); Holladay et al., 1983, Tetrahedron Lett. 24:4401-4404 (—C(OH)CH$_2$—); and Hruby, 1982, Life Sci. 31:189-199 (—CH$_2$—S—).

Additionally, one or more amide linkages can be replaced with peptidomimetic or amide mimetic moieties which do not significantly interfere with the structure or activity of the peptides. Suitable amide mimetic moieties are described, for example, in Olson et al., 1993, J. Med. Chem. 36:3039-3049.

In some embodiments, peptides of structures above are composed of a larger percentage of hydrophobic residues, have a significantly larger <H$_o$> and <$\mu_H$>, and have a two-fold larger pho-angle than the consensus 22-mer (SEQ ID NO: 1). These differences in properties lead to significant differences in activity. Whereas the consensus 22-mer (SEQ ID NO: 1) exhibits only 10% LCAT activation as compared with native ApoA-I, SEQ ID NO:2 (PVLELFENLLERLL-DALQKKLK) exhibits 86% activation as compared with native ApoA-I in the same assays. SEQ ID NO:3 (pVLELF-ENLLERLLDALQKKLK), which differs from SEQ ID NO:2 only by a D-Pro (p) at position $X_1$, exhibits 111% LCAT activation as compared with native ApoA-I.

Certain amino acid residues in the core peptides of SEQ ID NO:4 can be replaced with other amino acid residues without significantly deleteriously affecting, and in many cases even enhancing, the activity of the peptides. Thus, also contemplated are altered or mutated forms of the core peptides of SEQ ID NO:4 wherein at least one defined amino acid residue in the structure is substituted with another amino acid residue. As one of the features affecting the activity of the core peptides is believed to be their ability to form α-helices in the presence of lipids that exhibit the amphipathic and other properties described above, it will be recognized that in preferred embodiments, the amino acid substitutions are conservative, i.e., the replacing amino acid residue has physical and chemical properties that are similar to the amino acid residue being replaced.

For purposes of determining conservative amino acid substitutions, the amino acids can be conveniently classified into two main categories-hydrophilic and hydrophobic-depending primarily on the physical-chemical characteristics of the amino acid side chain. These two main categories can be further classified into subcategories that more distinctly define the characteristics of the amino acid side chains. For example, the class of hydrophilic amino acids can be further subdivided into acidic, basic and polar amino acids. The class of hydrophobic amino acids can be further subdivided into apolar and aromatic amino acids. The definitions of the various categories of amino acids that define SEQ ID NO:4 are as follows:

"Hydrophilic Amino Acid" refers to an amino acid exhibiting a hydrophobicity of less than zero according to the normalized consensus hydrophobicity scale of Eisenberg et al., 1984, J. Mol. Biol. 179:125-142. Genetically encoded hydrophilic amino acids include Thr (T), Ser (S), His (H), Glu (E), Asn (N), Gln (Q), Asp (D), Lys (K) and Arg (R).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Glu (E) and Asp (D).

"Basic Amino Acid" refers to a hydrophilic amino acid having a side chain pK value of greater than 7. Basic amino acids typically have positively charged side chains at physiological pH due to association with hydronium ion. Genetically encoded basic amino acids include His (H), Arg (R) and Lys (K).

"Polar Amino Acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (Q) Ser (S) and Thr (T).

"Hydrophobic Amino Acid" refers to an amino acid exhibiting a hydrophobicity of greater than zero according to the normalized consensus hydrophobicity scale of Eisenberg, 1984, J. Mol. Biol. 179:125-142. Genetically encoded hydrophobic amino acids include Pro (P), Ile (I), Phe (F), Val (V), Leu (L), Trp (W), Met (M), Ala (A), Gly (G) and Tyr (Y).

"Aromatic Amino Acid" refers to a hydrophobic amino acid with a side chain having at least one aromatic or heteroaromatic ring. The aromatic or heteroaromatic ring may contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR and the like where each R is independently $(C_1-C_6)$ alkyl, substituted $(C_1-C_6)$ alkyl, $(C_1-C_6)$ alkenyl, substituted $(C_1-C_6)$ alkenyl, $(C_1-C_6)$ alkynyl, substituted $(C_1-C_6)$ alkynyl, $(C_5-C_{20})$ aryl, substituted $(C_5-C_{20})$ aryl, $(C_6-C_{26})$ alkaryl, substituted $(C_6-C_{26})$ alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe (F), Tyr (Y) and Trp (W).

"Nonpolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded apolar amino acids include Leu (L), Val (V), Ile (I), Met (M), Gly (G) and Ala (A).

"Aliphatic Amino Acid" refers to a hydrophobic amino acid having an aliphatic hydrocarbon side chain. Genetically encoded aliphatic amino acids include Ala (A), Val (V), Leu (L) and Ile (I).

The amino acid residue Cys (C) is unusual in that it can form disulfide bridges with other Cys (C) residues or other sulfanyl-containing amino acids. The ability of Cys (C) residues (and other amino acids with —SH containing side chains) to exist in a peptide in either the reduced free —SH or oxidized disulfide-bridged form affects whether Cys (C) residues contribute net hydrophobic or hydrophilic character to a peptide. While Cys (C) exhibits a hydrophobicity of 0.29 according to the normalized consensus scale of Eisenberg (Eisenberg, 1984, supra), it is to be understood that for purposes herein Cys (C) is categorized as a polar hydrophilic amino acid, notwithstanding the general classifications defined above.

As will be appreciated by those of skill in the art, the above-defined categories are not mutually exclusive. Thus, amino acids having side chains exhibiting two or more physical-chemical properties can be included in multiple categories. For example, amino acid side chains having aromatic moieties that are further substituted with polar substituents, such as Tyr (Y), may exhibit both aromatic hydrophobic properties and polar or hydrophilic properties, and can therefore be included in both the aromatic and polar categories. The appropriate categorization of any amino acid will be apparent to those of skill in the art, especially in light of the detailed disclosure provided herein.

Certain amino acid residues, called "helix breaking" amino acids, have a propensity to disrupt the structure of .alpha.-helices when contained at internal positions within the helix. Amino acid residues exhibiting such helix-breaking properties are well-known in the art (see, e.g., Chou and Fasman, Ann. Rev. Biochem. 47:251-276) and include Pro (P), Gly (G) and potentially all D-amino acids (when contained in an L-peptide; conversely, L-amino acids disrupt helical structure when contained in a D-peptide). While these helix-breaking amino acid residues fall into the categories defined above, with the exception of Gly (G) (discussed infra), these residues should not be used to substitute amino acid residues at internal positions within the helix-they should only be used to substitute 1-3 amino acid residues at the N-terminus and/or C-terminus of the peptide.

While the above-defined categories have been exemplified in terms of the genetically encoded amino acids, the amino acid substitutions need not be, and in certain embodiments preferably are not, restricted to the genetically encoded amino acids. Indeed, many of the preferred peptides of SEQ ID NO:4 contain genetically non-encoded amino acids. Thus, in addition to the naturally occurring genetically encoded amino acids, amino acid residues in the core peptides of SEQ ID NO:4 may be substituted with naturally occurring non-encoded amino acids and synthetic amino acids.

Certain commonly encountered amino acids which provide useful substitutions for the core peptides of SEQ ID NO:4 include, but are not limited to, β-alanine (β-Ala) and other omega-amino acids such as 3-aminopropionic acid, 2,3-diaminopropionic acid (Dpr), 4-aminobutyric acid and so forth; α-aminoisobutyric acid (Aib); ε-aminohexanoic acid (Aha); 6-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); naphthylalanine (Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,4-diaminobutyric acid (Dbu); 2,3-diaminobutyric acid (Dab); p-aminophenylalanine (Phe(pNH$_2$)); N-methyl valine (MeVal); homocysteine (hCys), homophenylalanine (hphe) and homoserine (hSer); hydroxyproline (Hyp), homoproline (hPro), N-methylated amino acids and peptoids (N-substituted glycines).

While in most instances, the amino acids of the peptides will be substituted with L-enantiomeric amino acids, the substitutions are not limited to L-enantiomeric amino acids. Thus, also included in the definition of "mutated" or "altered" forms are those situations where at least one L-amino acid is replaced with an identical D-amino acid (e.g., L-Arg to D-Arg) or with a D-amino acid of the same category or subcategory (e.g., L-Arg to D-Lys), and vice versa. Indeed, in certain preferred embodiments that are suitable for oral administration to animal subjects, the peptides may advantageously be composed of at least one D-enantiomeric amino acid. Peptides containing such D-amino acids are thought to be more stable to degradation in the oral cavity, gut or serum than are peptides composed exclusively of L-amino acids.

As noted above, D-amino acids tend to disrupt the structure of α-helices when contained at internal positions of an α-helical L-peptide. D-amino acid substitutions should be limited to 1-3 amino acid residues at the N-terminus and/or C-terminus of the peptide.

As previously discussed, the amino acid Gly (G) generally acts as a helix-breaking residue when contained at internal positions of a peptide. However, in the presence of lipids, Gly (G) containing peptides exhibit significant helical structure, as well as activity. For example, whereas the peptide SEQ ID NO:5 (PVLELFENLLERGLDALQKKLK) exhibits only 13% helical structure in buffer, 76% helical structure is observed in the presence of micelles. Preferably, only internal residues positioned within about +/−1 helical turn of the center of the peptide (particularly for peptides composed of an even number of amino acids) are substituted with Gly (G). Additionally, it is preferred that only one internal amino acid residue in the peptide be substituted with Gly (G).

In still another embodiment, the first one to four amino acid residues at the N-terminus and/or C-terminus of the core peptides are substituted with one or more amino acid residues, or one or more peptide segments, that are known to confer stability to regions of α-helical secondary structure ("end-cap" residues or segments). Such end-cap residues and segments are known in the art (see, e.g., Richardson and Richardson; 1988, Science 240:1648-1652; Harper et al., 1993, Biochemistry 32(30):7605-7609; Dasgupta and Bell, 1993, Int. J. Peptide Protein Res. 41:499-511; Seale et al., 1994, Protein Science 3:1741-1745; Doig et al., 1994, Biochemistry 33:3396-3403; Zhou et al., 1994, Proteins 18:1-7; Doig and Baldwin, 1995, Protein Science 4:1325-1336; Odaert et al., 1995, Biochemistry 34:12820-12829; Petrukhov et al., 1996, Biochemistry 35:387-397; Doig et al., 1997, Protein Science 6:147-155). Alternatively, the first one to four N-terminal and/or C-terminal amino acid residues of SEQ ID NO:4 can be replaced with peptidomimetic moieties that mimic the structure and/or properties of end-cap residues or segments. Suitable end-cap mimetics are known in the art, and are described, for example, in Richardson and Richardson, 1988, Science 240:1648-1652; Harper et al., 1993, Biochemistry 32(30):7605-7609; Dasgupta and Bell, 1993, Int. J. Peptide Protein Res. 41:499-511; Seale et al., 1994, Protein Science 3:1741-1745; Doig et al., 1994, Biochemistry 33:3396-3403; Zhou et al., 1994, Proteins 18:1-7; Doig and Baldwin, 1995, Protein Science 4:1325-1336; Odaert et al., 1995, Biochemistry 34:12820-12829; Petrukhov et al., 1996, Biochemistry 35:387-397; Doig et al., 1997, Protein Science 6:147-155.

While SEQ ID NO:4 contains 22 specified amino acid residue positions, it is to be understood that the core peptides can contain fewer than 22 amino acid residues. Indeed, truncated or internally deleted forms of SEQ ID NO:4 containing as few as 18 or even 15 amino acid residues that substantially retain the overall characteristics and properties of the amphipathic helix formed by the core peptides may be used.

Truncated forms of the peptides are obtained by deleting one or more amino acids from the N- and/or C-terminus. Internally deleted forms are obtained by deleting one or more amino acids from internal positions within the peptide. The internal amino acid residues deleted may or may not be consecutive residues.

Those of skill in the art will recognize that deleting an internal amino acid residue from a core peptide will cause the plane of the hydrophilic-hydrophobic interface of the helix to rotate by 100 degrees at the point of the deletion. As such rotations can significantly alter the amphipathic properties of the resultant helix. In a preferred embodiment, amino acid residues are deleted so as to substantially retain the alignment of the plane of the hydrophilic-hydrophobic interface along the entire long axis of the helix. This can be achieved by deleting a sufficient number of consecutive or non-consecutive amino acid residues such that one complete helical turn is deleted. An idealized α-helix contains 3.6 residues per turn. Thus, in a preferred embodiment, groups of 3-4 consecutive or non-consecutive amino acid residues are deleted. Whether 3 amino acids or 4 amino acids are deleted will depend upon the position within the helix of the first residue to be deleted. Determining the appropriate number of consecutive or non-consecutive amino acid residues that constitute one complete helical turn from any particular starting point within an amphipathic helix is well within the capabilities of those of skill in the art.

The core peptides of SEQ ID NO:4 can also be extended at one or both termini or internally with additional amino acid residues that do not substantially interfere with, and in some embodiments even enhance, the structural and/or functional properties of the peptides. Indeed, extended core peptides containing as many as 23, 25, 26, 29 or more amino acid residues. Preferably, such extended peptides will substantially retain the net amphipathicity and other properties of the 22-mer. Of course, it will be recognized that adding amino acids internally will rotate the plane of the hydrophobic-hydrophilic interface at the point of the insertion in a manner similar to that described above for internal deletions. Thus, the considerations discussed above in connection with internal deletions apply to internal additions, as well.

In one embodiment, the core peptides are extended at the N- and/or C-terminus by least one helical turn. Preferably, such extensions will stabilize the helical secondary structure in the presence of lipids, such as the end-cap amino acids and segments previously described.

In a particularly preferred embodiment, the core peptide is extended at the C-terminus by a single basic amino acid residue, preferably Lys (K).

Also included are "blocked" forms of the ApoA-I agonist, i.e., forms of the ApoA-I agonists in which the N- and/or C-terminus is blocked with a moiety capable of reacting with the N-terminal —NH$_2$ or C-terminal —C(O)OH. For example, it has been shown that removing the N- and/or C-terminal charges of the ApoA-I agonists containing 18 or fewer amino acid residues (by synthesizing N-acylated peptide amides/ester/hydrazides/alcohols and substitutions thereof) results in agonists which approach, and in some cases even exceed, the activity of the unblocked form of the agonist. In some embodiments containing 22 or more amino acids, blocking the N- or C-terminus results in ApoA-I agonists which exhibit lower activity than the unblocked forms. However, blocking both the N- and C-termini of ApoA-I agonists composed of 22 or more amino acids is contemplated to restore activity. Thus, in a preferred embodiment, either the N- and/or C-terminus (preferably both termini) of core peptides containing 18 or fewer amino acids are blocked, whereas the N- and C-termini of peptides containing 22 or more amino acids are either both blocked or both unblocked.

Typical N-terminal blocking groups include RC(O)—, where R is —H, ($C_1$-$C_6$) alkyl, ($C_1$-$C_6$) alkenyl, ($C_1$-$C_6$) alkynyl, ($C_5$-$C_{20}$) aryl, ($C_6$-$C_{26}$) alkaryl, 5-20 membered heteroaryl or 6-26 membered alkheteroaryl. Preferred N-terminal blocking groups include acetyl, formyl and dansyl. Typical C-terminal blocking groups include —C(O)NRR and —C(O)OR, where each R is independently defined as above. Preferred C-terminal blocking groups include those where each R is independently methyl. While not intending to be bound by any particular theory, it is believed that such terminal blocking groups stabilize the α-helix in the presence of lipids (see, e.g., Venkatachelapathi et al., 1993, PROTEINS: Structure, Function and Genetics 15:349-359).

The native structure of ApoA-I contains eight helical units that are thought to act in concert to bind lipids (Nakagawa et al., 1985, J. Am. Chem. Soc. 107:7087-7092; Ananthara-maiah et al., 1985, J. Biol. Chem. 260:10248-10262; Vanloo et al., 1991, J. Lipid Res. 32:1253-1264; Mendez et al., 1994, J. Clin. Invest. 94:1698-1705; Palgunari et al., 1996, Arterioscler. Thromb. vasc. Biol. 16:328-338; Demoor et al., 1996, Eur. J. Biochem. 239:74-84). Thus, also included are ApoA-I agonists comprised of dimers, trimers, tetramers and even higher order polymers ("multimers") of the core peptides described herein. Such multimers may be in the form of tandem repeats, branched networks or combinations thereof. The core peptides may be directly attached to one another or separated by one or more linkers.

The core peptides that comprise the multimers may be the peptides of SEQ ID NO:4, analogues of SEQ ID NO:4, mutated forms of SEQ ID NO:4, truncated or internally deleted forms of SEQ ID NO:4, extended forms of SEQ ID NO:4 and/or combinations thereof. The core peptides can be connected in a head-to-tail fashion (i.e., N-terminus to C-terminus), a head-to-head fashion, (i.e., N-terminus to N-terminus), a tail-to-tail fashion (i.e., C-terminus to C-terminus), or combinations thereof.

In some embodiments, the multimers are tandem repeats of two, three, four and up to about ten core peptides. Preferably, the multimers are tandem repeats of from 2 to 8 core peptides.

The linker, if used, may be flexible, rigid or semi-rigid, depending on the desired properties of the multimer. Suitable linkers include, for example, amino acid residues such as Pro or Gly or peptide segments containing from about 2 to about 5, 10, 15 or 20 or even more amino acids, bifunctional organic compounds such as $H_2N(CH_2)_nCOOH$ where n is an integer from 1 to 12, and the like. Examples of such linkers, as well as methods of making such linkers and peptides incorporating such linkers are known in the art (see, e.g., Hunig et al., 1974, Chem. Ber. 100:3039-3044; Basak et al., 1994, Bioconjug. Chem. 5(4):301-305).

In some embodiments, the tandem repeats are internally punctuated by a single proline residue.

In some embodiments, it may be desirable to employ cleavable linkers that permit the release of one or more helical segments under certain conditions. Suitable cleavable linkers include peptides having amino acid sequences that are recognized by proteases, oligonucleotides that are cleaved by endonucleases and organic compounds that can be cleaved via chemical means, such as under acidic, basic or other conditions. Preferably, the cleavage conditions will be relatively mild so as not to denature or otherwise degrade the helical segments and/or non-cleaved linkers composing the multimeric ApoA-I agonists.

In some embodiments, the linkers employed are peptides that are substrates for endogenous circulatory enzymes, thereby permitting the multimeric ApoA-I agonists to be selectively cleaved in vivo. Endogenous enzymes suitable for cleaving the linkers include, for example, proapolipoprotein A-I propeptidase. Appropriate enzymes, as well as peptide segments that act as substrates for such enzymes, are known in the art (see, e.g., Edelstein et al., 1983, J. Biol. Chem. 258:11430-11433; Zanis, 1983, Proc. Natl. Acad. Sci. USA 80:2574-2578).

Alternatively, as the native apolipoproteins permit cooperative binding between antiparallel helical segments, peptide linkers which correspond in primary sequence to the peptide segments connecting adjacent helices of the native apolipoproteins, including, for example, ApoA-I, ApoA-II, ApoA-IV, ApoC-I, ApoC-II, ApoC-III, ApoD, ApoE and ApoJ can be conveniently used to link the core peptides. These sequences are known in the art (see, e.g., Rosseneu et al., "Analysis of the Primary and of the Secondary Structure of the Apolipoproteins," In: Structure and Function of Lipoproteins, Ch. 6, 159-183, CRC Press, Inc., 1992).

Other linkers which permit the formation of intermolecular hydrogen bonds or salt bridges between tandem repeats of antiparallel helical segments include peptide reverse turns such as β-turns and α-turns, as well as organic molecules that mimic the structures of peptide β-turns and/or α-turns. Generally, reverse turns are segments of peptide that reverse the direction of the polypeptide chain so as to allow a single polypeptide chain to adopt regions of antiparallel β-sheet or antiparallel α-helical structure. β-turns generally are composed of four amino acid residues and β-turns are generally composed of three amino acid residues.

In some embodiments, the multimers are in the form of branched networks. Such networks are obtained through the use of multifunction linking moieties that permit more than two helical units to be attached to a simple linking moiety. Thus, branched networks employ molecules having three, four or more functional groups that are capable of covalently attaching to the N- and/or C-terminus of a peptide. Suitable linking moieties include, for example, amino acid residues having side chains bearing hydroxyl, sulfanyl, amino, carboxyl, amide and/or ester functionalities, such as, for example, Ser (S), Thr (T), Cys (C), Tyr (Y), Asn (N), Gln (Q), Lys (K), Arg (R), Orn, Asp (D) and Glu (E); or other organic molecules containing such functional groups.

In some embodiments, the ApoA-I agonists are 22 amino acid residue peptides according to SEQ ID NO:4, or the N-terminal acylated and/or C-terminal amidated or esterified forms thereof.

In some embodiments, the ApoA-I agonists are 22 amino acid residue peptides according to SEQ ID NO:4, or the N-terminal acylated and/or C-terminal amidated or esterified forms thereof, in which: $X_1$ is Pro (P), Gly (G), Ala (A), Asn (N) or D-Pro (p); $X_2$ is Ala (A), Val (V) or Leu (L); $X_5$ is Leu (L); $X_6$ is Phe (F); $X_{11}$ is Glu (E); $X_{19}$ is Lys (K); $X_{20}$ is Lys (K); and/or $X_{22}$ is Lys (K), and each of $X_3$, $X_4$, $X_7$, $X_8$, $X_9$, $X_{10}$, $X_{12}$, $X_{13}$, $X_{14}$, $X_{15}$, $X_{16}$, $X_{17}$, $X_{18}$ and $X_{21}$ are as previously defined for SEQ ID NO:4.

In some embodiments, the ApoA-I agonists are those in which $X_2$ is Val (V); and/or $X_{18}$ is Gln (Q).

In still another embodiment, the ApoA-I agonists are 22 amino acid residue peptides according to SEQ ID NO:4, or the N-terminal acylated and/or C-terminal amidated or esterified forms thereof, in which one of $X_{10}$, $X_{13}$ or $X_{14}$ is Gly (G) and the others of $X_{10}$, $X_{13}$ and $X_{14}$ are other than Gly (G). When $X_{14}$ is Gly (G), $X_7$ is preferably Glu (E).

In some embodiments, the ApoA-I agonists are peptides selected from the group consisting of: PVLELFENLLER-LGDALQKKLK; (SEQ ID NO:6) PVLELFENLGERLL-DALQKKLK; (SEQ ID NO:7) and PVLELFENLLER-GLDALQKKLK; (SEQ ID NO:5) and the N-terminal acylated and/or C-terminal amidated or esterified forms thereof.

Embodiments containing internal glycine residues can be readily synthesized in high yield by way of segment condensation, thereby providing significant advantages for large-scale production. Segment condensation, i.e., the joining together of small constituent peptide chains to form a larger peptide chain, has been used to prepare many biologically active peptides, including 44-amino acid residue mimics of ApoA-I (see, e.g., Nakagawa et al., 1985, J. Am Chem. Soc. 107:7087-7083; Nokihara et al., 1989, Peptides 1988:166-168; Kneib-Cordonnier et al., 1990, Int. J. Pept. Protein Res. 35:527-538), and is considered to be a cost-effective method for high-yield bulk synthesis of the core peptides.

In still another embodiment, the ApoA-I agonists are 22 amino acid residue peptides according to SEQ ID NO:4, or the N-terminal acylated and/or C-terminal amidated or esterified forms thereof, in which when $X_7$ is Leu (L), $X_{10}$ is Trp (W), $X_1$ is other than Gly (G) and/or $X_{14}$ is other than Gly (G).

A one embodiments, the peptide is SEQ ID NO:8 (PVLELFLNLWERLLDALQKKLK).

In still other embodiments, the ApoA-I agonists are selected from the group of peptides set forth below:

```
                                          (SEQ ID NO: 3)
            pVLELFENLLERLLDALQKKLK;;

(SEQ ID NO: 9)
            GVLELFENLLERLLDALQKKLK;;

(SEQ ID NO: 2)
            PVLELFENLLERLLDALQKKLK;;

(SEQ ID NO: 10)
            PVLELFENLLERLFDALQKKLK;;

(SEQ ID NO: 6)
            PVLELFENLLERLGDALQKKLK;;

(SEQ ID NO: 11)
            PVLELFENLWERLLDALQKKLK;;

(SEQ ID NO: 12)
            PLLELFENLLERLLDALQKKLK;;

(SEQ ID NO: 7)
            PVLELFENLGERLLDALQKKLK;;

(SEQ ID NO: 13)
            PVFELFENLLERLLDALQKKLK;;
```

-continued

AVLELFENLLERLLDALQKKLK;; (SEQ ID NO: 14)

PVLELFENLLERGLDALQKKLK;; (SEQ ID NO: 5)

PVLELFLNLWERLLDALQKKLK;; (SEQ ID NO: 15)

PVLELFEQLLERLLDALQKKLK;; (SEQ ID NO: 16)

PVLELFENLLERLLDALNKKLK;; (SEQ ID NO: 17)

PVLELFENLLDRLLDALQKKLK;; (SEQ ID NO: 18)

DVLELFENLLERLLDALQKKLK;; (SEQ ID NO: 19)

PVLDEFREKLNEELEALKQKLK;; (SEQ ID NO: 1)

PVLDEFREKLNEALEALKQKLK;; (SEQ ID NO: 20)

PVLDEFREKLNERLEALKQKLK;; (SEQ ID NO: 21)

LDDLLQKWAEAFNOLLKK;; (SEQ ID NO: 22)

EWLKAFYEKVLEKLKELF*;; (SEQ ID NO: 23)

DWFKAFYDKVFEKFKEFF;; (SEQ ID NO: 24)

GIKKFLGSIWKFIKAFVG;; (SEQ ID NO: 25)

DWFKAFYDKVAEKFKEAF;; (SEQ ID NO: 26)

DWLKAFYDKVAEKLKEAF;; (SEQ ID NO: 27)

DWLKAFYDKVFEKFKEFF;; (SEQ ID NO: 28)

EWLEAFYKKVLEKLKELF;; (SEQ ID NO: 29)

DWFKAFYDKFFEKFKEFF;; (SEQ ID NO: 30)

EWLKAFYEKVLEKLKELF;; (SEQ ID NO: 31)

EWLKAEYEKVEEKLKELF*;; (SEQ ID NO: 32)

EWLKAEYEKVLEKLKELF*;; (SEQ ID NO: 33)

EWLKAFYKKVLEKLKELF*.; (SEQ ID NO: 34)

PVLDLFRELLNELLEALKQKLK; (SEQ ID NO: 35)

PVLDLFRELLNLXLEALKEKLK; (SEQ ID NO: 36)

PVLDLFRELLNELLEZLKQKLK; (SEQ ID NO: 37)

GVLDLFRELLNELLEALKQKLK;; (SEQ ID NO: 38)

PVLDLFRELLNEGLEALKQKLK; (SEQ ID NO: 39)

GVLDLFRELLNEGLEALKQKLK; (SEQ ID NO: 40)

pVLDLFRELLNEGLEALKQKLK; (SEQ ID NO: 41)

PVLDLFRELLNEGLEAZKQKLK; (SEQ ID NO: 42)

PVLDLFRELLNEGLEWLKQKLK; (SEQ ID NO: 43)

PVLDLFRELWNEGLEALKQKLK; (SEQ ID NO: 44)

PVLDLFRELLNEGLEALOQOLO; (SEQ ID NO: 45)

PVLDFFRELLNEGLEALKQKLK; (SEQ ID NO: 46)

PVLELFRELLNEGLEALKQKLK; (SEQ ID NO: 47)

PVLDLFREGLNELLEALKQKLK; (SEQ ID NO: 48)

PVLDLFRELGNELLEALKQKLK; (SEQ ID NO: 49)

PVLDLFRELLNELGEALKQKLK; (SEQ ID NO: 50)

PVLDLFRELLNELLEGLKQKLK; (SEQ ID NO: 51)

PVLDLFRELLNELLEAGKQKLK; (SEQ ID NO: 52)

PVLDLFRELLNELLEWLKQKLK; (SEQ ID NO: 53)

pVLDLFRELLNELLEALKQKLKK; (SEQ ID NO: 54)

PVLDLFRELLNEXLEALKQKLK; (SEQ ID NO: 55)

PVLDLFKELLNELLEALKQKLK; (SEQ ID NO: 56)

PVLDLFRELLNELLEAZKQKLK; (SEQ ID NO: 57)

PVLDLFKELLQELLEALKQKLK; (SEQ ID NO: 58)

PVLDLFRELLNELLEALOQOLO; (SEQ ID NO: 59)

PVLDLFRELWNELLEALKQKLK; (SEQ ID NO: 60)

PVLDLLRELLNELLEALKQKLK; (SEQ ID NO: 61)

PVLELFKELLQELLEALKQKLK; (SEQ ID NO: 62)

PLLELFKELLQELLEALKQKLK; (SEQ ID NO: 63)

PVLDLFRELLNELLEALQKKLK; (SEQ ID NO: 64)

PVLDFFRELLNEXLEALKQKLK; (SEQ ID NO: 65)

-continued

PVLDLFRELLNELLELLKQKLK; (SEQ ID NO: 66)

PVLDLFRELLNELZEALKQKLK; (SEQ ID NO: 67)

PVLDLFRELLNELWEALKQKLK; (SEQ ID NO: 68)

AVLDLFRELLNELLEALKQKLK; (SEQ ID NO: 69)

QVLDLFRELLNELLEALKQKLK; (SEQ ID NO: 70)

PVLDLFOELLNELLEALOQOLO; (SEQ ID NO: 71)

NVLDLFRELLNELLEALKQKLK; (SEQ ID NO: 72)

PVLDLFRELLNELLEFLKQKLK; (SEQ ID NO: 73)

PVLELFNDLLRELLEALQKKLK; (SEQ ID NO: 74)

PVLELFNDLLRELLEALKQKLK; (SEQ ID NO: 75)

PVLELFKELLNELLDALRQKLK; (SEQ ID NO: 76)

PVLDLFRELLENLLEALQKKLK; (SEQ ID NO: 77)

PVLELFERLLEDLLQALNKKLK; (SEQ ID NO: 78)

PVLELFERLLEDLLKALNQKLK; (SEQ ID NO: 79)

DVLDLFRELLNELLEALKQKLK; (SEQ ID NO: 80)

PALELFKDLLQELLEALKQKLK; (SEQ ID NO: 81)

PVLDLLRELLEELKQKLK*; (SEQ ID NO: 82)

PVLDLFKELLEELKQKLK*; (SEQ ID NO: 83)

PVLDLFRELLEELKQKLK*; (SEQ ID NO: 84)

PVLELFRELLEELKQKLK*; (SEQ ID NO: 85)

PVLELFKELLEELKQKLK*; (SEQ ID NO: 86)

PVLDLFRELLEELKNKLK*; (SEQ ID NO: 87)

PLLDLFRELLEELKQKLK*; (SEQ ID NO: 88)

GVLDLFRELLEELKQKLK*; (SEQ ID NO: 89)

PVLDLFRELWEELKQKLK*; (SEQ ID NO: 90)

NVLDLFRELLEELKQKLK*; (SEQ ID NO: 91)

PLLDLFKELLEELKQKLK*; (SEQ ID NO: 92)

PALELFKDLLEELRQKLR*; (SEQ ID NO: 93)

AVLDLFRELLEELKQKLK*; (SEQ ID NO: 94)

PVLDFFRELLEELKQKLK*; (SEQ ID NO: 95)

PVLDLFREWLEELKQKLK*; (SEQ ID NO: 96)

PLLELLKELLEELKQKLK*; (SEQ ID NO: 97)

PVLELLKELLEELKQKLK*; (SEQ ID NO: 98)

PALELFKDLLEELRQRLK*; (SEQ ID NO: 99)

PVLDLFRELLEELLQKLK; (SEQ ID NO: 100)

PVLDLFRELLEELKQKLK; (SEQ ID NO: 101)

PVLDLFRELLEELOQOLO*; (SEQ ID NO: 102)

PVLDLFOELLEELOQOLK*; (SEQ ID NO: 103)

PALELFKDLLEEFRQRLK*; (SEQ ID NO: 104)

pVLDLFRELLEELKQKLK*; (SEQ ID NO: 105)

PVLDLFRELLEEWKQKLK*; (SEQ ID NO: 106)

PVLELFERLLEDLQKKLK; (SEQ ID NO: 107)

PVLDLFRELLEKLEQKLK; (SEQ ID NO: 108)
and

PLLELFKELLEELKQKLK* (SEQ ID NO: 109)

and the N-terminal acylated and/or N-terminal amidated or esterified forms thereof.

The core peptides may be prepared using any art-known technique for the preparation of peptides. For example, the peptides may be prepared using conventional step-wise solution or solid phase peptide syntheses, or recombinant DNA techniques.

The peptides can be purified by art-known techniques such as reverse phase chromatography high performance liquid chromatography, ion exchange chromatography, gel electrophoresis, affinity chromatography and the like. The actual conditions used to purify a particular peptide will depend, in part, on synthesis strategy and on factors such as net charge, hydrophobicity, hydrophilicity, etc., and will be apparent to those having skill in the art. Multimeric branched peptides can be purified, e.g., by ion exchange or size exclusion chromatography.

Peptide-lipid complexes can be prepared by any of a number of methods described below. Stable preparations having a long shelf life may be made by lyophilization-the co-lyophilization procedure described below being the preferred approach. The lyophilized peptide-lipid complexes can be used to prepare bulk for pharmaceutical reformulation, or to prepare individual aliquots or dosage units which can be reconstituted by rehydration with sterile water or an appropriate buffered solution prior to administration to a subject.

A variety of methods known to those skilled in the art can be used to prepare the peptide-lipid vesicles or complexes. To this end, a number of available techniques for preparing liposomes or proteoliposomes may be used. For example, the peptide can be cosonicated (using a bath or probe sonicator) with appropriate lipids to form complexes. Alternatively the peptide can be combined with preformed lipid vesicles resulting in the spontaneous formation of peptide-lipid complexes. In yet another alternative, the peptide-lipid complexes can be formed by a detergent dialysis method; e.g., a mixture of the peptide, lipid and detergent is dialyzed to remove the detergent and reconstitute or form peptide-lipid complexes (e.g., see Jonas et al., 1986, Methods in Enzymol. 128:553-582).

In accordance with the preferred method, the peptide and lipid are combined in a solvent system which co-solubilizes each ingredient and can be completely removed by lyophilization. To this end, solvent pairs are carefully selected to ensure co-solubility of both the amphipathic peptide and the lipid. In one embodiment, the protein(s) or peptide(s) to be incorporated into the particles can be dissolved in an aqueous or organic solvent or mixture of solvents (solvent 1). The (phospho)lipid component is dissolved in an aqueous or organic solvent or mixture of solvents (solvent 2) which is miscible with solvent 1, and the two solutions are mixed. Alternatively, the peptide and lipid can be incorporated into a co-solvent system; i.e., a mixture of the miscible solvents. A suitable proportion of peptide (protein) to lipids is first determined empirically so that the resulting complexes possess the appropriate physical and chemical properties; e.g., usually (but not necessarily) similar in size to HDL. The resulting mixture is frozen and lyophilized to dryness. Sometimes an additional solvent must be added to the mixture to facilitate lyophilization. This lyophilized product can be stored for long periods and will remain stable.

The lyophilized product can be reconstituted in order to obtain a solution or suspension of the peptide-lipid complex. To this end, the lyophilized powder is rehydrated with an aqueous solution to a suitable volume (often 5 mgs peptide/ml which is convenient for intravenous injection). In some embodiments, the lyophilized powder is rehydrated with phosphate buffered saline or a physiological saline solution. The mixture may have to be agitated or vortexed to facilitate rehydration, and in most cases, the reconstitution step should be conducted at a temperature equal to or greater than the phase transition temperature of the lipid component of the complexes. Within minutes, a clear preparation of reconstituted lipid-protein complexes results.

The ApoA-I agonists can be complexed with a variety of lipids, including saturated, unsaturated, natural and synthetic lipids and/or phospholipids. Suitable lipids include, but are not limited to, small alkyl chain phospholipids, egg phosphatidylcholine, soybean phosphatidylcholine, dipalmitoylphosphatidylcholine, dimyristoylphosphatidylcholine, distearoylphosphatidylcholine 1-myristoyl-2-palmitoylphosphatidylcholine, 1-palmitoyl-2-myristoylphosphatidylcholine, 1-palmitoyl-2-stearoylphosphatidylcholine, 1-stearoyl-2-palmitoylphosphatidylcholine, dioleoylphosphatidylcholine dioleophosphatidylethanolamine, dilauroylphosphatidylglycerol phosphatidylcholine, phosphatidylserine, phosphatidylethanolamine, phosphatidylinositol, sphingomyelin, sphingolipids, phosphatidylglycerol, diphosphatidylglycerol, dimyristoylphosphatidylglycerol, dipalmitoylphosphatidylglycerol, distearoylphosphatidylglycerol, dioleoylphosphatidylglycerol, dimyristoylphosphatidic acid, dipalmitoylphosphatidic acid, dimyristoylphosphatidylethanolamine, dipalmitoylphosphatidylethanolamine, dimyristoylphosphatidylserine, dipalmitoylphosphatidylserine, brain phosphatidylserine, brain sphingomyelin, dipalmitoylsphingomyelin, distearoylsphingomyelin, phosphatidic acid, galactocerebroside, gangliosides, cerebrosides, dilaurylphosphatidylcholine, (1,3)-D-mannosyl-(1,3)diglyceride, aminophenylglycoside, 3-cholesteryl-6'-(glycosylthio)hexyl ether glycolipids, and cholesterol and its derivatives. In some preferred embodiments, the ApoA-I agonists are administered as a complex with sphingomyelin.

Uses

The anticancer agent (e.g., withanolide)-containing nanoparticles find use in a variety of setting. In some embodiments, they are used for research purposes in vitro or in vivo, for example, to study the biological effects of anticancer agents (e.g., with anolides) or other compounds. In some such embodiments, the compositions are used for drug screening.

The anticancer agent (e.g., withanolide)-containing nanoparticles may also be used for screening or diagnostic procedures. For example, in some embodiments, the nanoparticle include a detectable label of moiety (e.g., fluorophore, contrast agent, etc.) that permits detection of the location and amount of nanoparticles associated with a cell, tissue, or subject at one or more time points. In some embodiments, imaging agents are used in imaging procedures employing any of a variety of detection modalities, including, but not limited to, CT, MRI, X-ray, ultrasound, PET, SPECT, molecular imaging, endoscopy, NIRS, and fluoroscopy. Imaging agents included, but are not limited to, fluorophores, luminescent agents, chromophores, radiocontrast agents (e.g., iodine, barium, air, carbon dioxide), MRI contrast agents (e.g., gadolinium-containing contrast agents, iron oxide, iron platinum, manganese, contrast proteins), etc. Imaging can be used, for example, to locate tumors or tumor boundaries, and to assist in surgical interventions.

In some embodiments, a companion diagnostic assay is employed. In some such embodiments, for example, a sample from a subject (e.g., a biopsy) is collected and tested for SR-BI expression. If the expression level is high (e.g., equal to or above a threshold level established as a "cancer" level, above a population average "normal" level, above a previous level from the same subject, etc.), the patient is selected for therapy using a composition described herein. In some embodiments, additional testing is employed during or after therapy to monitor efficacy.

In some embodiments, the composition was used for therapeutic uses to treat, prevent, or ameliorate a disease.

The compositions find use for the treatment of malignant neoplasia, also described as cancer, characterized by tumor cells finally metastasizing into distinct organs or tissues. Examples of malignant neoplasia treated with compounds include solid and hematological tumors. Solid tumors are exemplified by tumors of the breast, bladder, bone, brain, central and peripheral nervous system, colon, connective tissue, endocrine glands (e.g., thyroid and adrenal cortex), esophagus, endometrium, germ cells, head and neck, kidney, liver, lung, larynx and hypopharynx, mesothelioma, muscle, ovary, pancreas, prostate, rectum, renal, small intestine, soft tissue, testis, stomach, skin, ureter, vagina, and vulva. Malignant neoplasia includes inherited cancers exemplified by retinoblastoma and Wilms tumor. In addition, malignant neoplasia includes primary tumors in said organs and corresponding secondary tumors in distant organs ("tumor metastases"). Hematological tumors are exemplified by aggressive and indolent forms of leukemia and lymphoma, namely non-Hodgkins disease, chronic and acute myeloid leukemia (CML/AML), acute lymphoblastic leukemia (ALL), chronic lymphocytic leukemia (CLL), Hodgkins disease, multiple myeloma, and T-cell lymphoma. Also included are myelodysplastic syndrome, plasma cell neoplasia, paraneoplastic syndromes, and cancers of unknown primary site as well as AIDS-related malignancies. In some embodiments, the subject has or is suspected of having adrenocortical carcinoma (ACC).

It will also be appreciated that a cancer (malignant neoplasia) as a life-threatening disease process does not necessarily require the formation of metastases in distant organs. Certain tumors exert devastating effects on the primary organ itself through their aggressive growth properties. These can lead to the destruction of the tissue and organ structure finally resulting in failure of the assigned organ function.

In certain embodiments, provided herein is a method for the treatment of benign neoplasia. Examples of benign neoplasia treated with compounds include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

In other embodiments, provided herein are methods for treating or lessening the severity of autoimmune diseases including, but not limited to, inflammatory bowel disease, arthritis, systemic lupus erythematosus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjogren's syndrome, multiple sclerosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, or vulvodynia.

In some embodiments, provided herein is a method for treating or lessening the severity of one or more diseases and conditions, wherein the disease or condition is selected from heteroimmune conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type hypersensitivity, allergic conjunctivitis, allergic rhinitis, and atopic dermatitis.

In some embodiments, provided herein is a method for treating or lessening the severity of an inflammatory disease including, but not limited to, asthma, appendicitis, Behcet's disease, Blau syndrome, blepharitis, bronchiolitis, bronchitis, bursitis, cervicitis, cholangitis, cholecystitis, chronic recurrent multifocal osteomyelitis (CRMO), colitis, conjunctivitis, cryopyrin associated periodic syndrome (CAPS), cystitis, dacryoadenitis, dermatitis, dermatomyositis, encephalitis, endocarditis, endometritis, enteritis, enterocolitis, epicondylitis, epididymitis, familial cold-induced autoinflammatory syndrome, familial Mediterranean fever (FMF), fasciitis, fibrositis, gastritis, gastroenteritis, hepatitis, hidradenitis suppurativa, laryngitis, mastitis, meningitis, mevalonate kinase deficiency (MKD), Muckle-Well syndrome, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, pyoderma gangrenosum and acne syndrome (PAPA), pyogenic sterile arthritis, rhinitis, salpingitis, sinusitis, stomatitis, synovitis, systemic juvenile rheumatoid arthritis, tendonitis, TNF receptor associated periodic syndrome (TRAPS), tonsillitis, uveitis, vaginitis, vasculitis, or vulvitis.

In certain embodiments, provided herein are methods for treating or lessening the severity of arthropathies and osteopathological diseases including, but not limited to, rheumatoid arthritis, osteoarthritis, gout, polyarthritis, and psoriatic arthritis.

In particular embodiments, provided herein are methods for treating or lessening the severity of hyperproliferative diseases including, but not limited to, psoriasis or smooth muscle cell proliferation including vascular proliferative disorders, atherosclerosis, and restenosis. In certain embodiments, provided herein are methods for treating or lessening the severity of endometriosis, uterine fibroids, endometrial hyperplasia and benign prostate hyperplasia.

In certain embodiments, provided herein are methods for treating or lessening the severity of acute and chronic inflammatory diseases and dermal diseases including, but not limited to, ulcerative colitis, inflammatory bowel disease, Crohns disease, allergic rhinitis, allergic dermatitis, cystic fibrosis, chronic obstructive bronchitis, and asthma.

In some embodiments, provided herein is a method for treating or lessening the severity of a cardiovascular disorder including, but not limited to, myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis, ischemic stroke, cardiac hypertrophy and heart failure.

In certain embodiments, provided herein are methods for treating or lessening the severity of neurodenerative disorders and/or protein aggregation disorders including, but not limited to, Parkinson's disease, Alzheimer's disease or polyglutamine-related disorders including, but not limited to, Huntington's disease, Spinocerebellar ataxia 1 (SCA 1), Machado-Joseph disease (MJD)/Spinocerebella ataxia 3 (SCA 3), Kennedy disease/Spinal and bulbar muscular atrophy (SBMA), Dentatorubral pallidolusyian atrophy (DRPLA), fronto-temporal dementia, Lewy body disease, Pick's disease, and progressive supranuclear palsy (PSP).

The exact amount of nanoparticle composition required will vary from subject to subject, depending on the species, age, and general condition of the subject, the particular compound, its mode of administration, its mode of activity, and the like. The compounds are preferably formulated in dosage unit form for ease of administration and uniformity of dosage. It will be understood, however, that the total daily usage of the compounds and compositions will be decided by the attending physician within the scope of sound medical judgment. The specific therapeutically effective dose level for any particular patient or subject will depend upon a variety of factors including the disorder being treated and the severity of the disorder; the activity of the specific compound employed; the specific composition employed; the age, body weight, general health, sex, and diet of the patient; the time of administration, route of administration, and rate of excretion of the specific compound employed; the duration of the treatment; drugs used in combination or coincidental with the specific compound employed; and like factors well-known in the medical arts.

Furthermore, after formulation with an appropriate pharmaceutically acceptable carrier in a desired dosage, the pharmaceutical compositions can be administered to humans and other animals orally, rectally, parenterally, intracisternally, intravaginally, intraperitoneally, topically (as by powders, ointments, or drops), bucally, as an oral or nasal spray, intratumor, or the like, depending on the severity of the condition being treated. In certain embodiments, the compounds may be administered orally or parenterally (intravenous (IV), intramuscular (IM), intradermal, subcutaneous (SC) and intraperitoneal (IP)) at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect. In some embodiments, the dose is select to achieve circulating plasma concentrations of 100 mg/l to 2 g/l. In another embodiment, desirable serum levels may be maintained by continuous infusion or by intermittent infusion providing about 0.5 mg/kg/hr to 100 mg/kg/hr.

The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In some embodiments, e.g., for treating cancer and/or when a pro-apoptotic effect is desired, a dose that is at or relatively close to the maximum tolerated dose (MTD) is used. In some embodiments, a dose between 50% and 100% of MTD may be used. In some embodiments, a dose between 75% and 100% of MTD may be used. In some embodiments, e.g., in methods of treating a neurodegenerative disease, providing neuroprotection, and/or promoting axonal and/or neurite outgrowth, a lower dose is used than in methods for treating cancer. In some embodiments, the dose for use in such methods is between 10- and 100-fold lower than the MTD and/or between 10- and 100-fold lower than the dose used in cancer. MTD can be determined using standard methods known to those skilled in the art.

Also provided herein is a pharmaceutical pack or kit including one or more containers filled with one or more of the ingredients of the pharmaceutical compositions, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration.

EXAMPLES

The following examples are provided in order to demonstrate and further illustrate certain embodiments and aspects of the technology and are not to be construed as limiting the scope thereof.

Example 1

Preparation of Drug WGA-TA-Loaded sHDL

Different types of lipids (DPPC, SM, DMPC, POPC, DOPC, and EPC), 22A peptide (PVLDLFRELLNELLE-ALKQKLK (SEQ ID NO:35), acetate salt), and anticancer drug WGA-TA (4, 19, 27-triacetyl with alongolide A (WGA-TA)) were dissolved in glacial acetic acid, which was removed by freeze-drying (see Table 1, FIG. 1). PBS was added to the freeze-dried powder, which then was cycled 3 times between 50° C. (3 min) and 20° C. (3 min) with gentle shaking to obtain the sHDL loaded with anticancer drug molecules.

TABLE 1

| DPPC (mg) | SM (mg) | DMPC (mg) | DOPC (mg) | POPC (mg) | EPC (mg) | 22A (mg) | WGA-TA (mg) | Appearance | EE % |
|---|---|---|---|---|---|---|---|---|---|
| 5 | 5 | 0 | 0 | 0 | 0 | 5 | 0 | always clear | ND |
| 5 | 5 | 0 | 0 | 0 | 0 | 5 | 0.5 | always cloudy | 45% |
| 5 | 5 | 0 | 0 | 0 | 0 | 5 | 0.5 | always cloudy | 45% |
| 5 | 5 | 0 | 0 | 0 | 0 | 5 | 0.25 | always cloudy | 47% |
| 10 | 10 | 0 | 0 | 0 | 0 | 10 | 0.25 | always cloudy | 51% |
| 10 | 10 | 0 | 0 | 0 | 0 | 10 | 0.2 | clear at 50° C. cloudy at RT | ND |
| 20 | 20 | 0 | 0 | 0 | 0 | 20 | 0.4 | clear at 50° C. cloudy at RT | ND |
| 20 | 0 | 0 | 0 | 0 | 0 | 10 | 0.2 | clear at 50° C. cloudy at 37° C. and R.T | ND |
| 0 | 20 | 0 | 0 | 0 | 0 | 10 | 0.2 | clear at 50° C. cloudy at 37° C. and R.T | ND |
| 0 | 0 | 20 | 0 | 0 | 0 | 10 | 0.2 | clear at 50° C. and 37° C., cloudy at R.T | ND |
| 0 | 0 | 0 | 0 | 0 | 20 | 10 | 0.2 | always cloudy | ND |
| 0 | 0 | 5 | 0 | 0 | 0 | 2.5 | 0.2 | always cloudy | ND |
| 0 | 0 | 10 | 0 | 0 | 0 | 5 | 0.2 | always cloudy | ND |

TABLE 1-continued

| DPPC (mg) | SM (mg) | DMPC (mg) | DOPC (mg) | POPC (mg) | EPC (mg) | 22A (mg) | WGA-TA(mg) | Appearance | EE % |
|---|---|---|---|---|---|---|---|---|---|
| 0 | 0 | 20 | 0 | 0 | 0 | 10 | 0.2 | clear at 50° C. and 37° C., cloudy at R.T | 23.12% |
| 0 | 0 | 20 | 0 | 0 | 0 | 10 | 0.3 | clear at 50° C. and 37° C., cloudy at R.T | 30.98% |
| 0 | 0 | 10 | 10 | 0 | 0 | 10 | 0.2 | always clear | ND |
| 0 | 0 | 15 | 5 | 0 | 0 | 10 | 0.2 | always clear | 40% |
| 0 | 0 | 10 | 0 | 10 | 0 | 10 | 0.2 | always clear | 58% |
| 0 | 0 | 15 | 0 | 5 | 0 | 10 | 0.2 | always clear | 47% |
| 0 | 0 | 10 | 0 | 10 | 0 | 10 | 0.3 | always clear | 78% |
| 0 | 0 | 10 | 0 | 10 | 0 | 10 | 0.4 | cloudy | ND |
| 0 | 0 | 10 | 0 | 10 | 0 | 10 | 0.5 | cloudy | ND |

The drug encapsulation efficiency (EE %) was determined using the desalting column centrifugation method. sHDL was passed through the desalting column (cut off=7000 Da) to remove any unencapsulated drug. Samples were added with pure ethanol in order to break sHDL before HPLC analysis. The HPLC condition for the analysis of anticancer drug was 35% A (water with 0.1% acetic acid) and 65% B (methanol with 0.1% acetic acid) with a flow rate of 0.7 mL/min, and the detector wavelength was set at 230 nm. The formulation with highest encapsulation efficiency was used for subsequent experiments.

Example 2

DLS and GPC Assay of the Optimized Drug-Loaded sHDL

The optimal WGA-TA-loaded sHDL was analyzed by dynamic laser scattering (DLS) and Gel permeation chromatography (GPC). For DLS, 10 µl of the sHDL was diluted to 1 mL with PBS before measurement on the Malvern Zetasizer Nano (ZSP). For GPC, 40 ul of the sHDL formulations were injected to the HPLC equipped with a TSK 2000 GPC column. The flow rate was set at 0.7 mL/min and the detector wavelength was 220 nm.

Figure 2:
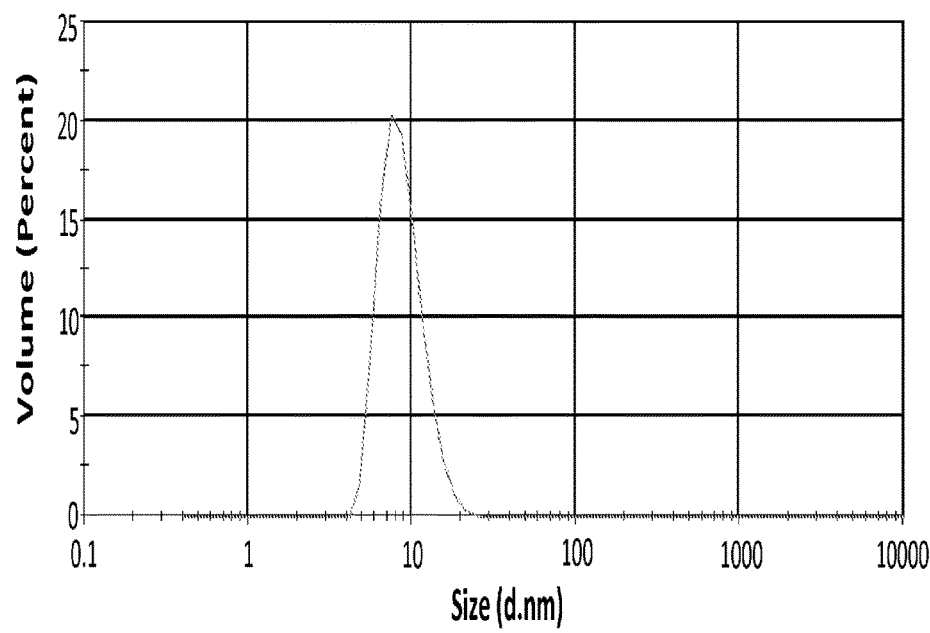
FIG. 2 shows dynamic laser scattering (DLS) analysis of nanoparticles.
Figure 2:
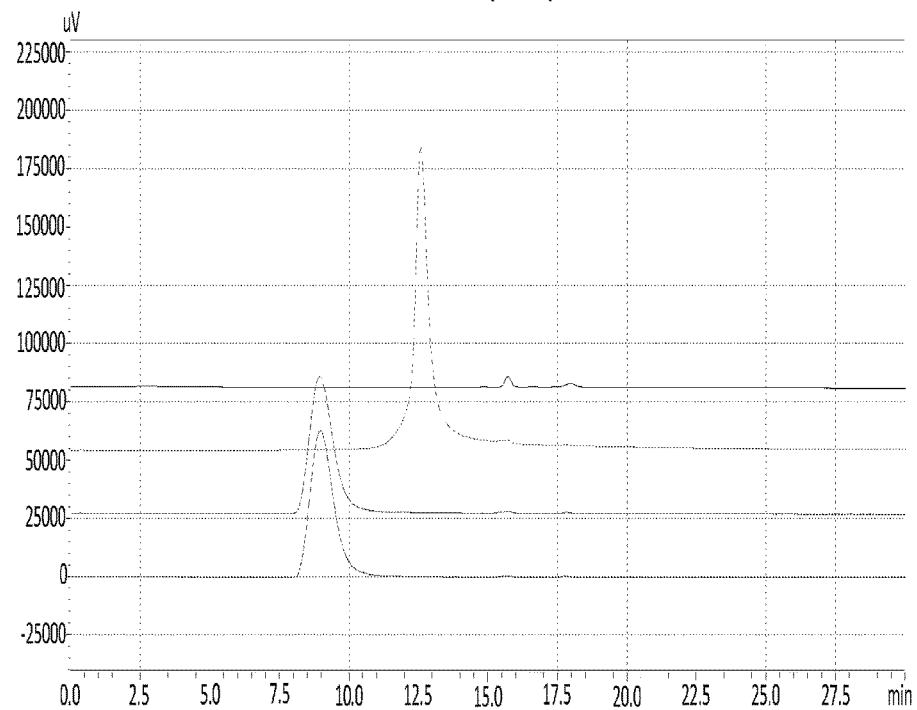

Results are shown in FIG. 2. (A), DLS measurement of drug-loaded sHDL; (B) GPC assay of drug-loaded sHDL. Top trace: PBS; next lower trace: 0.5 mg/mL 22A peptide; third trace: 0.5 mg/mL 22A peptide+1 mg/mL lipids; lowest trace: 15 ug/mL WGA-TA+0.5 mg/mL 22A peptide+1 mg/mL lipids.

Example 3

TEM of Optimized Blank HDL and WGA-TA-sHDL

Figure 3:
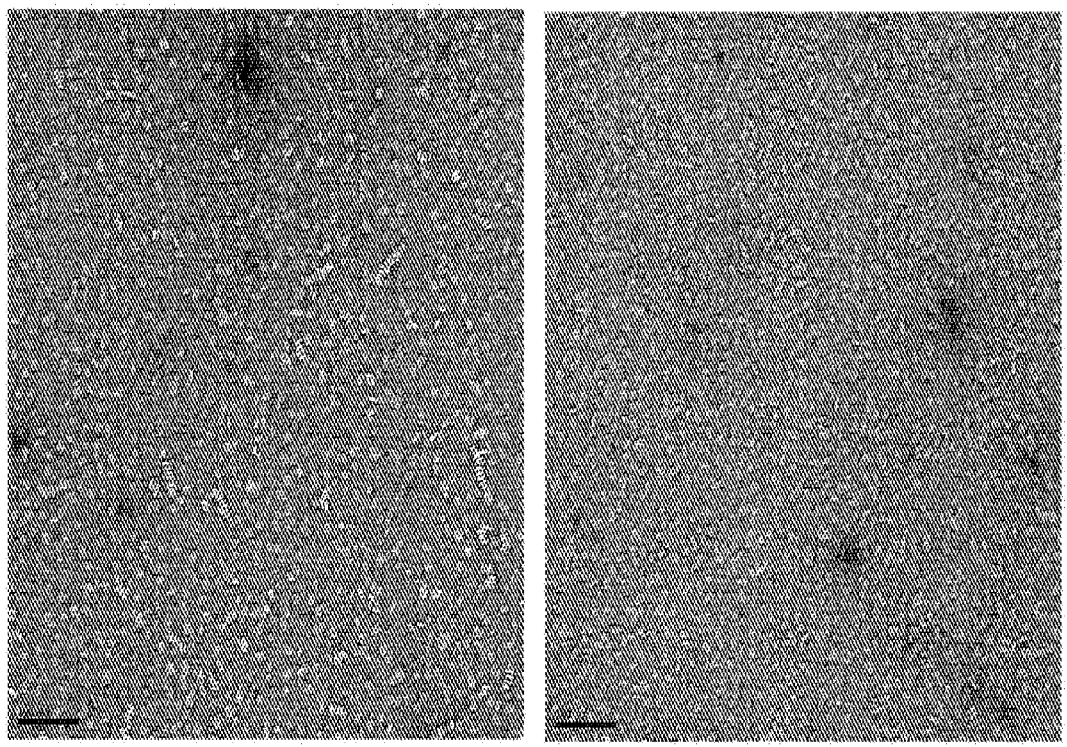
FIG. 3 shows transmission electron microscope (TEM) shape and size analysis of nanoparticles.
Figure 3:
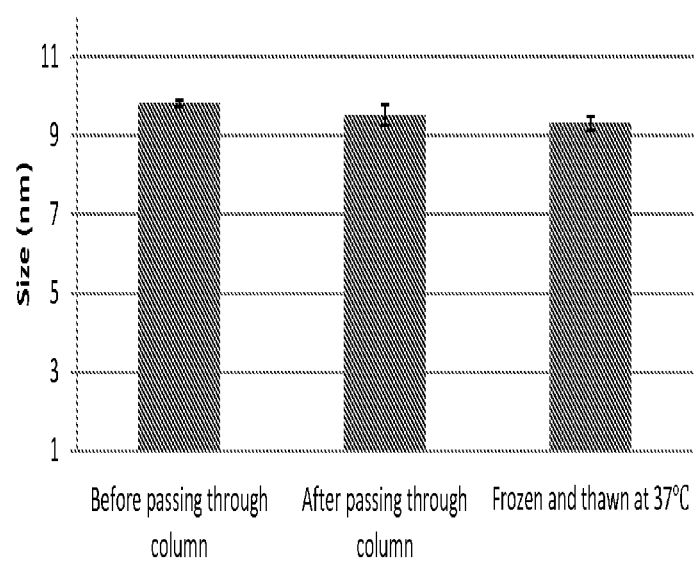

The shape of the sHDL was observed by transmission electron microscope (TEM). Results are shown in FIG. 3.

Example 4

Release Profile of Drug from sHDL

Figure 4:
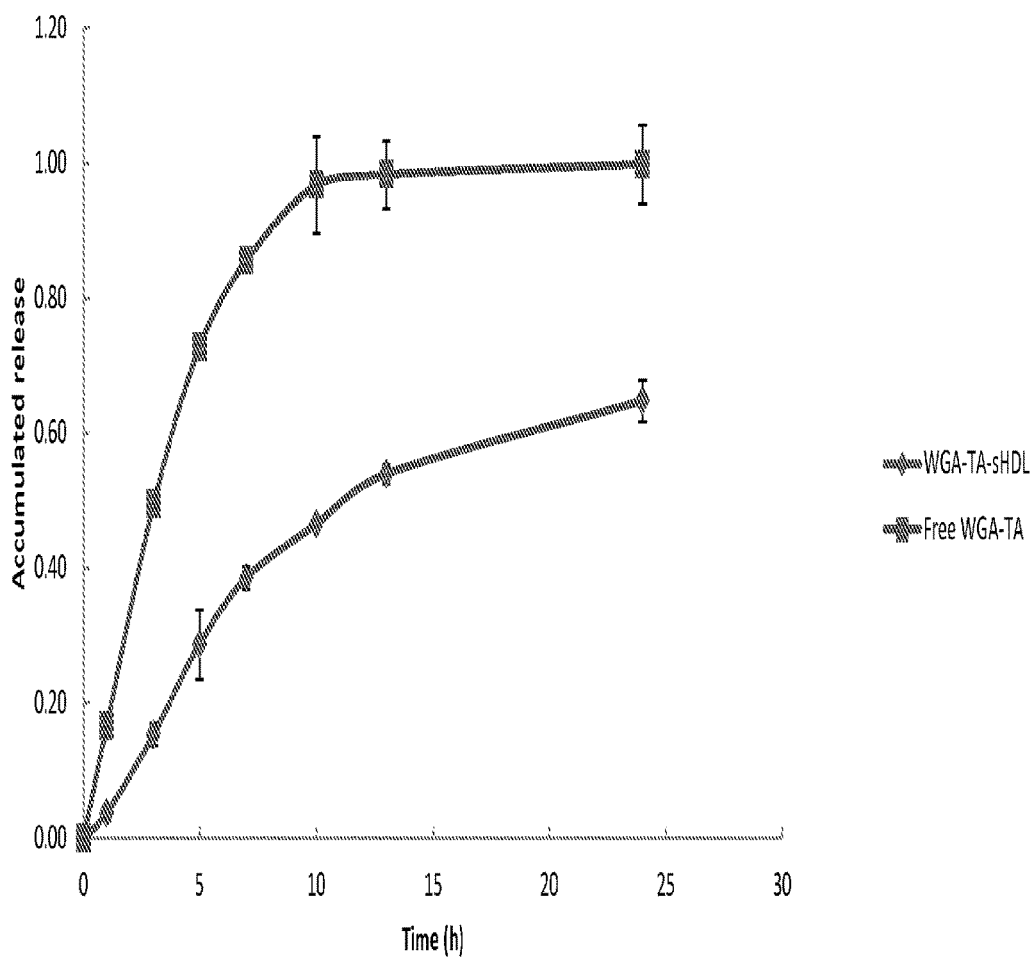
FIG. 4 shows data for the release provide of drug from sHDL.

WGA-TA-loaded sHDL or free drug was added into a dialysis bag (6-8 kda), which was put in 200 ml PBS (pH 7.4) containing 0.1% Tween 80. The release medium was put in a 37° C. air bath shaker with gentle shaking at 100 rpm. At predetermined time points, 2 ml of the medium was sampled and equal volume of fresh release media was added back. The amount of drug in the media was quantified by reverse-phase HPLC using the above-mentioned condition. Results are shown in FIG. 4.

Example 5

In Vitro Efficacy Testing

Figure 5:
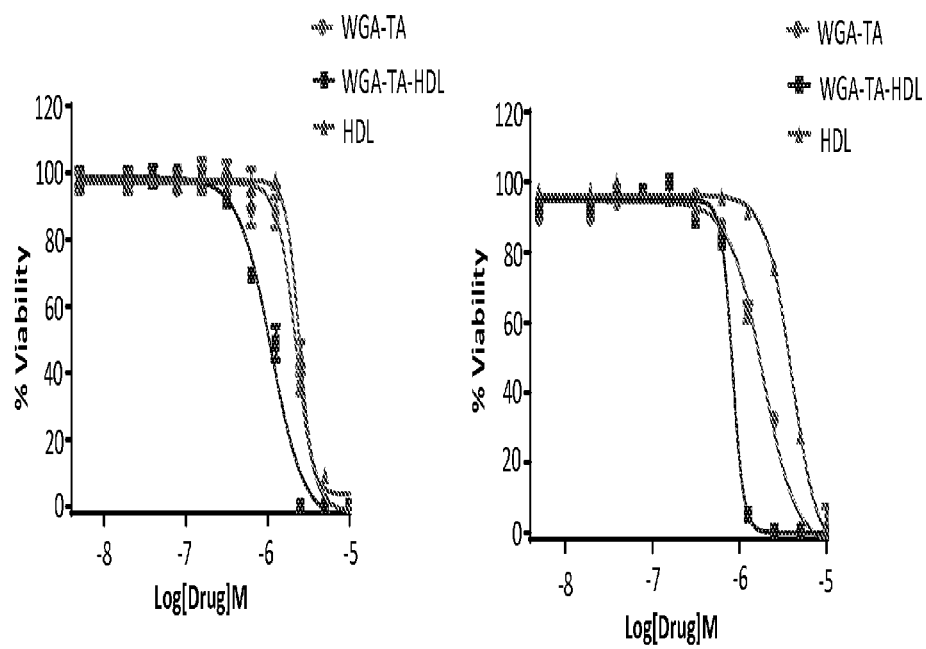
FIG. 5 shows in vitro efficacy testing of nanoparticles.
Figure 5:
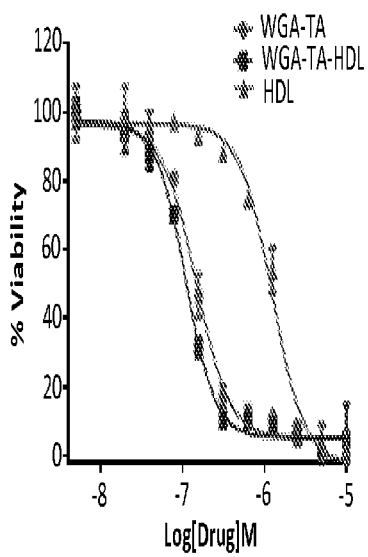

For in vitro testing of drug efficacy, two adrenocortical carcinoma cell lines (AQCC) SW13 and H295R and two neuroblastoma cells lines (NB) were used and the viability was determined by Cell Titer Glo Cell proliferation assay. Approximately 4000-8000 cells per well were seeded in a 96-well micro titer plates in 100 µL of growth media and was allowed to attach overnight. On the second day, serial dilutions of the sHDL nanoparticle, WGA-TA (4,19,27-with alongolide A triacetate) and sHDL-WGA-TA were added in replicates of three to the plates. The cells were then incubated for 72 h at 37° C. in a $CO_2$ humidified chamber. Viability of cells was then measured based on quantification of the ATP levels after treatment with CellTiter-Glo luminescent assay reagents as per the manufacturer's protocol (Promega, Madison, Wis.) with luminescence quantified using a BioTek Synergy Neo plate reader (BioTex, Winooski, Vt.). All experiments were carried out at three independent time points and the viability of the cells was expressed as the ratio of the number of viable cells with treatment compared to control untreated cells. The half-maximal inhibitory concentrations (IC50) were calculated from the MTS assay curves using GraphPad Prism 5 software. In all the cell lines tested, HDL nanoparticle WGA-TA had superior cytotoxic effect compared to either free WGA-TA or HDL. Results are shown in FIG. 5.

Example 6

RT-PCR Analysis of SR-BI

Figure 6:
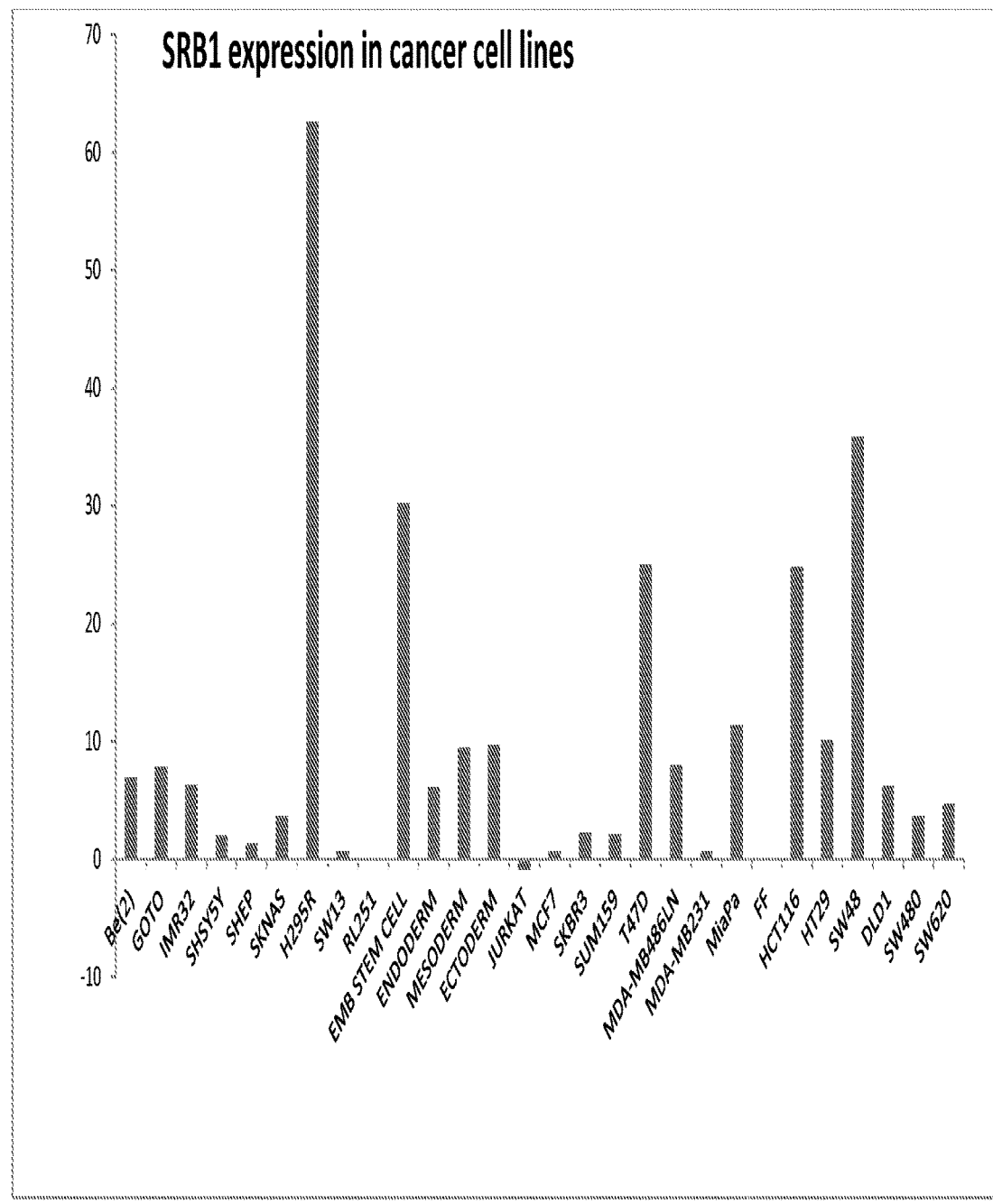
FIG. 6 shows RT-PCR analysis of SR-BI expression from cancer cell lines.

For RT-PCR analysis of SR-BI, RNA was synthesized from cancer cell lines using Qiagen RNA isolation kit. Approximately 1 µg of total RNA was reverse transcribed using Superscript-II reverse transcriptase kit to generate cDNA (Invitrogen). The resulting cDNA was amplified with appropriate primers using power SYBR Green PCR Master Mix and analyzed on a ViiA7 Real-Time PCR system (Life Technologies). Reactions were run in triplicates and GAPDH was used as an internal control to normalize for the variability in expression levels. Data analysis is performed using the 2-$\Delta\Delta CT$ method. The results indicated that the majority of the cancer cells express SR-BI compared to fibroblasts (see FIG. 6).

Example 7

Western Blot Analysis for the Expression of SR-B1

Figure 7:
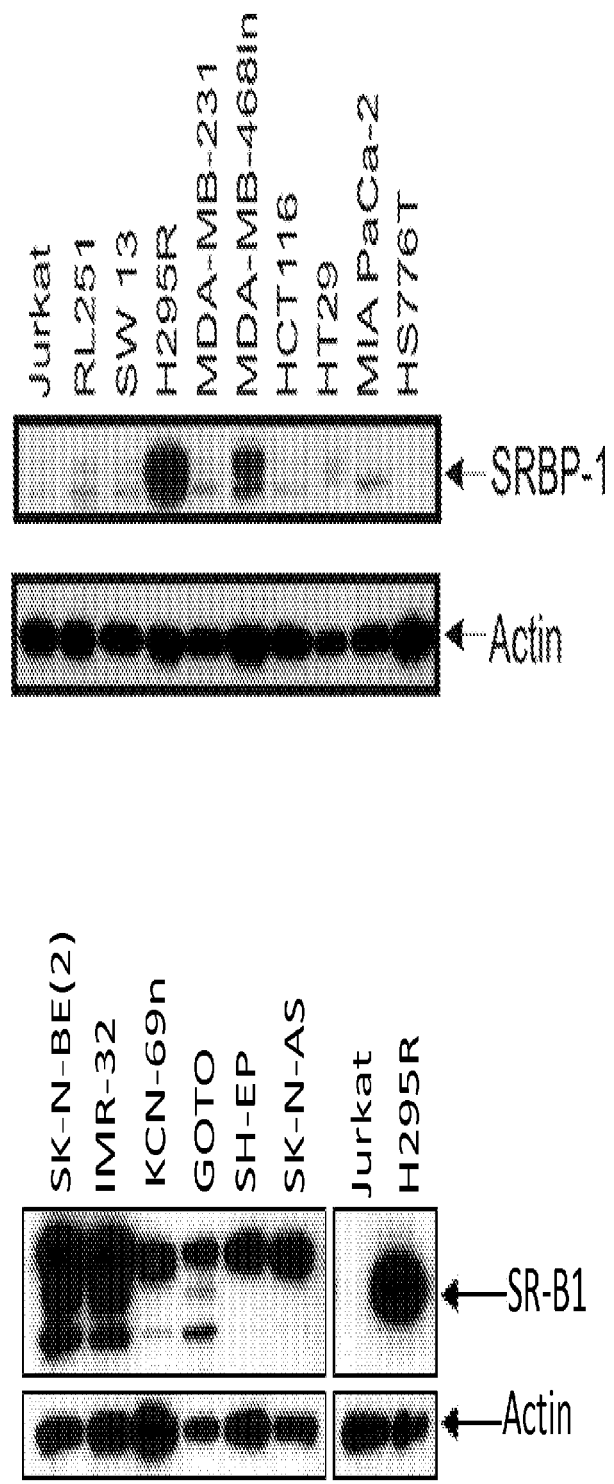
FIG. 7 shows Western blot analysis of SR-BI expression from cancer cell lines.

The cells grown in confluence were lysed using RIPA buffer (50 mM Tris-HCl pH 7.4, 150 mM NaCl, 1% (v/v) NP-40, 0.5% (w/v) sodium deoxycholate, 10 mM sodium fluoride, 1 mM sodium orthovanadate, 1 mM PMSF, 10 mM sodium pyrophosphate, 0.1% (w/v), SDS supplemented with protease inhibitor solution (EMD Millipore, Billerica, Mass.). After lysis the cells were centrifuged at 14,000 rpm for 20 minutes and the proteins were quantified using Protein Assay Reagent (Thermo Scientific, Rockford, Ill.). Equal amounts of proteins were separated using SDS-PAGE and then transferred onto a Hybond nitrocellulose membrane (GE Healthcare Life Sciences, Piscataway, N.J.). The membranes were blocked using 5% milk and probed over night with appropriate dilutions of the primary antibodies (SR-BI or actin) for proteins. The blots were then washed three times with PBST and incubated with 1:5000 dilutions of HRP conjugated secondary antibodies from Santa Cruz Biotechnology (Santa Cruz, Calif.). To ensure equal loading of proteins, actin was used as a control. The bands were visualized using Enhanced chemiluminescence reagent (Thermo Scientific, Rockford, Ill.). The images were captured on Kodak X-ray film. Results are shown in FIG. 7.

Example 8

Nanoparticle Drug Uptake by ACC Cells

Figure 8:
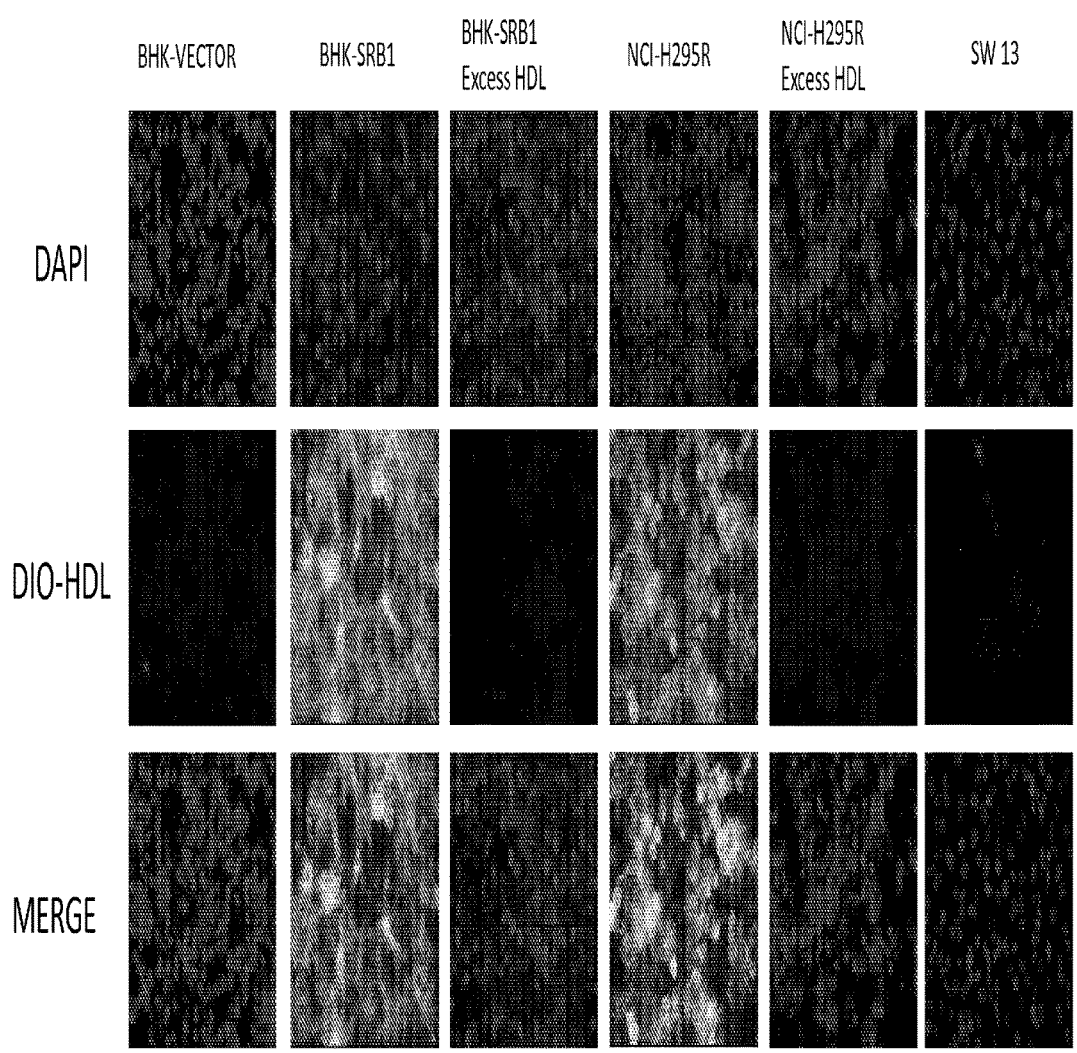
FIG. 8 shows data demonstrating nanoparticle drug uptake in cancer cells.

The ability of cancer cells with various levels of SR-BI to take up the HDL nanoparticles through SR-BI receptor and the effect of HDL composition on internalization of HDL's cargo by SR-BI was examined after a 4 h incubation of cells with the long-chain dialkylcarbocyanines lipophilic tracers DIO (Invitrogen, NY) labeled HDL nanoparticles. The fluorescent images were taken using Nikon fluorescent microscope after fixing the cells with paraformaldehyde. The nuclei were stained with 4', 6-diamidino-2-phenylindole (DAPI) a fluorescent stain binding to DNA. Very high uptake of the HDL nanoparticles was observed in high SR-BI expressors as seen from the fluorescent dye DIO expression. Furthermore, more than 90% of the uptake was successfully blocked by 10 fold excess of HDL. Results are shown in FIG. 8.

Example 9

Biodistribution of sHDL-WGA-TA Nanoparticle in Xenograft with High Levels of SR-BI.

Figure 9:
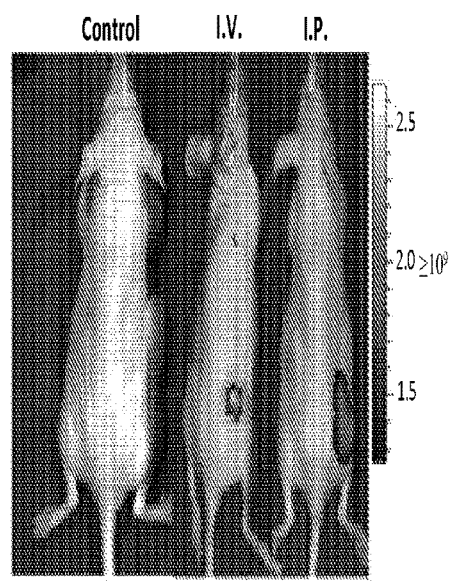
FIG. 9 shows nanoparticle distribution in a cancer xenograft animal model.
Figure 9:
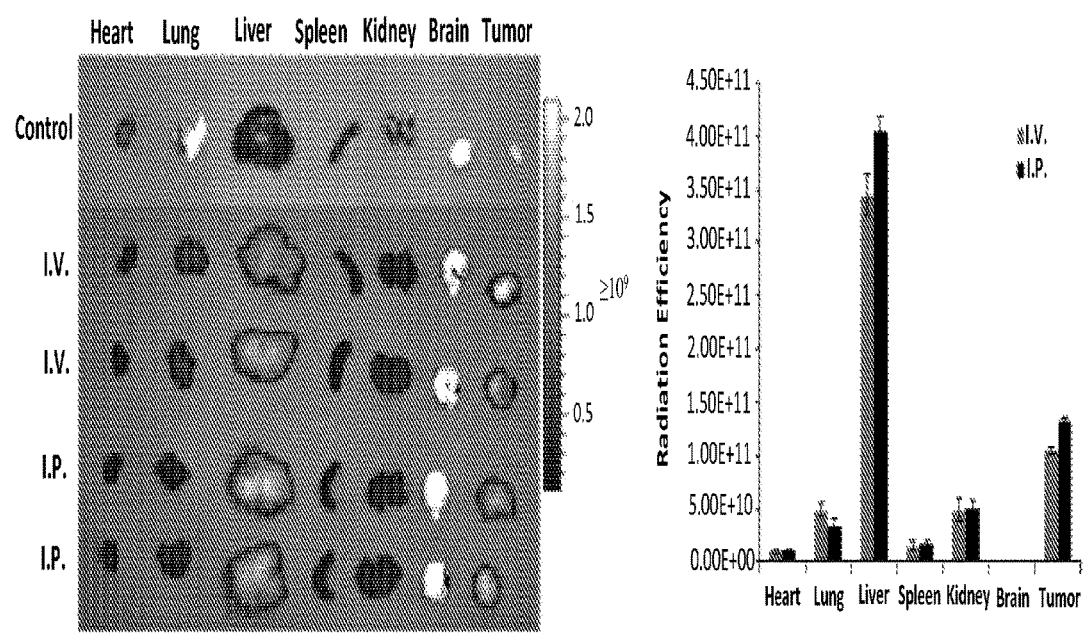

In order to characterize the bio distribution and tumor-targeting efficacy of the sHDL-WGA-TA nanoparticle in vivo, studies were done in the adrenocortical cancer (H295R) cell line that expresses very high levels of SR-BI. Whole-animal imaging of tumor-bearing mice were employed as well as imaging of organs after necroscopy. DiR (Invitrogen, NY) labeled HDL nanoparticles (0.6% DiR) were injected into the tail vein or i.p. at 1 mg per animal dose and the whole body fluorescent imaging was performed at 24 h using a Xenogen IVIS Spectrum Imaging System. At the end of 24 h animals were sacrificed; tumor and tissues including spleen, liver, heart, lung, kidney, brain and tumor were removed, imaged and weighed, for characterizing bio-distribution of the drug. The images shown in FIG. 9 indicated the presence of high levels of HDL nanoparticle in SR-BI expressing tumor tissue with some liver accumulation (although significantly less per mg tissue than tumor) 24 h post dosing.

Example 10

Tumor Targeting Efficacy of sHDL-WGA-TA Nanoparticle in Xenograft with High Levels of SR-BI.

Figure 10:
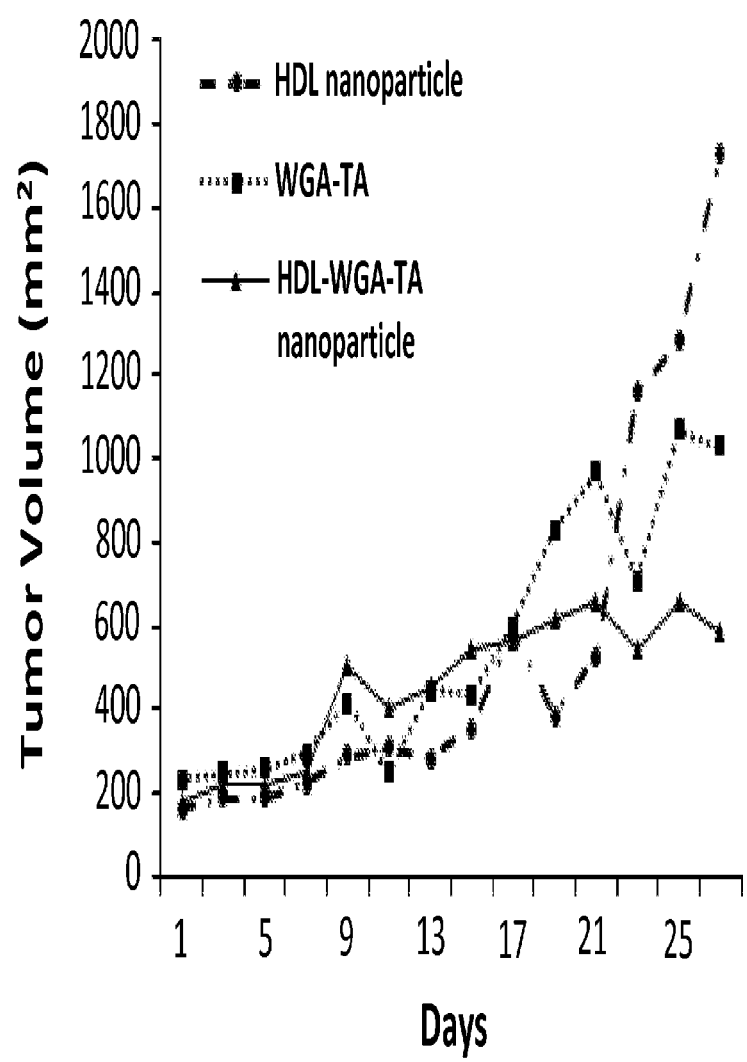
FIG. 10 shows data demonstrating efficacy of nanoparticles in treating cancer in a cancer xenograft animal model.

For developing xenografts, $10 \times 10^6$ H295R cells in 100 μL of PBS was inoculated s.c. at the flank region of the 6-8 week old female Balb/c nude mice. Once tumor volumes reached 30 mm$^3$, mice were randomized into control (PBS treatment) and drug treatment groups of 10 mice each. The mice were injected i.p. with either sHDL nanoparticle alone or WGA-TA alone or sHDL-WGA-TA every other day for 3 weeks at a dose of 3 mg/kg in terms of WGA-TA. Tumor size was measured thrice weekly using a digital caliper (confirmed by two observers). Tumor volume was calculated using the following equation: tumor volume $(mm^3)=(\pi/6) \times (width)^2 \times$ length. Results are shown in FIG. 10, showing superior efficacy of the sHDL-WGA-TA composition.

Example 11

Mouse Adrenal Cortical Carcinoma Xenograft

Human adrenal cortical carcinoma cell line H295R was obtained from the American Type Culture Collection (ATCC; Manassas, Va.). Cells were maintained in 2D culture using 1:1 Dulbecco's modified Eagle medium: Nutrient Mixture F12 (DMEM:F12, Life Technologies, Grand Island, N.Y.) supplemented with 5% fetal bovine serum (Sigma-Aldrich, St. Lewis, Mo.), 100 U/mL penicillin, 100 μg/mL streptomycin (Life Technologies, Grand Island, N.Y.) and 1×ITS (final concentrations 0.001 mg/ml bovine insulin, 0.0055 mg/ml human transferrin and 6.7 ng/ml sodium selenite, Life Technologies, Grand Island, N.Y.). When cells reached 60-70% confluence, cell were collected using 0.25% trypsin-0.02% EDTA (Sigma-Aldrich, St. Lewis, Mo.) and mechanical dissociation, then suspended at $60 \times 10^6$ cells/mL in phosphate buffered saline (PBS) and placed on ice. Within 30 minutes, athymic nude mice (Athymic Nude-Foxn1$^{nu}$, Harlan Laboratories, Indianapolis, Ind.) were anesthetized with isoflourine and $6 \times 10^6$ cells in 100 μL PBS were injected subcutaneously along the right flank. Overall tumor take rate was approximately 80%.

When tumors reached 80-100 mm$^3$ after approximately 4-6 weeks, mice were randomized into one of five experimental arms, with 8 mice per arm. Treatment arms included control vehicle group, 7 mg/kg/day sHDL group, 7 mg/kg/day WGA-TA group, 7 mg/kg/day sHDL-WGA-TA group and lastly the Italian protocol (etoposide, doxorubicin, cisplatin and mitotane) group. Mice were treated with daily intraperitoneal injections for 21 days. Tumor length and width measurements were recorded by digital caliper every 3 days for a total study length of 12 weeks following the start of treatment, or when tumors either exceeded 2000 mm$^3$ or mice became moribund. Two mice from each arm were euthanized for toxicity and histology on study day 21 and 22, at 2 hours and 24 hours following final treatment, respectively. Average tumor volume was calculated using the formula: tumor volume $(mm^3)=(\pi/6) \times (width)^2 \times$ length, and results were displayed as average tumor volume graphed against day of treatment. At 12 weeks, the sHDL-WGA-TA animals had the highest survival.

Example 12

Metabolite Analysis

CD-1 white mice were given an IV dosage of 4 mg/kg WGA-TA in dextran formulation. Samples of blood was collected at different time points in heparin treated tubes and the plasma collected after centrifugation at 13,000 rpm for 10 min and was frozen at −80° C. for later analysis. For the evaluation of metabolites, 300 uL of ice-cold acetonitrile was added to 100 uL of the mouse plasma and then centrifuged at 4° C. in 15000 rpm for 10 minutes. The top supernatant was dried under a stream of nitrogen gas. The residue was finally reconstituted in a 100 uL solution of 20% acetonitrile (80% water). Blank plasma needed for the control was prepared from untreated CD-1 white mice blood as above. As a negative control, blank plasma spiked with WGA-TA before extraction was used. The LC-MS/MS analysis was conducted using a Shimadzu HPLC system coupled with an API 4500 mass spectrometer (Applied Biosystems, MDS Sciex Toronto, Canada), equipped with an API electrospray ionization (ESI) source. Enhanced MS, product ion-scan, and MRM scan were used as a survey scan to identify metabolites of WGA-TA. Information dependent acquisition (IDA) was used to collect fragmentation of metabolite candidates or single experiment of enhanced product ion scan was applied to acquire fragmentation of metabolites after running survey scan. The analytical data were processed by Analyst software (version 1.6; Applied Biosystems, Foster City, Calif., USA). Metabolic identification showed three deacetylation products of WGA-TA at 30 minutes after I.V. administration. The major product identified was the mono deacetylation product (M3) along with minor product M1 and M2 deacetylation products (di and tri deacetylation). Additionally, a product at (M4) at m/z of 258 was also identified.

The LC-MS/MS was operated at positive ESI ionization mode. The ion spray temperature was set at 600° C., spray voltage at 5000 V, curtain gas at 30 psi, both the nebulizer (gas 1) and auxiliary gas (gas 2) was set at 55 psi. Nitrogen was used as the collision gas. The mobile phases consisted of 0.1% formic acid in purified water (A) and 0.1% formic acid in acetonitrile (B). The column used was Xbridge with 2.1 mm ID×100 mm long×3.5 um. The starting gradient (B) was 2% (0-2 min), increased to 45% at 5 min, further increased to 65% at 23 min and finally to 90% at 30 min. After staying at 90% for 3 mins, it was immediately stepped back down to 23% for re-equilibration. Flow rate was set at 0.23 mL/min.

Example 13 pK Study

CD-1 white mice were given IP dosage of 7 mg/kg of either HDL-WGA-TA or WGA-TA in dextran formulation. Samples of blood were collected at different time points and the plasma as well as samples for analysis were prepared as described in metabolite id method. Based on the data HDL-WGA-TA was released much slower than WGA-TA in the i.p. study.

Example 14

Additional Anticancer Agents

The composition as described in Example was made with various anticancer agents in place of WGA-TA. Successful nanoparticle formation and loading was demonstrated with each of 10-hydroxy camptothecin, paclitaxel, docetaxel and CCNU (lomustine).

Docetaxel details are provided below to illustrate the materials and methods.

Materials:

1,2-dipalmitoyl-sn-glycero-3-phosphocholine (DPPC), Sphingomyelin (SM), N-(Carbonyl-methoxypolyethyleneglycol 2000)-1,2-distearoyl-sn-glycero-3-phosphoethanolamine (DSPE-PEG 2000) 22A apoA-I mimetic peptide and docetaxel (DTX), glacial acetic acid, PBS Methods:

Lipids with different ratio together with various DTX loading and 22A peptide were dissolved and well mixed in glacial acetic acid in glass vials. The mixture was then freeze-died to remove the acetic acid. After freeze-drying for at least 24 hours, PBS with proper volume was added into the powder and vortexed the mixture immediately for 30 seconds to form homogenous mixture which was thermos-cycled for 3 times between 50° C. (10 min) and 20° C. (10 min) with gentle shaking to obtain the sHDL loaded with DTX. Then all the samples were kept in 37° C. for 24 hours and the extent of DTX precipitation out from sHDL of each sample was observed and the formulations with less extent of precipitation were chosen to conduct stability test to determine the most stable formulation.

Results:

All the tested formulations and precipitating level were listed in Table 2. All formulations get clear HDL particles right after the thermos-cycle. After 24 hours incubation at 37° C., formulations composed of DPPC only or both DPPC and DSPE-PEG2000 were very unstable which was possibly due to the low phase transition temperature of DPPC which is 41° C. When SM was added to replace DPPC, DTX-sHDL had less precipitation with the same DTX concentration as in DPPC composed DTX-sHDL. The addition of 15% DSPE-PEG2000 did not improve the stability of DTX-sHDL significantly. Formulations from No. 5 to No. 7 have the same lipids composition with various loading of DTX. As DTX concentration increased, more drug precipitated out indicating the overload of drug. At concentration of 0.5 mg/mL, there was almost no precipitation. Based on observed results, formulation No. 1, No. 3, No. 5 and No. 7 were chosen to perform quantified stability test.

TABLE 2

Formulation composition and precipitation of DTX after 24 hours at 37° C.

| Sample Number | Lipid &22A composition | DTX concentration | Precipitation after 24 hr |
|---|---|---|---|
| 1 | DPPC:SM:22A = 10 mg:10 mg:10 mg/mL | 1.0 mg/mL | ++ |
| 2 | DPPC:22A = 20 mg:10 mg/mL | 1.0 mg/mL | +++ |
| 3 | SM:22A:DSPE-PEG2000 = 20 mg:10 mg:1.5 mg/mL | 1.0 mg/mL | ++ |
| 4 | DPPC:22A:DSPE-PEG2000 = 20 mg:10 mg:1.5 mg/mL | 1.0 mg/mL | +++ |
| 5 | SM:22A = 20 mg:10 mg/mL | 1.0 mg/mL | + |
| 6 | SM:22A = 20 mg:10 mg/mL | 1.5 mg/mL | +++ |
| 7 | SM:22A = 20 mg:10 mg/mL | 0.5 mg/mL | − |

DTX-sHDL Stability Test

Materials:

1,2-dipalmitoyl-sn-glycero-3-phosphocholine (DPPC), Sphingomyelin (SM), N-(Carbonyl-methoxypolyethyleneglycol 2000)-1,2-distearoyl-sn-glycero-3-phosphoethanolamine (DSPE-PEG 2000) 22A apoA-I mimetic peptide and docetaxel (DTX), glacial acetic acid, PBS, methanol and acetonitrile Methods:

DTX-sHDL with different lipid composition and drug loadings were prepared as described above. After DTX-sHDL were prepared (4 samples for each formulation), 100 ul solution was drawn off at time points 0, 1, 2, 6, and 24 hours for each sample. The extracted solution was filtered through 0.22 um membrane and 50 ul of the solution was collected. Then 450 ul solvent (methanol:acetonitrile=7:3) was added to the dissolve all the component of DTX-sHDL including peptide, lipids and drug. The mixture was vortexed briefly and centrifuged for 5 min at 8000 rpm. The supernatant was collected for UPLC analysis. The concentration of DTX incorporated in sHDL was determined and the percentage of drug remained in sHDL which didn't release from the sHDL and precipitate out was calculated and normalized to the time point 0 hr.

Figure 11:
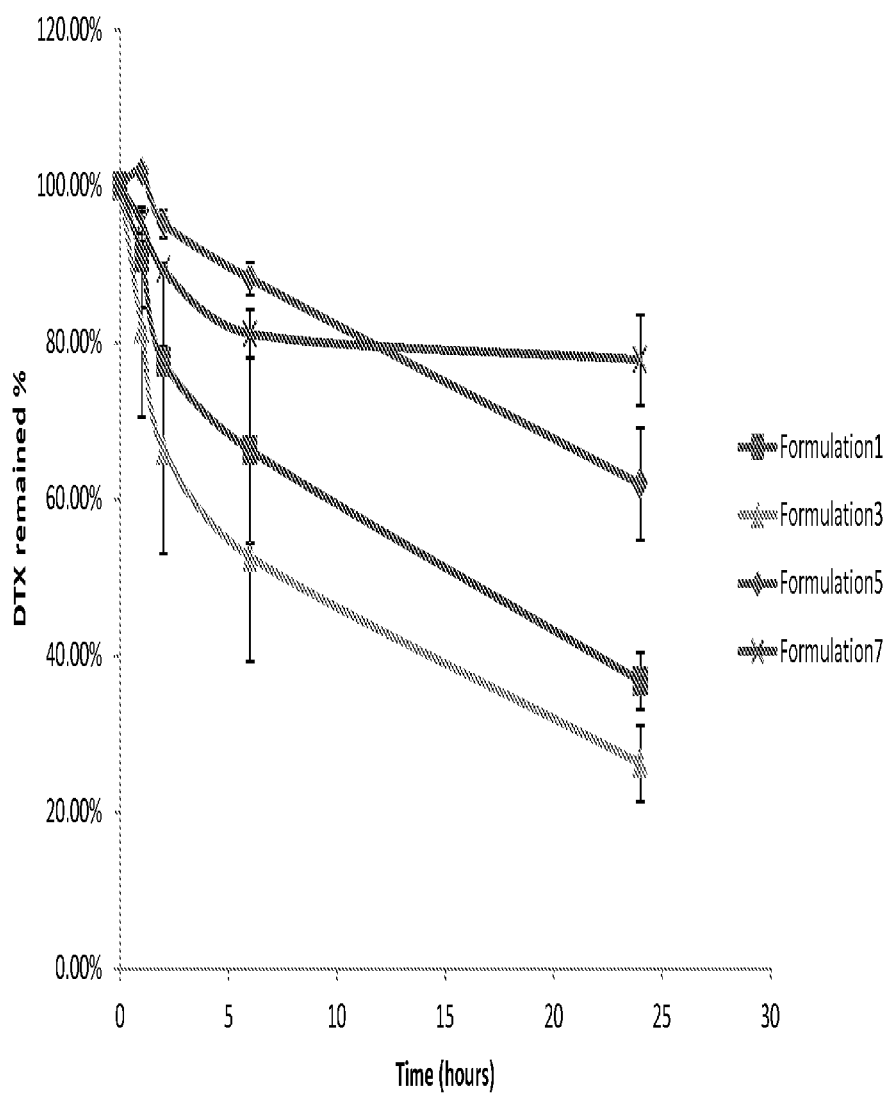
FIG. 11 shows the percentage of DTX remained in sHDL at different time points. Data is shown as average±MSE.

Results:

The percentage of DTX incorporated in sHDL compared to time point 0 hr was shown in FIG. 11. It demonstrated that formulation 3 which was composed of DPPC, SM and DSPE-PEG2000 (1:1:0.15, w/w) was least stable at 37° C. Both of formulation 3 and formulation 1 having DPPC and SM (1:1, w/w) showed a fast release after preparation and had more than 50% drug precipitate out after 24 hours incubation. Formulations with SM as lipid component showed a better stability property. For formulation 7 with less drug loading, a higher percentage of drug remained in sHDL with a little precipitation within 6 hours and stayed stable after.

Example 15

The clinical picture and the prognosis of patients affected by ACC appear to be rather disappointing. Current best-practice treatments involve a multidisciplinary management. The first therapeutic step is typically radical surgery, also in the incidence of isolated metastatic disease. However, the most widely used medical therapy for patients unsuitable for surgery is treatment with mitotane, an insecticide derivative (ortho, para', dichloro-, diphenyl-, dichloroethane) either alone or in combination with chemotherapeutic agents. Unfortunately, given the high toxic effects resulting from mitotane therapy, the response rates are rather low in ACC. Several cytotoxic pharmacological agents, such as cisplatin, etoposide, doxorubicin/adriamycin, vincristine, 5-fluorouracil, and streptozotocin, have been used individually or in a combination regimen in the treatment of patients with late-stage ACCs. To date, the studies that have shown the highest rates of therapeutic response were the so-called "Italian" protocol, consisting of etoposide, doxorubicin, and cisplatin, with concomitant mitotane administration (EDP/M). This example demonstrated improved compositions and methods employing sHDL.

Cell Lines:

Two human ACC cell lines, NCI-H295R (which secretes cortisol) and SW13 (non-steroid secreter) were grown in 2D culture in humidified atmosphere of 5% $CO_2$ in air at 37° C. SW13 cells were grown in Dulbecco Modified Eagle's Medium (DMEM; Life Technologies, Grand Island, N.Y.) supplemented with 10% fetal bovine serum (FBS; Sigma-Aldrich, St. Louis, Mo.) and 1% penicillin/streptomycin (Life Technologies, Grand Island, N.Y.). NCI-H295R cells were grown in DMEM-Ham's F12 nutrient medium (Life Technologies, Grand Island, N.Y.) supplemented with 10% FBS (Sigma-Aldrich, St. Louis, Mo.), 1% insulin/transferrin/selenium (ITS) and 1% penicillin/streptomycin (Life Technologies, Grand Island, N.Y.).

Preparation and Characterization of Synthetic HDL (sHDL):

1,2-dimyristoyl-sn-glycero-3-phosphocholine (DMPC), 1-palmitoyl-2-oleoyl-sn-glycero-3-phosphocholine (POPC), and 22A peptide (Khan et al., Circulation, (2003); 108(17): 563-4, herein incorporated by reference in its entirety) (weight ratio=1:1:1) were dissolved in glacial acetic acid, which was removed by freeze-drying. Phosphate buffered saline (PBS pH=7.4) was added to the freeze-dried powder, which then was cycled 3 times between 50 (3 min) and 20 (3 min) with gentle shaking to obtain the sHDL. sHDL purity was analyzed by gel permeation chromatography (GPC The sHDL was further characterized by transmission electron microscopy (TEM). All images were acquired on JEM 1200EX electron microscope (JEOL USA) equipped with an AMT XR-60 digital camera (Advanced MicroscopyTechniques Corp).

Cell Viability Assay and Calculation of Combination Index:

SW13 and NCI-H295R cells were seeded into 96 well plates in triplicate and were treated with varying concentrations of either chemotherapeutic drugs (cisplatin, doxorubicin, etoposide, mitotane or EDP-M combination) alone or in simultaneous combinations with sHDL or sHDL alone for 72 h. A large dose range was initially used to define a more selective dose range for IC50 experiments. Serial dilutions were made from the starting concentrations and viability of cells was then measured based on quantification of the ATP levels after treatment with CellTiter-Glo luminescent assay reagent as per the manufacturer's instruction (Promega, Madison, Wis.) with luminescence quantified using a BioTek Synergy Neo plate reader (BioTek, Winooski, Vt.). Cell viability ratios were calculated using GraphPad Prism 5 software (GraphPad Software, Inc., La Jolla, Calif.) and the combination index (CI) was calculated using Chou-Talalay equation (Chou and Talalay, Advances in enzyme regulation, 1984; 22:27-55, herein incorporated by reference in its entirety) using CompuSyn software (ComboSyn Inc., Paramus, USA). The CI values of less than 1, equal to 1 and greater than 1 represent synergistic, additive and antagonistic effects respectively. For all cell-based experiments, the experimental control group was defined, unless stated otherwise, as untreated cells or cells treated with single drug alone (when comparing to combination regimens).

Colony Formation Assay:

NCI-H295R and SW13 cells were plated in 6-well plates and allowed to attach. Treatment commenced for 24 h with drug alone or in combination with sHDL (50 µg of sHDL in terms of 22A peptide/ml). Untreated or sHDL alone-treated cells were controls. The medium was changed and surviving cells allowed to grow colonies of 50 cells or more for two weeks, then washed, fixed, and stained with coomassie blue and counted. Total colony numbers were normalized to untreated controls.

Analysis of Apoptosis by Flow Cytometry:

To analyze combination effect on apoptosis, SW13 and NCIH295R cells grown in 60 mm plates and treated with either E, P, M alone or in combination with sHDL for 24 h. Following treatment, cells were washed, re-suspended in annexin binding buffer and stained using annexin V-FITC/Propidium iodide as previously described (Subramanian et al., World J. Surg., 2014, 38(6): 1343-52). Induction of apoptosis was measured using the CyAn ADP Analyzer (Beckman Coulter, Inc., Indianapolis, Ind.).

Mitochondrial Membrane Potential:

SW13 and NCI-H295R were seeded in a 96 well black wall plate. Once attached, they were treated with the drugs as described above. 24 h post drug treatment, 500 nM tetramethylrhodamine, ethyl ester (TMRE) was added and the cells were incubated for 20 minutes at 37° C. and the fluorescent signal was measured after washing using a microplate reader (excitation=549, emission=575). 100 nM FCCP (carbonyl cyanide 4-(trifluoromethoxy)phenylhydrazone) was added to cells 10 minutes before the addition of TMRE as a negative control.

Immunoassay for Cortisol Measurement:

The cortisol immunoassay (Alpco, Salem, N.H.) was used to quantitate cortisol levels in the culture supernatant of steroid producing NCI-H295R cells after treatment with drug combinations (same as in clonogic assay) for 24 h per the manufacturer instructions. Briefly, culture supernatant after treatment was added to the antibody coated-plates containing assay buffer (45 minutes at 25° C.). After washing, tetra methyl benzidine (TMB) substrate was incubated at RT and absorbance measured using a Synergy Neo reader (BioTek, Winooski, Vt.).

mRNA Isolation and Real Time RT-PCR:

RNA from the NCI-H295R cells after drug treatment for 24 h was prepared using Qiagen RNA isolation kit (Qiagen Sciences, Valencia, Calif.). Approximately 500 ng of RNA was reverse transcribed using superscript RT kit from Life Technologies (Grand Island, N.Y.). qPCR was performed in a step-one RT PCR machine using the gene specific primer sets (Table 3) as published (11). Relative gene expression levels were calculated after normalization with internal control. SR-BI expression levels in several cancers was confirmed by Western-Blot Analysis.

mine if synergy of sHDL with EDP-M is possible. As such it was first tested to see if sHDL nanoparticles enhance the antiproliferative effect of E, P and M in ACC cells: Cell-Titer-GLO viability results showed inhibition of cell proliferation in a dose dependent manner for each of the chemotherapeutics drugs. However, sHDL_nanoparticles alone did not induce significant cell death at normal concentrations but only at high_concentrations of 100-200 μg/ml of the 22A peptide. To determine if combining sHDL nanoparticles and the chemotherapeutic drugs results in synergy or an additive effect, the combination index was calculated after treating the cells at different combination dosages using the method of Chou-Talalay (Chou and Talalay, Advances in enzyme regulation, 1984; 22:27-55, herein incorporated by reference in its entirety). Doses were chosen based on the higher IC50 value of mitotane in SW13 cells compared to NCI-H295R cells. A true synergistic effect (combination index <1) was observed at multiple dose ranges combining very low concentrations of sHDL nanoparticles (25 and 50 μg/ml) with cisplatin, etoposide or mitotane but not with doxorubicin (CI >1). In each combination, there was a significant reduction in viability compared to either untreated cells or single

TABLE 3

| Gene | Sense | SEQ ID NO: | Antisense | SEQ ID NO: |
|---|---|---|---|---|
| StAR (NM_000349) | TTGCTTTATGGGCTCAAGAATG | 110 | GGAGACCCTCTGAGATTCTGCTT | 111 |
| CYP11A1 (NM_000781) | CTTCTTCGACCCGGAAAATTT | 112 | CCGGAAGTAGGTGATGTTCTTGT | 113 |
| HSD382 (NM_000198.1) | GCGGCTAATGGGTGGAATCTA | 114 | CCTCATTTATACTGGCAGAAAGGAAT | 115 |
| CYP11B1 (NM_ 000497) | TCCCGAGGGCCTCTAGGA | 116 | GGGACAAGGTCAGCAAGATCTT | 117 |
| CYP11B2 (NM_000498) | TTGTTCAAGCAGCGAGTGTTG | 118 | GCATCCTCGGGACCTTCTC | 119 |
| CYP17A1 (NM_000102) | GCTGACTCTGGCGCACACT | 120 | CCATCCTTGAACAGGGCAA | 121 |
| CYP21A2 (NM_000500) | TCCCAGCACTCAACCAACCT | 122 | CAGCTCAGAATTAAGCCTCAATCC | 123 |
| CYP19A1 (NM_000103) | ACCAGCATCGTGCCTGAAG | 124 | CCAAGAGAAAAAGGCCAGTGA | 125 |

Three Dimensional Multicellular Aggregate Treatment:

To evaluate the translational potential of the combination therapy, three-dimensional multicellular aggregates were developed to mimic the in vivo tumor model as described by Jain et al. (Jain et al., Endocrine-related cancer. 2013 June; 20(3):361-70, herein incorporated by reference in its entirety). Approximately 50,000 SW13 or 100,000 NCI-H295R cells were plated in 24-well ultralow attachment plates (Corning, NY, USA) to generate MCAs. Once MCAs were generated, they were treated with drugs (concentrations specified in our colony formation assay) with or without 50 μg/ml sHDL nanoparticle for 24 h. Untreated, sHDL alone treated cells served as controls. The MCAs were photographed before and after treatment and the MCAs were quantified by Image J software (NIH) as described by Jain et al.

Results:

The experimental design was to first examine the viability of cells after treatment with combination therapy to deterdrug treated cells. This antiproliferative effect was confirmed by clonogenic assay testing the combination of sHDL nanoparticles with each chemotherapeutic drug. Combination treatments had a higher reduction in viability for NCI-H295R and SW13 cell lines by 11.8 and 20.4% respectively for cisplatin, 44.6% and 39.52% for etoposide, 39.1% and 22.3% for mitotane compared to single drug alone (p<0.05 for each). HDL treatment alone had minimal effect.

With synergy observed in combination with several of the drug compounds in inhibiting cell viability, it was next evaluated to determine whether this effect was due to induction of apoptosis or merely a toxic effect of the drug leading to cell necrosis.

sHDL synergizes with chemotherapeutic drugs to induce apoptosis: Next combination dosing was evaluated by flow cytometry for a synergistic effect on apoptotic cell death in both ACC cell lines as determined by analysis of DNA fragmentation using subtoxic concentrations of E, P, or M alone or in combination with sHDL for 24 h. Given the antagonistic effect of doxorubicin with sHDL on proliferation, this combination was not tested. Cells undergoing early as well as late apoptosis and necrosis were differentiated based on phosphatidylserine staining on the outer leaflet of the apoptotic cells by Annexin V-FITC. Combination treatments with sHDL resulted in a significantly greater increase in apoptotic or necrotic cells compared to each drug alone with negligible cell death noted with sHDL alone or untreated cells. The sHDL nanoparticles in combination with chemo drugs resulted in an increase in the percentage of apoptotic cells (early and late) by 6.16%, 36.46%, and 36.01% for P, E and M, respectively ($p<0.05$ vs. drug alone) with minimal changes in necrosis compared to single drug alone for the NCI-H295R cells. In the case of SW13 cells which do not secrete cortisol, the necrotic cell death increased by 14.71% for P and 21.33% for E ($p<0.01$) while the apoptotic cell death increased by 11.9% ($p<0.05$) for M when combined with sHDL vs. drug alone.

Given this synergistic effect on cell growth and induction of apoptosis, and since apoptosis and necrosis are mitochondrial dependent pathways, mitotchondrial membrane potential was assessed.

Mitochondrial membrane potential is altered by combination therapy with sHDL: To elucidate the role of mitochondrial function in inducing apoptosis, the mitochondrial potential ($\Delta\Psi$) was evaluated using TMRE staining after treatment of cells with sHDL and E, P, or M for 24 h. As a negative control the cells were pretreated with an ionophore FCCP to eliminate mitochondrial membrane potential changes. Although treatment of cells with chemo drugs alone at concentrations we have used showed slight increase in mitochondrial membrane potential, combination therapy in NCI-H295R and SW13 cells resulted in a significant reduction in $\Delta\Psi$ by 13.09% and 6.5% for P, 9.2% and 31.54% for E, and 14.49% and 19.8% for M ($p<0.05$ vs. drug alone). This effect was blocked in the presence of mitochondrial depolarizer FCCP.

The effect of combination therapy with sHDL on cortisol levels: To verify how changes in the steroidogenic pathway are influenced by combination therapy, the concentration of cortisol was measured in the culture supernatant of hormone-producing NCI-H295R cells after E, P or M treatment alone or in combination with sHDL for 24 h. Treatment of cells with drug alone decreased cortisol production levels by 89.6% for sHDL, 84.7% for M, and 82.1% for E ($p<0.01$ each vs. controls while P decreased it only by 8.39% (p=NS). In combination with sHDL, this effect was not significantly different for E, or M but decreased 82% with P similar to that seen for the HDL alone. Next, since cortisol levels were significantly decreased with sHDL, this was further assesses to determine its mechanistic effect on steroidogenesis in these ACC cells. To explore the effect of combination treatment on steroidogenesis, the expression of genes involved in steroidogenesis was evaluated by quantitative real time PCR after 24 h treatment of hormone producing NCI-H295R cells with either drug alone or in combination with sHDL (primers listed in Table 3). Relative expression levels of factors of cortisol biosynthesis by RT-qPCR including steroidogenic acute regulatory protein (StAR), the intra mitochondrial cholesterol transporter, CYP11A1 and others were examined. During combination with sHDL and cisplatin or etoposide or mitotane the levels of StAR (0.18-1.88), CYP21A2 (0.05-2.6) and CYP19A1 (0.22-4.9) increases (in terms of fold changes); whereas the levels of CYP11A1 (0.1-0.5), CYP11B1 (0.1-0.64), CYP11B2 (0.04-0.52), CYP17A1 (0.1-0.58) and HSD3B2 (0.1-0.2 for P and M respectively; but increased by 2.1 for E) decreased as fold change. Representative fold changes for enzymes are shown, compared to monotherapy ($p<0.05$).

Combination therapy with sHDL is effective in targeting in vivo mimicking MCAs: To confirm whether the cytotoxic effect of combination therapy in targeting cells can be translated to tumors in vivo, three-dimensional MCAs were used as a mimic for tumor model. First, MCAs were developed by seeding the cells in ultralow attachment plates and then treating them with either drugs alone or in combination with sHDL. Approximately 20%, 50% and 30% reduction in NCI-H295R MCAs was observed for cisplatin, etoposide and mitotane and approximately 50%, 25% and 50% reduction in SW13 MCAs respectively when used in combination with sHDL. These results indicate that sHDL combination is effective in targeting even three dimensional MCAs.

Combination therapy enhances the efficacy of EDPM: Given the antagonistic effect for doxorubicin, it was examined whether the complete EDPM regimen with sHDL would still be synergistic in inhibiting ACC cell viability. The viability of the cells was determined as before by CellTiter-Glo after treating both NCIH295R and SW13 cells with either EDPM (25%, 50%, 75%, or 100% MTD levels) alone or in combination with 25 µg/ml or 50 µg/ml of sHDL. Untreated cells or sHDL alone treated cells served as control. Despite the antagonistic effect of doxorubicin, dose dependent enhanced decrease in viability for both NCI-H295R and SW13 was observed for sHDL combinations compared to EDP-M alone. These results clearly demonstrate that combination therapy with sHDL nanoparticles effectively target ACC cells at much lower doses of EDP-M. As such, it is contemplated that such compositions and methods lower toxicity profiles of these compounds and their combinations.

In conclusion, the results demonstrate that sHDL nanoparticles act synergistically with chemotherapy agents used in ACC, allowing lower doses in combination to generate efficacy. While the invention is not limited by any particular mechanisms of action and the invention can be practiced without understanding a mechanism of action, it is contemplated that this synergy may be due in part to targeting of the steroidogenic pathway, similar to mitotane, in potentiating enhanced apoptosis. Since these sHDL nanoparticles have already demonstrated safety in clinical trials for other indications, this combination strategy provides a novel, less toxic approach to improve treatment in combination and avoid dose-limiting toxicities while maintaining the therapeutic benefits of mitotane and the Italian protocol.

All publications and patents mentioned in the above specification are herein incorporated by reference as if expressly set forth herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

We claim:

1. A composition comprising a nanoparticle comprising a withanolide compound, wherein said nanoparticle comprises high density lipoprotein (HDL).

2. The composition of claim 1, formulated for pharmaceutical administration to a subject.

3. The composition of claim 1, wherein said HDL is synthetic HDL (sHDL).

4. The composition of claim 3, wherein said synthetic HDL comprises a synthetic ApoA-I mimic.

5. The composition of claim 4, wherein said ApoA-I mimic comprises the sequence $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$-$X_{20}$-$X_{21}$-$X_{22}$ (SEQ ID NO:4) wherein: $X_1$ is Pro (P), Ala (A), Gly (G), Gln (Q), Asn (N), Asp (D) or D-Pro (p); $X_2$ is an aliphatic amino acid; $X_3$ is Leu (L) or Phe (F); $X_4$ is Glu (E); $X_5$ is an aliphatic amino acid; $X_6$ is Leu (L) or Phe (F); $X_7$ is Glu (E) or Leu (L); $X_8$ is Asn (N) or Gln (Q); $X_9$ is Leu (L); $X_{10}$ is Leu (L), Trp (W) or Gly (G); $X_{11}$ is an acidic amino acid; $X_{12}$ is Arg (R); $X_{13}$ is Leu (L) or Gly (G); $X_{14}$ is Leu (L), Phe (F) or Gly (G); $X_{15}$ is Asp (D); $X_{16}$ is Ala (A); $X_{17}$ is Leu (L); $X_{18}$ is Asn (N) or Gln (Q); $X_{19}$ is a basic amino acid; $X_{20}$ is a basic amino acid; $X_{21}$ is Leu (L); and $X_{22}$ is a basic amino acid.

6. The composition of claim 5, wherein said ApoA-I mimic is SEQ ID NO:35.

7. The composition of claim 1, wherein said withanolide compound is 4, 19, 27-triacetyl withalongolide A.

* * * * *

SEQUENCE LISTING

```
<160> NUMBER OF SEQ ID NOS: 125

<210> SEQ ID NO 1
<211> LENGTH: 22
<212> TYPE: PRT
<213> ORGANISM: Artificial sequence
<220> FEATURE:
<223> OTHER INFORMATION: Synthetic

<400> SEQUENCE: 1

Pro Val Leu Asp Glu Phe Arg Glu Lys Leu Asn Glu Glu Leu Glu Ala
1               5                   10                  15

Leu Lys Gln Lys Leu Lys
            20

<210> SEQ ID NO 2
<211> LENGTH: 22
<212> TYPE: PRT
<213> ORGANISM: Homo sapiens

<400> SEQUENCE: 2

Pro Val Leu Glu Leu Phe Glu Asn Leu Leu Glu Arg Leu Leu Asp Ala
1               5                   10                  15

Leu Gln Lys Lys Leu Lys
            20

<210> SEQ ID NO 3
<211> LENGTH: 22
<212> TYPE: PRT
<213> ORGANISM: Artificial sequence
<220> FEATURE:
<223> OTHER INFORMATION: Synthetic

<400> SEQUENCE: 3

Pro Val Leu Glu Leu Phe Glu Asn Leu Leu Glu Arg Leu Leu Asp Ala
1               5                   10                  15

Leu Gln Lys Lys Leu Lys
            20

<210> SEQ ID NO 4
<211> LENGTH: 22
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Pro (P), Ala (A), Gly (G), Gln (Q), Asn
      (N), Asp (D) or D-Pro (p)
<220> FEATURE:
<221> NAME/KEY: MISC_FEATURE
<222> LOCATION: (2)..(2)
<223> OTHER INFORMATION: Xaa = an aliphatic amino acid
<220> FEATURE:
<221> NAME/KEY: MISC_FEATURE
<222> LOCATION: (3)..(3)
<223> OTHER INFORMATION: Xaa = Leu (L) or Phe (F)
<220> FEATURE:
<221> NAME/KEY: MISC_FEATURE
<222> LOCATION: (4)..(4)
<223> OTHER INFORMATION: Xaa = Glu (E)
<220> FEATURE:
<221> NAME/KEY: MISC_FEATURE
<222> LOCATION: (5)..(5)
<223> OTHER INFORMATION: Xaa = an aliphatic amino acid
<220> FEATURE:
<221> NAME/KEY: MISC_FEATURE
<222> LOCATION: (6)..(6)
```

```
<223> OTHER INFORMATION: Xaa = Leu (L) or Phe (F)
<220> FEATURE:
<221> NAME/KEY: MISC_FEATURE
<222> LOCATION: (7)..(7)
<223> OTHER INFORMATION: Xaa = Glu (E) or Leu (L)
<220> FEATURE:
<221> NAME/KEY: MISC_FEATURE
<222> LOCATION: (8)..(8)
<223> OTHER INFORMATION: Xaa = Asn (N) or Gln (Q)
<220> FEATURE:
<221> NAME/KEY: MISC_FEATURE
<222> LOCATION: (9)..(9)
<223> OTHER INFORMATION: Xaa = Leu (L)
<220> FEATURE:
<221> NAME/KEY: MISC_FEATURE
<222> LOCATION: (10)..(10)
<223> OTHER INFORMATION: Xaa = Leu (L), Trp (W) or Gly (G)
<220> FEATURE:
<221> NAME/KEY: MISC_FEATURE
<222> LOCATION: (11)..(11)
<223> OTHER INFORMATION: Xaa = an acidic amino acid
<220> FEATURE:
<221> NAME/KEY: MISC_FEATURE
<222> LOCATION: (12)..(12)
<223> OTHER INFORMATION: Xaa = Arg (R)
<220> FEATURE:
<221> NAME/KEY: MISC_FEATURE
<222> LOCATION: (13)..(13)
<223> OTHER INFORMATION: Xaa = Leu (L) or Gly (G);
<220> FEATURE:
<221> NAME/KEY: MISC_FEATURE
<222> LOCATION: (14)..(14)
<223> OTHER INFORMATION: Xaa = Leu (L), Phe (F) or Gly (G)
<220> FEATURE:
<221> NAME/KEY: MISC_FEATURE
<222> LOCATION: (15)..(15)
<223> OTHER INFORMATION: Xaa = Asp (D)
<220> FEATURE:
<221> NAME/KEY: MISC_FEATURE
<222> LOCATION: (16)..(16)
<223> OTHER INFORMATION: Xaa = Ala (A)
<220> FEATURE:
<221> NAME/KEY: MISC_FEATURE
<222> LOCATION: (17)..(17)
<223> OTHER INFORMATION: Xaa = Leu (L)
<220> FEATURE:
<221> NAME/KEY: MISC_FEATURE
<222> LOCATION: (18)..(18)
<223> OTHER INFORMATION: Xaa = Asn (N) or Gln (Q)
<220> FEATURE:
<221> NAME/KEY: MISC_FEATURE
<222> LOCATION: (19)..(19)
<223> OTHER INFORMATION: Xaa = a basic amino acid
<220> FEATURE:
<221> NAME/KEY: MISC_FEATURE
<222> LOCATION: (20)..(20)
<223> OTHER INFORMATION: Xaa = a basic amino acid
<220> FEATURE:
<221> NAME/KEY: MISC_FEATURE
<222> LOCATION: (21)..(21)
<223> OTHER INFORMATION: Xaa =  Leu (L)
<220> FEATURE:
<221> NAME/KEY: MISC_FEATURE
<222> LOCATION: (22)..(22)
<223> OTHER INFORMATION: Xaa =  a basic amino acid

<400> SEQUENCE: 4

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 5
<211> LENGTH: 22
<212> TYPE: PRT
<213> ORGANISM: Artificial sequence
```

<220> FEATURE:
<223> OTHER INFORMATION: Synthetic

<400> SEQUENCE: 5

Pro Val Leu Glu Leu Phe Glu Asn Leu Leu Glu Arg Gly Leu Asp Ala
1               5                   10                  15

Leu Gln Lys Lys Leu Lys
            20

<210> SEQ ID NO 6
<211> LENGTH: 22
<212> TYPE: PRT
<213> ORGANISM: Artificial sequence
<220> FEATURE:
<223> OTHER INFORMATION: Synthetic

<400> SEQUENCE: 6

Pro Val Leu Glu Leu Phe Glu Asn Leu Leu Glu Arg Leu Gly Asp Ala
1               5                   10                  15

Leu Gln Lys Lys Leu Lys
            20

<210> SEQ ID NO 7
<211> LENGTH: 22
<212> TYPE: PRT
<213> ORGANISM: Artificial sequence
<220> FEATURE:
<223> OTHER INFORMATION: Synthetic

<400> SEQUENCE: 7

Pro Val Leu Glu Leu Phe Glu Asn Leu Gly Glu Arg Leu Leu Asp Ala
1               5                   10                  15

Leu Gln Lys Lys Leu Lys
            20

<210> SEQ ID NO 8
<211> LENGTH: 22
<212> TYPE: PRT
<213> ORGANISM: Artificial sequence
<220> FEATURE:
<223> OTHER INFORMATION: Synthetic

<400> SEQUENCE: 8

Pro Val Leu Glu Leu Phe Leu Asn Leu Trp Glu Arg Leu Leu Asp Ala
1               5                   10                  15

Leu Gln Lys Lys Leu Lys
            20

<210> SEQ ID NO 9
<211> LENGTH: 22
<212> TYPE: PRT
<213> ORGANISM: Artificial sequence
<220> FEATURE:
<223> OTHER INFORMATION: Synthetic

<400> SEQUENCE: 9

Gly Val Leu Glu Leu Phe Glu Asn Leu Leu Glu Arg Leu Leu Asp Ala
1               5                   10                  15

Leu Gln Lys Lys Leu Lys
            20

<210> SEQ ID NO 10
<211> LENGTH: 22
<212> TYPE: PRT

```
<213> ORGANISM: Artificial sequence
<220> FEATURE:
<223> OTHER INFORMATION: Synthetic

<400> SEQUENCE: 10

Pro Val Leu Glu Leu Phe Glu Asn Leu Leu Glu Arg Leu Phe Asp Ala
1               5                   10                  15

Leu Gln Lys Lys Leu Lys
            20

<210> SEQ ID NO 11
<211> LENGTH: 22
<212> TYPE: PRT
<213> ORGANISM: Artificial sequence
<220> FEATURE:
<223> OTHER INFORMATION: Synthetic

<400> SEQUENCE: 11

Pro Val Leu Glu Leu Phe Glu Asn Leu Trp Glu Arg Leu Leu Asp Ala
1               5                   10                  15

Leu Gln Lys Lys Leu Lys
            20

<210> SEQ ID NO 12
<211> LENGTH: 22
<212> TYPE: PRT
<213> ORGANISM: Artificial sequence
<220> FEATURE:
<223> OTHER INFORMATION: Synthetic

<400> SEQUENCE: 12

Pro Leu Leu Glu Leu Phe Glu Asn Leu Leu Glu Arg Leu Leu Asp Ala
1               5                   10                  15

Leu Gln Lys Lys Leu Lys
            20

<210> SEQ ID NO 13
<211> LENGTH: 22
<212> TYPE: PRT
<213> ORGANISM: Artificial sequence
<220> FEATURE:
<223> OTHER INFORMATION: Synthetic

<400> SEQUENCE: 13

Pro Val Phe Glu Leu Phe Glu Asn Leu Leu Glu Arg Leu Leu Asp Ala
1               5                   10                  15

Leu Gln Lys Lys Leu Lys
            20

<210> SEQ ID NO 14
<211> LENGTH: 22
<212> TYPE: PRT
<213> ORGANISM: Artificial sequence
<220> FEATURE:
<223> OTHER INFORMATION: Synthetic

<400> SEQUENCE: 14

Ala Val Leu Glu Leu Phe Glu Asn Leu Leu Glu Arg Leu Leu Asp Ala
1               5                   10                  15

Leu Gln Lys Lys Leu Lys
            20

<210> SEQ ID NO 15
<211> LENGTH: 22
```

```
<212> TYPE: PRT
<213> ORGANISM: Artificial sequence
<220> FEATURE:
<223> OTHER INFORMATION: Synthetic

<400> SEQUENCE: 15

Pro Val Leu Glu Leu Phe Leu Asn Leu Trp Glu Arg Leu Leu Asp Ala
1               5                   10                  15

Leu Gln Lys Lys Leu Lys
            20

<210> SEQ ID NO 16
<211> LENGTH: 22
<212> TYPE: PRT
<213> ORGANISM: Artificial sequence
<220> FEATURE:
<223> OTHER INFORMATION: Synthetic

<400> SEQUENCE: 16

Pro Val Leu Glu Leu Phe Glu Gln Leu Leu Glu Arg Leu Leu Asp Ala
1               5                   10                  15

Leu Gln Lys Lys Leu Lys
            20

<210> SEQ ID NO 17
<211> LENGTH: 22
<212> TYPE: PRT
<213> ORGANISM: Artificial sequence
<220> FEATURE:
<223> OTHER INFORMATION: Synthetic

<400> SEQUENCE: 17

Pro Val Leu Glu Leu Phe Glu Asn Leu Leu Glu Arg Leu Leu Asp Ala
1               5                   10                  15

Leu Asn Lys Lys Leu Lys
            20

<210> SEQ ID NO 18
<211> LENGTH: 22
<212> TYPE: PRT
<213> ORGANISM: Artificial sequence
<220> FEATURE:
<223> OTHER INFORMATION: Synthetic

<400> SEQUENCE: 18

Pro Val Leu Glu Leu Phe Glu Asn Leu Asp Arg Leu Leu Asp Ala
1               5                   10                  15

Leu Gln Lys Lys Leu Lys
            20

<210> SEQ ID NO 19
<211> LENGTH: 22
<212> TYPE: PRT
<213> ORGANISM: Artificial sequence
<220> FEATURE:
<223> OTHER INFORMATION: Synthetic

<400> SEQUENCE: 19

Asp Val Leu Glu Leu Phe Glu Asn Leu Leu Glu Arg Leu Leu Asp Ala
1               5                   10                  15

Leu Gln Lys Lys Leu Lys
            20

<210> SEQ ID NO 20
```

```
<211> LENGTH: 22
<212> TYPE: PRT
<213> ORGANISM: Artificial sequence
<220> FEATURE:
<223> OTHER INFORMATION: Synthetic

<400> SEQUENCE: 20

Pro Val Leu Asp Glu Phe Arg Glu Lys Leu Asn Glu Ala Leu Glu Ala
1               5                   10                  15

Leu Lys Gln Lys Leu Lys
            20

<210> SEQ ID NO 21
<211> LENGTH: 22
<212> TYPE: PRT
<213> ORGANISM: Artificial sequence
<220> FEATURE:
<223> OTHER INFORMATION: Synthetic

<400> SEQUENCE: 21

Pro Val Leu Asp Glu Phe Arg Glu Lys Leu Asn Glu Arg Leu Glu Ala
1               5                   10                  15

Leu Lys Gln Lys Leu Lys
            20

<210> SEQ ID NO 22
<211> LENGTH: 18
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (14)..(14)
<223> OTHER INFORMATION: Xaa = Pyrrolysine

<400> SEQUENCE: 22

Leu Asp Asp Leu Leu Gln Lys Trp Ala Glu Ala Phe Asn Xaa Leu Leu
1               5                   10                  15

Lys Lys

<210> SEQ ID NO 23
<211> LENGTH: 18
<212> TYPE: PRT
<213> ORGANISM: Artificial sequence
<220> FEATURE:
<223> OTHER INFORMATION: Synthetic

<400> SEQUENCE: 23

Glu Trp Leu Lys Ala Phe Tyr Glu Lys Val Leu Glu Lys Leu Lys Glu
1               5                   10                  15

Leu Phe

<210> SEQ ID NO 24
<211> LENGTH: 18
<212> TYPE: PRT
<213> ORGANISM: Artificial sequence
<220> FEATURE:
<223> OTHER INFORMATION: Synthetic

<400> SEQUENCE: 24

Asp Trp Phe Lys Ala Phe Tyr Asp Lys Val Phe Glu Lys Phe Lys Glu
1               5                   10                  15

Phe Phe
```

```
<210> SEQ ID NO 25
<211> LENGTH: 18
<212> TYPE: PRT
<213> ORGANISM: Artificial sequence
<220> FEATURE:
<223> OTHER INFORMATION: Synthetic

<400> SEQUENCE: 25

Gly Ile Lys Lys Phe Leu Gly Ser Ile Trp Lys Phe Ile Lys Ala Phe
1               5                   10                  15

Val Gly

<210> SEQ ID NO 26
<211> LENGTH: 18
<212> TYPE: PRT
<213> ORGANISM: Artificial sequence
<220> FEATURE:
<223> OTHER INFORMATION: Synthetic

<400> SEQUENCE: 26

Asp Trp Phe Lys Ala Phe Tyr Asp Lys Val Ala Glu Lys Phe Lys Glu
1               5                   10                  15

Ala Phe

<210> SEQ ID NO 27
<211> LENGTH: 18
<212> TYPE: PRT
<213> ORGANISM: Artificial sequence
<220> FEATURE:
<223> OTHER INFORMATION: Synthetic

<400> SEQUENCE: 27

Asp Trp Leu Lys Ala Phe Tyr Asp Lys Val Ala Glu Lys Leu Lys Glu
1               5                   10                  15

Ala Phe

<210> SEQ ID NO 28
<211> LENGTH: 18
<212> TYPE: PRT
<213> ORGANISM: Artificial sequence
<220> FEATURE:
<223> OTHER INFORMATION: Synthetic

<400> SEQUENCE: 28

Asp Trp Leu Lys Ala Phe Tyr Asp Lys Val Phe Glu Lys Phe Lys Glu
1               5                   10                  15

Phe Phe

<210> SEQ ID NO 29
<211> LENGTH: 18
<212> TYPE: PRT
<213> ORGANISM: Artificial sequence
<220> FEATURE:
<223> OTHER INFORMATION: Synthetic

<400> SEQUENCE: 29

Glu Trp Leu Glu Ala Phe Tyr Lys Lys Val Leu Glu Lys Leu Lys Glu
1               5                   10                  15

Leu Phe

<210> SEQ ID NO 30
<211> LENGTH: 18
<212> TYPE: PRT
```

<213> ORGANISM: Artificial sequence
<220> FEATURE:
<223> OTHER INFORMATION: Synthetic

<400> SEQUENCE: 30

Asp Trp Phe Lys Ala Phe Tyr Asp Lys Phe Phe Glu Lys Phe Lys Glu
1               5                   10                  15
Phe Phe

<210> SEQ ID NO 31
<211> LENGTH: 18
<212> TYPE: PRT
<213> ORGANISM: Artificial sequence
<220> FEATURE:
<223> OTHER INFORMATION: Synthetic

<400> SEQUENCE: 31

Glu Trp Leu Lys Ala Phe Tyr Glu Lys Val Leu Glu Lys Leu Lys Glu
1               5                   10                  15
Leu Phe

<210> SEQ ID NO 32
<211> LENGTH: 18
<212> TYPE: PRT
<213> ORGANISM: Artificial sequence
<220> FEATURE:
<223> OTHER INFORMATION: Synthetic

<400> SEQUENCE: 32

Glu Trp Leu Lys Ala Glu Tyr Glu Lys Val Glu Glu Lys Leu Lys Glu
1               5                   10                  15
Leu Phe

<210> SEQ ID NO 33
<211> LENGTH: 18
<212> TYPE: PRT
<213> ORGANISM: Artificial sequence
<220> FEATURE:
<223> OTHER INFORMATION: Synthetic

<400> SEQUENCE: 33

Glu Trp Leu Lys Ala Glu Tyr Glu Lys Val Leu Glu Lys Leu Lys Glu
1               5                   10                  15
Leu Phe

<210> SEQ ID NO 34
<211> LENGTH: 18
<212> TYPE: PRT
<213> ORGANISM: Artificial sequence
<220> FEATURE:
<223> OTHER INFORMATION: Synthetic

<400> SEQUENCE: 34

Glu Trp Leu Lys Ala Phe Tyr Lys Lys Val Leu Glu Lys Leu Lys Glu
1               5                   10                  15
Leu Phe

<210> SEQ ID NO 35
<211> LENGTH: 22
<212> TYPE: PRT
<213> ORGANISM: Artificial sequence
<220> FEATURE:
<223> OTHER INFORMATION: Synthetic

```
<400> SEQUENCE: 35

Pro Val Leu Asp Leu Phe Arg Glu Leu Leu Asn Glu Leu Leu Glu Ala
1               5                   10                  15

Leu Lys Gln Lys Leu Lys
            20

<210> SEQ ID NO 36
<211> LENGTH: 22
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (13)..(13)
<223> OTHER INFORMATION: Xaa = Pyrrolysine

<400> SEQUENCE: 36

Pro Val Leu Asp Leu Phe Arg Glu Leu Leu Asn Leu Xaa Leu Glu Ala
1               5                   10                  15

Leu Lys Glu Lys Leu Lys
            20

<210> SEQ ID NO 37
<211> LENGTH: 22
<212> TYPE: PRT
<213> ORGANISM: Artificial sequence
<220> FEATURE:
<223> OTHER INFORMATION: Synthetic

<400> SEQUENCE: 37

Pro Val Leu Asp Leu Phe Arg Glu Leu Leu Asn Glu Leu Leu Glu Glx
1               5                   10                  15

Leu Lys Gln Lys Leu Lys
            20

<210> SEQ ID NO 38
<211> LENGTH: 23
<212> TYPE: PRT
<213> ORGANISM: Artificial sequence
<220> FEATURE:
<223> OTHER INFORMATION: Synthetic

<400> SEQUENCE: 38

Gly Val Leu Asp Leu Phe Arg Glu Leu Leu Asn Glu Leu Leu Glu Ala
1               5                   10                  15

Leu Lys Gln Lys Leu Lys Lys
            20

<210> SEQ ID NO 39
<211> LENGTH: 22
<212> TYPE: PRT
<213> ORGANISM: Artificial sequence
<220> FEATURE:
<223> OTHER INFORMATION: Synthetic

<400> SEQUENCE: 39

Pro Val Leu Asp Leu Phe Arg Glu Leu Leu Asn Glu Gly Leu Glu Ala
1               5                   10                  15

Leu Lys Gln Lys Leu Lys
            20

<210> SEQ ID NO 40
<211> LENGTH: 22
```

```
<212> TYPE: PRT
<213> ORGANISM: Artificial sequence
<220> FEATURE:
<223> OTHER INFORMATION: Synthetic

<400> SEQUENCE: 40

Gly Val Leu Asp Leu Phe Arg Glu Leu Leu Asn Glu Gly Leu Glu Ala
1               5                   10                  15

Leu Lys Gln Lys Leu Lys
            20

<210> SEQ ID NO 41
<211> LENGTH: 22
<212> TYPE: PRT
<213> ORGANISM: Artificial sequence
<220> FEATURE:
<223> OTHER INFORMATION: Synthetic

<400> SEQUENCE: 41

Pro Val Leu Asp Leu Phe Arg Glu Leu Leu Asn Glu Gly Leu Glu Ala
1               5                   10                  15

Leu Lys Gln Lys Leu Lys
            20

<210> SEQ ID NO 42
<211> LENGTH: 22
<212> TYPE: PRT
<213> ORGANISM: Artificial sequence
<220> FEATURE:
<223> OTHER INFORMATION: Synthetic

<400> SEQUENCE: 42

Pro Val Leu Asp Leu Phe Arg Glu Leu Leu Asn Glu Gly Leu Glu Ala
1               5                   10                  15

Glx Lys Gln Lys Leu Lys
            20

<210> SEQ ID NO 43
<211> LENGTH: 22
<212> TYPE: PRT
<213> ORGANISM: Artificial sequence
<220> FEATURE:
<223> OTHER INFORMATION: Synthetic

<400> SEQUENCE: 43

Pro Val Leu Asp Leu Phe Arg Glu Leu Leu Asn Glu Gly Leu Glu Trp
1               5                   10                  15

Leu Lys Gln Lys Leu Lys
            20

<210> SEQ ID NO 44
<211> LENGTH: 22
<212> TYPE: PRT
<213> ORGANISM: Artificial sequence
<220> FEATURE:
<223> OTHER INFORMATION: Synthetic

<400> SEQUENCE: 44

Pro Val Leu Asp Leu Phe Arg Glu Leu Trp Asn Glu Gly Leu Glu Ala
1               5                   10                  15

Leu Lys Gln Lys Leu Lys
            20

<210> SEQ ID NO 45
```

```
<211> LENGTH: 22
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (18)..(18)
<223> OTHER INFORMATION: Xaa = Pyrrolysine
<220> FEATURE:
<221> NAME/KEY: MISC_FEATURE
<222> LOCATION: (20)..(20)
<223> OTHER INFORMATION: Xaa = Pyrrolysine
<220> FEATURE:
<221> NAME/KEY: MISC_FEATURE
<222> LOCATION: (22)..(22)
<223> OTHER INFORMATION: Xaa = Pyrrolysine

<400> SEQUENCE: 45

Pro Val Leu Asp Leu Phe Arg Glu Leu Leu Asn Glu Gly Leu Glu Ala
1               5                   10                  15

Leu Xaa Gln Xaa Leu Xaa
            20

<210> SEQ ID NO 46
<211> LENGTH: 22
<212> TYPE: PRT
<213> ORGANISM: Artificial sequence
<220> FEATURE:
<223> OTHER INFORMATION: Synthetic

<400> SEQUENCE: 46

Pro Val Leu Asp Phe Phe Arg Glu Leu Leu Asn Glu Gly Leu Glu Ala
1               5                   10                  15

Leu Lys Gln Lys Leu Lys
            20

<210> SEQ ID NO 47
<211> LENGTH: 22
<212> TYPE: PRT
<213> ORGANISM: Artificial sequence
<220> FEATURE:
<223> OTHER INFORMATION: Synthetic

<400> SEQUENCE: 47

Pro Val Leu Glu Leu Phe Arg Glu Leu Leu Asn Glu Gly Leu Glu Ala
1               5                   10                  15

Leu Lys Gln Lys Leu Lys
            20

<210> SEQ ID NO 48
<211> LENGTH: 22
<212> TYPE: PRT
<213> ORGANISM: Artificial sequence
<220> FEATURE:
<223> OTHER INFORMATION: Synthetic

<400> SEQUENCE: 48

Pro Val Leu Asp Leu Phe Arg Glu Gly Leu Asn Glu Leu Leu Glu Ala
1               5                   10                  15

Leu Lys Gln Lys Leu Lys
            20

<210> SEQ ID NO 49
<211> LENGTH: 22
<212> TYPE: PRT
<213> ORGANISM: Artificial sequence
```

<220> FEATURE:
<223> OTHER INFORMATION: Synthetic

<400> SEQUENCE: 49

Pro Val Leu Asp Leu Phe Arg Glu Leu Gly Asn Glu Leu Leu Glu Ala
1               5                   10                  15

Leu Lys Gln Lys Leu Lys
            20

<210> SEQ ID NO 50
<211> LENGTH: 22
<212> TYPE: PRT
<213> ORGANISM: Artificial sequence
<220> FEATURE:
<223> OTHER INFORMATION: Synthetic

<400> SEQUENCE: 50

Pro Val Leu Asp Leu Phe Arg Glu Leu Leu Asn Glu Leu Gly Glu Ala
1               5                   10                  15

Leu Lys Gln Lys Leu Lys
            20

<210> SEQ ID NO 51
<211> LENGTH: 22
<212> TYPE: PRT
<213> ORGANISM: Artificial sequence
<220> FEATURE:
<223> OTHER INFORMATION: Synthetic

<400> SEQUENCE: 51

Pro Val Leu Asp Leu Phe Arg Glu Leu Leu Asn Glu Leu Leu Glu Gly
1               5                   10                  15

Leu Lys Gln Lys Leu Lys
            20

<210> SEQ ID NO 52
<211> LENGTH: 22
<212> TYPE: PRT
<213> ORGANISM: Artificial sequence
<220> FEATURE:
<223> OTHER INFORMATION: Synthetic

<400> SEQUENCE: 52

Pro Val Leu Asp Leu Phe Arg Glu Leu Leu Asn Glu Leu Leu Glu Ala
1               5                   10                  15

Gly Lys Gln Lys Leu Lys
            20

<210> SEQ ID NO 53
<211> LENGTH: 22
<212> TYPE: PRT
<213> ORGANISM: Artificial sequence
<220> FEATURE:
<223> OTHER INFORMATION: Synthetic

<400> SEQUENCE: 53

Pro Val Leu Asp Leu Phe Arg Glu Leu Leu Asn Glu Leu Leu Glu Trp
1               5                   10                  15

Leu Lys Gln Lys Leu Lys
            20

<210> SEQ ID NO 54
<211> LENGTH: 23
<212> TYPE: PRT

```
<213> ORGANISM: Artificial sequence
<220> FEATURE:
<223> OTHER INFORMATION: Synthetic

<400> SEQUENCE: 54

Pro Val Leu Asp Leu Phe Arg Glu Leu Leu Asn Glu Leu Leu Glu Ala
1               5                   10                  15

Leu Lys Gln Lys Leu Lys Lys
            20

<210> SEQ ID NO 55
<211> LENGTH: 22
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (13)..(13)
<223> OTHER INFORMATION: Xaa = Pyrrolysine

<400> SEQUENCE: 55

Pro Val Leu Asp Leu Phe Arg Glu Leu Leu Asn Glu Xaa Leu Glu Ala
1               5                   10                  15

Leu Lys Gln Lys Leu Lys
            20

<210> SEQ ID NO 56
<211> LENGTH: 22
<212> TYPE: PRT
<213> ORGANISM: Artificial sequence
<220> FEATURE:
<223> OTHER INFORMATION: Synthetic

<400> SEQUENCE: 56

Pro Val Leu Asp Leu Phe Lys Glu Leu Leu Asn Glu Leu Leu Glu Ala
1               5                   10                  15

Leu Lys Gln Lys Leu Lys
            20

<210> SEQ ID NO 57
<211> LENGTH: 22
<212> TYPE: PRT
<213> ORGANISM: Artificial sequence
<220> FEATURE:
<223> OTHER INFORMATION: Synthetic

<400> SEQUENCE: 57

Pro Val Leu Asp Leu Phe Arg Glu Leu Leu Asn Glu Leu Leu Glu Ala
1               5                   10                  15

Glx Lys Gln Lys Leu Lys
            20

<210> SEQ ID NO 58
<211> LENGTH: 22
<212> TYPE: PRT
<213> ORGANISM: Artificial sequence
<220> FEATURE:
<223> OTHER INFORMATION: Synthetic

<400> SEQUENCE: 58

Pro Val Leu Asp Leu Phe Lys Glu Leu Leu Gln Glu Leu Leu Glu Ala
1               5                   10                  15

Leu Lys Gln Lys Leu Lys
            20
```

```
<210> SEQ ID NO 59
<211> LENGTH: 22
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (18)..(18)
<223> OTHER INFORMATION: Xaa = Pyrrolysine
<220> FEATURE:
<221> NAME/KEY: MISC_FEATURE
<222> LOCATION: (20)..(20)
<223> OTHER INFORMATION: Xaa = Pyrrolysine
<220> FEATURE:
<221> NAME/KEY: MISC_FEATURE
<222> LOCATION: (22)..(22)
<223> OTHER INFORMATION: Xaa = Pyrrolysine

<400> SEQUENCE: 59

Pro Val Leu Asp Leu Phe Arg Glu Leu Leu Asn Glu Leu Leu Glu Ala
1               5                   10                  15

Leu Xaa Gln Xaa Leu Xaa
            20

<210> SEQ ID NO 60
<211> LENGTH: 22
<212> TYPE: PRT
<213> ORGANISM: Artificial sequence
<220> FEATURE:
<223> OTHER INFORMATION: Synthetic

<400> SEQUENCE: 60

Pro Val Leu Asp Leu Phe Arg Glu Leu Trp Asn Glu Leu Leu Glu Ala
1               5                   10                  15

Leu Lys Gln Lys Leu Lys
            20

<210> SEQ ID NO 61
<211> LENGTH: 22
<212> TYPE: PRT
<213> ORGANISM: Artificial sequence
<220> FEATURE:
<223> OTHER INFORMATION: Synthetic

<400> SEQUENCE: 61

Pro Val Leu Asp Leu Leu Arg Glu Leu Leu Asn Glu Leu Leu Glu Ala
1               5                   10                  15

Leu Lys Gln Lys Leu Lys
            20

<210> SEQ ID NO 62
<211> LENGTH: 22
<212> TYPE: PRT
<213> ORGANISM: Artificial sequence
<220> FEATURE:
<223> OTHER INFORMATION: Synthetic

<400> SEQUENCE: 62

Pro Val Leu Glu Leu Phe Lys Glu Leu Leu Gln Glu Leu Leu Glu Ala
1               5                   10                  15

Leu Lys Gln Lys Leu Lys
            20

<210> SEQ ID NO 63
```

```
<211> LENGTH: 22
<212> TYPE: PRT
<213> ORGANISM: Artificial sequence
<220> FEATURE:
<223> OTHER INFORMATION: Synthetic

<400> SEQUENCE: 63

Pro Leu Leu Glu Leu Phe Lys Glu Leu Leu Gln Glu Leu Leu Glu Ala
1               5                   10                  15

Leu Lys Gln Lys Leu Lys
            20

<210> SEQ ID NO 64
<211> LENGTH: 22
<212> TYPE: PRT
<213> ORGANISM: Artificial sequence
<220> FEATURE:
<223> OTHER INFORMATION: Synthetic

<400> SEQUENCE: 64

Pro Val Leu Asp Leu Phe Arg Glu Leu Leu Asn Glu Leu Leu Glu Ala
1               5                   10                  15

Leu Gln Lys Lys Leu Lys
            20

<210> SEQ ID NO 65
<211> LENGTH: 22
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (13)..(13)
<223> OTHER INFORMATION: Xaa = Pyrrolysine

<400> SEQUENCE: 65

Pro Val Leu Asp Phe Phe Arg Glu Leu Leu Asn Glu Xaa Leu Glu Ala
1               5                   10                  15

Leu Lys Gln Lys Leu Lys
            20

<210> SEQ ID NO 66
<211> LENGTH: 22
<212> TYPE: PRT
<213> ORGANISM: Artificial sequence
<220> FEATURE:
<223> OTHER INFORMATION: Synthetic

<400> SEQUENCE: 66

Pro Val Leu Asp Leu Phe Arg Glu Leu Leu Asn Glu Leu Leu Glu Leu
1               5                   10                  15

Leu Lys Gln Lys Leu Lys
            20

<210> SEQ ID NO 67
<211> LENGTH: 22
<212> TYPE: PRT
<213> ORGANISM: Artificial sequence
<220> FEATURE:
<223> OTHER INFORMATION: Synthetic

<400> SEQUENCE: 67

Pro Val Leu Asp Leu Phe Arg Glu Leu Leu Asn Glu Leu Glx Glu Ala
1               5                   10                  15
```

-continued

Leu Lys Gln Lys Leu Lys
            20

<210> SEQ ID NO 68
<211> LENGTH: 22
<212> TYPE: PRT
<213> ORGANISM: Artificial sequence
<220> FEATURE:
<223> OTHER INFORMATION: Synthetic

<400> SEQUENCE: 68

Pro Val Leu Asp Leu Phe Arg Glu Leu Leu Asn Glu Leu Trp Glu Ala
1               5                   10                  15

Leu Lys Gln Lys Leu Lys
            20

<210> SEQ ID NO 69
<211> LENGTH: 22
<212> TYPE: PRT
<213> ORGANISM: Artificial sequence
<220> FEATURE:
<223> OTHER INFORMATION: Synthetic

<400> SEQUENCE: 69

Ala Val Leu Asp Leu Phe Arg Glu Leu Leu Asn Glu Leu Leu Glu Ala
1               5                   10                  15

Leu Lys Gln Lys Leu Lys
            20

<210> SEQ ID NO 70
<211> LENGTH: 22
<212> TYPE: PRT
<213> ORGANISM: Artificial sequence
<220> FEATURE:
<223> OTHER INFORMATION: Synthetic

<400> SEQUENCE: 70

Gln Val Leu Asp Leu Phe Arg Glu Leu Leu Asn Glu Leu Leu Glu Ala
1               5                   10                  15

Leu Lys Gln Lys Leu Lys
            20

<210> SEQ ID NO 71
<211> LENGTH: 22
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Xaa = Pyrrolysine
<220> FEATURE:
<221> NAME/KEY: MISC_FEATURE
<222> LOCATION: (18)..(18)
<223> OTHER INFORMATION: Xaa = Pyrrolysine
<220> FEATURE:
<221> NAME/KEY: MISC_FEATURE
<222> LOCATION: (20)..(20)
<223> OTHER INFORMATION: Xaa = Pyrrolysine
<220> FEATURE:
<221> NAME/KEY: MISC_FEATURE
<222> LOCATION: (22)..(22)
<223> OTHER INFORMATION: Xaa = Pyrrolysine

<400> SEQUENCE: 71

Pro Val Leu Asp Leu Phe Xaa Glu Leu Leu Asn Glu Leu Leu Glu Ala
1               5                   10                  15

Leu Xaa Gln Xaa Leu Xaa
            20

<210> SEQ ID NO 72
<211> LENGTH: 22
<212> TYPE: PRT
<213> ORGANISM: Artificial sequence
<220> FEATURE:
<223> OTHER INFORMATION: Synthetic

<400> SEQUENCE: 72

Asn Val Leu Asp Leu Phe Arg Glu Leu Leu Asn Glu Leu Leu Glu Ala
1               5                   10                  15

Leu Lys Gln Lys Leu Lys
            20

<210> SEQ ID NO 73
<211> LENGTH: 22
<212> TYPE: PRT
<213> ORGANISM: Artificial sequence
<220> FEATURE:
<223> OTHER INFORMATION: Synthetic

<400> SEQUENCE: 73

Pro Val Leu Asp Leu Phe Arg Glu Leu Leu Asn Glu Leu Leu Glu Phe
1               5                   10                  15

Leu Lys Gln Lys Leu Lys
            20

<210> SEQ ID NO 74
<211> LENGTH: 22
<212> TYPE: PRT
<213> ORGANISM: Artificial sequence
<220> FEATURE:
<223> OTHER INFORMATION: Synthetic

<400> SEQUENCE: 74

Pro Val Leu Glu Leu Phe Asn Asp Leu Leu Arg Glu Leu Leu Glu Ala
1               5                   10                  15

Leu Gln Lys Lys Leu Lys
            20

<210> SEQ ID NO 75
<211> LENGTH: 22
<212> TYPE: PRT
<213> ORGANISM: Artificial sequence
<220> FEATURE:
<223> OTHER INFORMATION: Synthetic

<400> SEQUENCE: 75

Pro Val Leu Glu Leu Phe Asn Asp Leu Leu Arg Glu Leu Leu Glu Ala
1               5                   10                  15

Leu Lys Gln Lys Leu Lys
            20

<210> SEQ ID NO 76
<211> LENGTH: 22
<212> TYPE: PRT
<213> ORGANISM: Artificial sequence
<220> FEATURE:
<223> OTHER INFORMATION: Synthetic

<400> SEQUENCE: 76

Pro Val Leu Glu Leu Phe Lys Glu Leu Leu Asn Glu Leu Leu Asp Ala

```
1               5                  10                 15
Leu Arg Gln Lys Leu Lys
            20

<210> SEQ ID NO 77
<211> LENGTH: 22
<212> TYPE: PRT
<213> ORGANISM: Artificial sequence
<220> FEATURE:
<223> OTHER INFORMATION: Synthetic

<400> SEQUENCE: 77

Pro Val Leu Asp Leu Phe Arg Glu Leu Leu Glu Asn Leu Leu Glu Ala
1               5                  10                 15
Leu Gln Lys Lys Leu Lys
            20

<210> SEQ ID NO 78
<211> LENGTH: 22
<212> TYPE: PRT
<213> ORGANISM: Artificial sequence
<220> FEATURE:
<223> OTHER INFORMATION: Synthetic

<400> SEQUENCE: 78

Pro Val Leu Glu Leu Phe Glu Arg Leu Leu Glu Asp Leu Leu Gln Ala
1               5                  10                 15
Leu Asn Lys Lys Leu Lys
            20

<210> SEQ ID NO 79
<211> LENGTH: 22
<212> TYPE: PRT
<213> ORGANISM: Artificial sequence
<220> FEATURE:
<223> OTHER INFORMATION: Synthetic

<400> SEQUENCE: 79

Pro Val Leu Glu Leu Phe Glu Arg Leu Leu Glu Asp Leu Leu Lys Ala
1               5                  10                 15
Leu Asn Gln Lys Leu Lys
            20

<210> SEQ ID NO 80
<211> LENGTH: 22
<212> TYPE: PRT
<213> ORGANISM: Artificial sequence
<220> FEATURE:
<223> OTHER INFORMATION: Synthetic

<400> SEQUENCE: 80

Asp Val Leu Asp Leu Phe Arg Glu Leu Leu Asn Glu Leu Leu Glu Ala
1               5                  10                 15
Leu Lys Gln Lys Leu Lys
            20

<210> SEQ ID NO 81
<211> LENGTH: 22
<212> TYPE: PRT
<213> ORGANISM: Artificial sequence
<220> FEATURE:
<223> OTHER INFORMATION: Synthetic

<400> SEQUENCE: 81
```

```
Pro Ala Leu Glu Leu Phe Lys Asp Leu Leu Gln Glu Leu Leu Glu Ala
1               5                   10                  15
Leu Lys Gln Lys Leu Lys
            20
```

<210> SEQ ID NO 82
<211> LENGTH: 18
<212> TYPE: PRT
<213> ORGANISM: Artificial sequence
<220> FEATURE:
<223> OTHER INFORMATION: Synthetic

<400> SEQUENCE: 82

```
Pro Val Leu Asp Leu Leu Arg Glu Leu Leu Glu Glu Leu Lys Gln Lys
1               5                   10                  15
Leu Lys
```

<210> SEQ ID NO 83
<211> LENGTH: 18
<212> TYPE: PRT
<213> ORGANISM: Artificial sequence
<220> FEATURE:
<223> OTHER INFORMATION: Synthetic

<400> SEQUENCE: 83

```
Pro Val Leu Asp Leu Phe Lys Glu Leu Leu Glu Glu Leu Lys Gln Lys
1               5                   10                  15
Leu Lys
```

<210> SEQ ID NO 84
<211> LENGTH: 18
<212> TYPE: PRT
<213> ORGANISM: Artificial sequence
<220> FEATURE:
<223> OTHER INFORMATION: Synthetic

<400> SEQUENCE: 84

```
Pro Val Leu Asp Leu Phe Arg Glu Leu Leu Glu Glu Leu Lys Gln Lys
1               5                   10                  15
Leu Lys
```

<210> SEQ ID NO 85
<211> LENGTH: 18
<212> TYPE: PRT
<213> ORGANISM: Artificial sequence
<220> FEATURE:
<223> OTHER INFORMATION: Synthetic

<400> SEQUENCE: 85

```
Pro Val Leu Glu Leu Phe Arg Glu Leu Leu Glu Glu Leu Lys Gln Lys
1               5                   10                  15
Leu Lys
```

<210> SEQ ID NO 86
<211> LENGTH: 18
<212> TYPE: PRT
<213> ORGANISM: Artificial sequence
<220> FEATURE:
<223> OTHER INFORMATION: Synthetic

<400> SEQUENCE: 86

```
Pro Val Leu Glu Leu Phe Lys Glu Leu Leu Glu Glu Leu Lys Gln Lys
1               5                   10                  15
```

Leu Lys

<210> SEQ ID NO 87
<211> LENGTH: 18
<212> TYPE: PRT
<213> ORGANISM: Artificial sequence
<220> FEATURE:
<223> OTHER INFORMATION: Synthetic

<400> SEQUENCE: 87

Pro Val Leu Asp Leu Phe Arg Glu Leu Leu Glu Glu Leu Lys Asn Lys
1               5                   10                  15

Leu Lys

<210> SEQ ID NO 88
<211> LENGTH: 18
<212> TYPE: PRT
<213> ORGANISM: Artificial sequence
<220> FEATURE:
<223> OTHER INFORMATION: Synthetic

<400> SEQUENCE: 88

Pro Leu Leu Asp Leu Phe Arg Glu Leu Leu Glu Glu Leu Lys Gln Lys
1               5                   10                  15

Leu Lys

<210> SEQ ID NO 89
<211> LENGTH: 18
<212> TYPE: PRT
<213> ORGANISM: Artificial sequence
<220> FEATURE:
<223> OTHER INFORMATION: Synthetic

<400> SEQUENCE: 89

Gly Val Leu Asp Leu Phe Arg Glu Leu Leu Glu Glu Leu Lys Gln Lys
1               5                   10                  15

Leu Lys

<210> SEQ ID NO 90
<211> LENGTH: 18
<212> TYPE: PRT
<213> ORGANISM: Artificial sequence
<220> FEATURE:
<223> OTHER INFORMATION: Synthetic

<400> SEQUENCE: 90

Pro Val Leu Asp Leu Phe Arg Glu Leu Trp Glu Glu Leu Lys Gln Lys
1               5                   10                  15

Leu Lys

<210> SEQ ID NO 91
<211> LENGTH: 18
<212> TYPE: PRT
<213> ORGANISM: Artificial sequence
<220> FEATURE:
<223> OTHER INFORMATION: Synthetic

<400> SEQUENCE: 91

Asn Val Leu Asp Leu Phe Arg Glu Leu Leu Glu Glu Leu Lys Gln Lys
1               5                   10                  15

Leu Lys

<210> SEQ ID NO 92

```
<211> LENGTH: 18
<212> TYPE: PRT
<213> ORGANISM: Artificial sequence
<220> FEATURE:
<223> OTHER INFORMATION: Synthetic

<400> SEQUENCE: 92

Pro Leu Leu Asp Leu Phe Lys Glu Leu Leu Glu Glu Leu Lys Gln Lys
1               5                   10                  15

Leu Lys

<210> SEQ ID NO 93
<211> LENGTH: 18
<212> TYPE: PRT
<213> ORGANISM: Artificial sequence
<220> FEATURE:
<223> OTHER INFORMATION: Synthetic

<400> SEQUENCE: 93

Pro Ala Leu Glu Leu Phe Lys Asp Leu Leu Glu Glu Leu Arg Gln Lys
1               5                   10                  15

Leu Arg

<210> SEQ ID NO 94
<211> LENGTH: 18
<212> TYPE: PRT
<213> ORGANISM: Artificial sequence
<220> FEATURE:
<223> OTHER INFORMATION: Synthetic

<400> SEQUENCE: 94

Ala Val Leu Asp Leu Phe Arg Glu Leu Leu Glu Glu Leu Lys Gln Lys
1               5                   10                  15

Leu Lys

<210> SEQ ID NO 95
<211> LENGTH: 18
<212> TYPE: PRT
<213> ORGANISM: Artificial sequence
<220> FEATURE:
<223> OTHER INFORMATION: Synthetic

<400> SEQUENCE: 95

Pro Val Leu Asp Phe Phe Arg Glu Leu Leu Glu Glu Leu Lys Gln Lys
1               5                   10                  15

Leu Lys

<210> SEQ ID NO 96
<211> LENGTH: 18
<212> TYPE: PRT
<213> ORGANISM: Artificial sequence
<220> FEATURE:
<223> OTHER INFORMATION: Synthetic

<400> SEQUENCE: 96

Pro Val Leu Asp Leu Phe Arg Glu Trp Leu Glu Glu Leu Lys Gln Lys
1               5                   10                  15

Leu Lys

<210> SEQ ID NO 97
<211> LENGTH: 18
<212> TYPE: PRT
<213> ORGANISM: Artificial sequence
<220> FEATURE:
```

<223> OTHER INFORMATION: Synthetic

<400> SEQUENCE: 97

Pro Leu Leu Glu Leu Leu Lys Glu Leu Leu Glu Glu Leu Lys Gln Lys
1               5                   10                  15

Leu Lys

<210> SEQ ID NO 98
<211> LENGTH: 18
<212> TYPE: PRT
<213> ORGANISM: Artificial sequence
<220> FEATURE:
<223> OTHER INFORMATION: Synthetic

<400> SEQUENCE: 98

Pro Val Leu Glu Leu Leu Lys Glu Leu Leu Glu Glu Leu Lys Gln Lys
1               5                   10                  15

Leu Lys

<210> SEQ ID NO 99
<211> LENGTH: 18
<212> TYPE: PRT
<213> ORGANISM: Artificial sequence
<220> FEATURE:
<223> OTHER INFORMATION: Synthetic

<400> SEQUENCE: 99

Pro Ala Leu Glu Leu Phe Lys Asp Leu Leu Glu Glu Leu Arg Gln Arg
1               5                   10                  15

Leu Lys

<210> SEQ ID NO 100
<211> LENGTH: 18
<212> TYPE: PRT
<213> ORGANISM: Artificial sequence
<220> FEATURE:
<223> OTHER INFORMATION: Synthetic

<400> SEQUENCE: 100

Pro Val Leu Asp Leu Phe Arg Glu Leu Leu Glu Glu Leu Leu Gln Lys
1               5                   10                  15

Leu Lys

<210> SEQ ID NO 101
<211> LENGTH: 18
<212> TYPE: PRT
<213> ORGANISM: Artificial sequence
<220> FEATURE:
<223> OTHER INFORMATION: Synthetic

<400> SEQUENCE: 101

Pro Val Leu Asp Leu Phe Arg Glu Leu Leu Glu Glu Leu Lys Gln Lys
1               5                   10                  15

Leu Lys

<210> SEQ ID NO 102
<211> LENGTH: 18
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (14)..(14)

```
<223> OTHER INFORMATION: Xaa = Pyrrolysine
<220> FEATURE:
<221> NAME/KEY: MISC_FEATURE
<222> LOCATION: (16)..(16)
<223> OTHER INFORMATION: Xaa = Pyrrolysine
<220> FEATURE:
<221> NAME/KEY: MISC_FEATURE
<222> LOCATION: (18)..(18)
<223> OTHER INFORMATION: Xaa = Pyrrolysine

<400> SEQUENCE: 102

Pro Val Leu Asp Leu Phe Arg Glu Leu Leu Glu Glu Leu Xaa Gln Xaa
1               5                   10                  15

Leu Xaa

<210> SEQ ID NO 103
<211> LENGTH: 18
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Xaa = Pyrrolysine
<220> FEATURE:
<221> NAME/KEY: MISC_FEATURE
<222> LOCATION: (14)..(14)
<223> OTHER INFORMATION: Xaa = Pyrrolysine
<220> FEATURE:
<221> NAME/KEY: MISC_FEATURE
<222> LOCATION: (16)..(16)
<223> OTHER INFORMATION: Xaa = Pyrrolysine

<400> SEQUENCE: 103

Pro Val Leu Asp Leu Phe Xaa Glu Leu Leu Glu Glu Leu Xaa Gln Xaa
1               5                   10                  15

Leu Lys

<210> SEQ ID NO 104
<211> LENGTH: 18
<212> TYPE: PRT
<213> ORGANISM: Artificial sequence
<220> FEATURE:
<223> OTHER INFORMATION: Synthetic

<400> SEQUENCE: 104

Pro Ala Leu Glu Leu Phe Lys Asp Leu Leu Glu Glu Phe Arg Gln Arg
1               5                   10                  15

Leu Lys

<210> SEQ ID NO 105
<211> LENGTH: 18
<212> TYPE: PRT
<213> ORGANISM: Artificial sequence
<220> FEATURE:
<223> OTHER INFORMATION: Synthetic

<400> SEQUENCE: 105

Pro Val Leu Asp Leu Phe Arg Glu Leu Leu Glu Glu Leu Lys Gln Lys
1               5                   10                  15

Leu Lys

<210> SEQ ID NO 106
<211> LENGTH: 18
<212> TYPE: PRT
<213> ORGANISM: Artificial sequence
```

```
<220> FEATURE:
<223> OTHER INFORMATION: Synthetic

<400> SEQUENCE: 106

Pro Val Leu Asp Leu Phe Arg Glu Leu Leu Glu Glu Trp Lys Gln Lys
1               5                   10                  15

Leu Lys

<210> SEQ ID NO 107
<211> LENGTH: 18
<212> TYPE: PRT
<213> ORGANISM: Artificial sequence
<220> FEATURE:
<223> OTHER INFORMATION: Synthetic

<400> SEQUENCE: 107

Pro Val Leu Glu Leu Phe Glu Arg Leu Leu Glu Asp Leu Gln Lys Lys
1               5                   10                  15

Leu Lys

<210> SEQ ID NO 108
<211> LENGTH: 18
<212> TYPE: PRT
<213> ORGANISM: Artificial sequence
<220> FEATURE:
<223> OTHER INFORMATION: Synthetic

<400> SEQUENCE: 108

Pro Val Leu Asp Leu Phe Arg Glu Leu Leu Glu Lys Leu Glu Gln Lys
1               5                   10                  15

Leu Lys

<210> SEQ ID NO 109
<211> LENGTH: 18
<212> TYPE: PRT
<213> ORGANISM: Artificial sequence
<220> FEATURE:
<223> OTHER INFORMATION: Synthetic

<400> SEQUENCE: 109

Pro Leu Leu Glu Leu Phe Lys Glu Leu Leu Glu Glu Leu Lys Gln Lys
1               5                   10                  15

Leu Lys

<210> SEQ ID NO 110
<211> LENGTH: 22
<212> TYPE: DNA
<213> ORGANISM: Artificial sequence
<220> FEATURE:
<223> OTHER INFORMATION: Synthetic

<400> SEQUENCE: 110
ttgctttatg ggctcaagaa tg                                     22

<210> SEQ ID NO 111
<211> LENGTH: 23
<212> TYPE: DNA
<213> ORGANISM: Artificial sequence
<220> FEATURE:
<223> OTHER INFORMATION: Synthetic

<400> SEQUENCE: 111
ggagaccctc tgagattctg ctt                                    23
```

<210> SEQ ID NO 112
<211> LENGTH: 21
<212> TYPE: DNA
<213> ORGANISM: Artificial sequence
<220> FEATURE:
<223> OTHER INFORMATION: Synthetic

<400> SEQUENCE: 112
cttcttcgac ccggaaaatt t                                          21

<210> SEQ ID NO 113
<211> LENGTH: 23
<212> TYPE: DNA
<213> ORGANISM: Artificial sequence
<220> FEATURE:
<223> OTHER INFORMATION: Synthetic

<400> SEQUENCE: 113
ccggaagtag gtgatgttct tgt                                        23

<210> SEQ ID NO 114
<211> LENGTH: 21
<212> TYPE: DNA
<213> ORGANISM: Artificial sequence
<220> FEATURE:
<223> OTHER INFORMATION: Synthetic

<400> SEQUENCE: 114
gcggctaatg ggtggaatct a                                          21

<210> SEQ ID NO 115
<211> LENGTH: 26
<212> TYPE: DNA
<213> ORGANISM: Artificial sequence
<220> FEATURE:
<223> OTHER INFORMATION: Synthetic

<400> SEQUENCE: 115
cctcatttat actggcagaa aggaat                                     26

<210> SEQ ID NO 116
<211> LENGTH: 18
<212> TYPE: DNA
<213> ORGANISM: Artificial sequence
<220> FEATURE:
<223> OTHER INFORMATION: Synthetic

<400> SEQUENCE: 116
tcccgagggc ctctagga                                              18

<210> SEQ ID NO 117
<211> LENGTH: 22
<212> TYPE: DNA
<213> ORGANISM: Artificial sequence
<220> FEATURE:
<223> OTHER INFORMATION: Synthetic

<400> SEQUENCE: 117
gggacaaggt cagcaagatc tt                                         22

<210> SEQ ID NO 118
<211> LENGTH: 21
<212> TYPE: DNA
<213> ORGANISM: Artificial sequence
<220> FEATURE:
<223> OTHER INFORMATION: Synthetic

<400> SEQUENCE: 118
ttgttcaagc agcgagtgtt g                                                      21

<210> SEQ ID NO 119
<211> LENGTH: 19
<212> TYPE: DNA
<213> ORGANISM: Artificial sequence
<220> FEATURE:
<223> OTHER INFORMATION: Synthetic

<400> SEQUENCE: 119
gcatcctcgg gaccttctc                                                         19

<210> SEQ ID NO 120
<211> LENGTH: 19
<212> TYPE: DNA
<213> ORGANISM: Artificial sequence
<220> FEATURE:
<223> OTHER INFORMATION: Synthetic

<400> SEQUENCE: 120
gctgactctg gcgcacact                                                         19

<210> SEQ ID NO 121
<211> LENGTH: 20
<212> TYPE: DNA
<213> ORGANISM: Artificial sequence
<220> FEATURE:
<223> OTHER INFORMATION: Synthetic

<400> SEQUENCE: 121
ccatccttga acagggcaaa                                                        20

<210> SEQ ID NO 122
<211> LENGTH: 20
<212> TYPE: DNA
<213> ORGANISM: Artificial sequence
<220> FEATURE:
<223> OTHER INFORMATION: Synthetic

<400> SEQUENCE: 122
tcccagcact caaccaacct                                                        20

<210> SEQ ID NO 123
<211> LENGTH: 24
<212> TYPE: DNA
<213> ORGANISM: Artificial sequence
<220> FEATURE:
<223> OTHER INFORMATION: Synthetic

<400> SEQUENCE: 123
cagctcagaa ttaagcctca atcc                                                   24

<210> SEQ ID NO 124
<211> LENGTH: 19
<212> TYPE: DNA
<213> ORGANISM: Artificial sequence
<220> FEATURE:
<223> OTHER INFORMATION: Synthetic

<400> SEQUENCE: 124
accagcatcg tgcctgaag                                                         19

<210> SEQ ID NO 125

```
<211> LENGTH: 21
<212> TYPE: DNA
<213> ORGANISM: Artificial sequence
<220> FEATURE:
<223> OTHER INFORMATION: Synthetic

<400> SEQUENCE: 125
ccaagagaaa aaggccagtg a                                              21
```